(12) United States Patent
Jeon et al.

(10) Patent No.: US 11,383,239 B2
(45) Date of Patent: Jul. 12, 2022

(54) MICROFLUIDIC DEVICE HAVING PARTIALLY ENCLOSED MICROFLUIDIC CHANNEL AND USE THEREOF

(71) Applicant: CURIOCHIPS, Seoul (KR)

(72) Inventors: Noo Li Jeon, Seoul (KR); Byungjun Lee, Seoul (KR); James Yu, Seoul (KR); Jihoon Ko, Seoul (KR)

(73) Assignee: CURIOCHIPS, Seoul (KR)

(*) Notice: Subject to any disclaimer, the term of this patent is extended or adjusted under 35 U.S.C. 154(b) by 369 days.

(21) Appl. No.: 16/721,559

(22) Filed: Dec. 19, 2019

(65) Prior Publication Data

US 2020/0156062 A1 May 21, 2020

Related U.S. Application Data

(63) Continuation-in-part of application No. PCT/US2018/038325, filed on Jun. 19, 2018.

(30) Foreign Application Priority Data

Jun. 19, 2017 (KR) ........................ 10-2017-0077641

(51) Int. Cl.
*B01L 3/00* (2006.01)
*C12M 3/06* (2006.01)

(52) U.S. Cl.
CPC ......... *B01L 3/50273* (2013.01); *C12M 23/16* (2013.01); *B01L 2300/0858* (2013.01);
(Continued)

(58) Field of Classification Search
CPC ......... B01L 3/50273; B01L 2300/0858; B01L 2300/0861; B01L 2400/0406;
(Continued)

(56) References Cited

U.S. PATENT DOCUMENTS 5,658,377 A 8/1997 Craig
6,210,986 B1 4/2001 Arnold et al.
(Continued)

FOREIGN PATENT DOCUMENTS

EP 1827693 B1 3/2010
WO WO 2018236901 A1 12/2018

OTHER PUBLICATIONS

International Search Report / Written Opinion, PCT/US2018/038325, dated Oct. 24, 2018, 11 pgs.
(Continued)

*Primary Examiner* — Jennifer Wecker
*Assistant Examiner* — Oyeleye Alexander Alabi
(74) *Attorney, Agent, or Firm* — Morgan, Lewis & Bockius LLP

(57) ABSTRACT

A microfluidic device in which microfluidic channels are embedded in a culture medium chamber and have open sides. The microfluidic device is patterned with a fluid moved along a hydrophilic surface due to capillary force, and the fluid may be rapidly and uniformly patterned along an inner corner path and a microfluidic channel. In the microfluidic device, the microfluidic channel is connected to facilitate fluid flow with a culture medium through open sides thereof and openings, and thus may provide a cell culture environment in which high gas saturation is maintained. In addition, several microfluidic devices formed on one common substrate are described. Such microfluidic devices may be manufactured of a hydrophilic engineering plastic by injection molding.

18 Claims, 55 Drawing Sheets

(52) U.S. Cl.
CPC ............... *B01L 2300/0861* (2013.01); *B01L 2400/0406* (2013.01)

(58) Field of Classification Search
CPC ....... B01L 3/502761; B01L 2200/0647; B01L 2300/088; B01L 2300/12; C12M 23/16; C12M 23/20; C12M 23/58; C12M 35/08; C12M 23/12; C12N 2513/00; C12N 2521/00; C12N 5/0068
See application file for complete search history.

(56) References Cited

U.S. PATENT DOCUMENTS

| | | |
|---|---|---|
| 7,554,175 B2 | 6/2009 | Hachigo |
| 2002/0100714 A1 | 8/2002 | Staats |
| 2002/0117517 A1 | 8/2002 | Unger et al. |
| 2003/0026740 A1 | 2/2003 | Staats |
| 2004/0206399 A1 | 10/2004 | Heller et al. |
| 2007/0286774 A1* | 12/2007 | Barholm-Hansen ........................ B01L 3/502746 422/400 |
| 2010/0089529 A1 | 4/2010 | Barholm-Hansen et al. |

OTHER PUBLICATIONS

International Search Report / Written Opinion, PCT/US2020/066174, dated Mar. 9, 2021, 7 pgs.
Curiochips, European Search Report, Application No. 18819774.3, dated Feb. 22, 2021, 8 pgs.

\* cited by examiner (a)

(b)

(c)

(a)

(b)

(c)

(a)

(b)

(a)

Bright Filed image of
Day3 Lymphangiovasculogenesis (b)

Confocal fluorescence image of
Day3 Lymphangiovasculogenesis (c)

Confocal fluorescence image of
Day5 Lymphangiovasculogenesis

3802

3816
3812
3814

$$\Delta P_c = \frac{2\gamma}{h_c}(\sqrt{2}\,(cos\frac{\emptyset}{2} - sin\frac{\emptyset}{2}) - 2cos\theta) < 0 \qquad \Delta P_r = 2\gamma\,(\frac{1}{w_r} - \frac{cos\theta}{h_r}) < 0$$

$$\Delta P_c = \frac{4\gamma}{h_c}\left(\cos\left(\frac{\pi}{8}+\frac{\phi}{4}\right)-\cos\theta\right)<0 \qquad \Delta P_r = 2\gamma\left(\frac{1}{w_r}-\frac{\cos\theta}{h_r}\right)<0$$

MICROFLUIDIC DEVICE HAVING PARTIALLY ENCLOSED MICROFLUIDIC CHANNEL AND USE THEREOF

RELATED APPLICATIONS

This application is a continuation-in-part of the international application No. PCT/US2018/038325, filed Jun. 19, 2018, which claims priority to the Korean patent application No. 10-2017-0077641, filed Jun. 19, 2017, both of which are incorporated by reference herein in their entireties.

TECHNICAL FIELD

This application relates to microfluidic devices and methods for using the same. In particular, this application relates to methods for culturing cells or tissues using such microfluidic devices and methods for processing cells or tissues using such microfluidic devices, including co-culturing cells or tissue using a microfluidic device.

BACKGROUND

Microfluidic devices having various structures of a microfluidic channel, chamber or reservoir have been used in various fields such as three-dimensional cell co-culture. By using a microfluidic device, cells constituting a specific tissue or organ are cultured in vitro for the study and research of the function, characteristics, and epidemiological and physiological cell responses of the tissue or organ, and also used to replace an animal test in new drug development.

However, conventional microfluidic devices for cell culture require a microfluidic channel that defines at least four sides of a volume in which cells are cultured. Thus, the spatial activity of cells is reduced or restricted. In addition, such a conventional microfluidic device requires a separate culture medium channel through which cell culture medium is provided. In conventional microfluidic devices, the cell culture medium may not be provided evenly to cells in the microfluidic channel.

SUMMARY

Accordingly, there is a need for microfluidic devices for cell culture that address the above-discussed challenges and restrictions. The microfluidic devices described in this application address the above-discussed challenges and restrictions. In addition, the microfluidic devices described in this application address additional challenges and restrictions associated with conventional microfluidic devices, some of which are described below.

In accordance with some embodiments, a microfluidic device has a microfluidic channel which is embedded in a chamber and open at both ends.

In accordance with some embodiments, a method for patterning a fluid includes using a microfluidic device described herein.

In accordance with some embodiments, a method for culturing cells, tissue, or both cells and tissue, or co-culturing cells and tissue includes using a microfluidic device described herein.

In accordance with some embodiments, a microfluidic device having a microfluidic channel in which at least a surface in contact with a fluid is formed of a hydrophilic material includes: a substrate having a top surface and a bottom surface; outer walls which are attached (or coupled or bonded) to (or integrated with) the top surface of the substrate such that one or more cavities with an open top are formed and which include an inner surface facing the cavity and an outer surface opposite to the inner surface; inner corner paths formed by the boundary at which the inner surface of the outer wall meets the top surface of the substrate; and a microfluidic channel module including a top surface, a bottom surface and both ends, disposed in one or more cavities to cross the inside of the cavity by bonding the both ends to different positions on the inner surface of the outer wall. In the microfluidic device, a part or all of the bottom surface of the channel module is spaced apart from the top surface of the substrate to form one or more microfluidic channels connected with the inner corner path so as to be able to move a fluid by capillary force between the bottom surface of the microfluidic channel module and the top surface of the substrate.

In some embodiments, the bottom surface of the microfluidic channel module and the top surface of the substrate are hydrophilic surfaces (e.g., so that a polar liquid, such as a water-based solution, moves by capillary force between the bottom surface of the microfluidic channel module and the top surface of the substrate). In some embodiments, at least one of the microfluidic channel module and the substrate is made from an inherently hydrophilic material so that at least one of the bottom surface of the microfluidic channel module and the top surface of the substrate has a hydrophilic surface. In some embodiments, at least one of the microfluidic channel module and the substrate is made from an inherently hydrophobic material but the surface of the inherently hydrophobic material is modified so that the modified surface has a hydrophilic surface.

In some embodiments, the bottom surface of the microfluidic channel module and the top surface of the substrate are hydrophobic surfaces (e.g., so that a non-polar liquid, such as a hydrocarbon-based solution, moves by capillary force between the bottom surface of the microfluidic channel module and the top surface of the substrate). In some embodiments, at least one of the microfluidic channel module and the substrate is made from an inherently hydrophobic material so that at least one of the bottom surface of the microfluidic channel module and the top surface of the substrate has a hydrophobic surface. In some embodiments, at least one of the microfluidic channel module and the substrate is made from an inherently hydrophilic material but the surface of the inherently hydrophobic material is modified so that the modified surface has a hydrophobic surface.

In some embodiments, a microfluidic device has a microfluidic channel which is embedded in a chamber and open at both ends, in which when an inner corner forming one closed curve has a circular, polygonal or atypical shape, and a path of the inner corner has a polygonal or atypical shape, a radius (R) value of the inner corner is 0.05 mm or more.

In some embodiments, in the microfluidic device, a part or all of the top surface of the microfluidic channel module extends upward such that a partition dividing the cavity is formed.

In some embodiments, the inner corner path forms one or more closed curves.

In some embodiments, when the closed curve has a polygonal shape, the microfluidic device includes a fillet on the inner surface of the outer wall such that a radius (R) value of a corresponding inner corner path is 0.05 mm or more. In some embodiments, the microfluidic device has a closed curve defining an inner corner path having a polygonal shape, and the microfluidic device includes a fillet of the inner surface of the outer wall, where a radius (R) value of a corresponding inner corner path is 0.05 mm or more.

In some embodiments, the microfluidic channel module includes two or more microfluidic channels sequentially increased in height.

In some embodiments, one or more recesses are formed, parallel to the microfluidic channel, on the bottom surface of the microfluidic channel module.

In some embodiments, two or more recesses are formed, parallel to the microfluidic channel, on the bottom surface of the microfluidic channel module, and sequentially increased in depth.

In some embodiments, the microfluidic channel module includes one or more openings passing from the top surface thereof to the recess such that a cavity formed on the top surface and the recess are connected to facilitate fluid flow.

In some embodiments, the microfluidic device includes a culture medium inlet for injecting a culture medium into the upper portion of a recess and a culture medium outlet for discharging the culture medium.

In some embodiments, the microfluidic device has a well shape.

In some embodiments, in the microfluidic device, two or more cavities are formed by an outer wall and a substrate, and the cavities are connected each other to facilitate fluid flow.

In some embodiments, a fluid patterning method includes using a microfluidic device described herein, which includes applying a patterning fluid to one position on an inner corner path; and performing patterning of the patterning fluid along the inner corner path and a microfluidic channel by capillary force.

In some embodiments, a microfluidic chip has a multi-well microfluidic device in which two or more microfluidic devices are formed on a common substrate and connected such that selective fluid flow is facilitated. In this case, there may be 4, 8, 16, 24, 48, 96 or 256 microfluidic device wells formed on one common substrate if necessary, but the embodiments are not limited thereto.

In some embodiments, a three-dimensional co-culture method for one or more among cells and tissue includes patterning a fluid including one or more among cells and tissue and providing a culture medium through a cavity using a microfluidic device described herein.

In accordance with some embodiments, a device includes a substrate having a top surface and a bottom surface opposite to the top surface; and one or more beams. A respective beam of the one or more beams has a bottom surface facing the top surface of the substrate and a top surface opposite to the bottom surface of the respective beam facing away from the top surface of the substrate. The respective beam is positioned adjacent to the substrate. At least a portion of the respective beam is spaced apart from the top surface of the substrate to define one or more microfluidic channels to enable movement of a fluid by capillary force between the bottom surface of the respective beam and the top surface of the substrate along the one or more microfluidic channels.

In accordance with some embodiments, a method of covering a substrate with a pattern of liquids includes flowing a liquid between the bottom surface of the respective beam of any device described herein and the top surface of the substrate of the device.

In accordance with some embodiments, a method includes, while a first liquid remains between the first linear portion of any device described herein as having a vertical divider defining a first chamber and the substrate, a second liquid remains between the second linear portion of the device and the substrate, and a third liquid remains between the third linear portion of the device and the substrate, providing a fourth liquid to the first chamber.

The "microfluidic channel" used herein refers to a path of fluid flow. In some cases, a fluid path defines a space in which cells or tissue is cultured and which is open at both sides to be connected with another flow path or chamber so as to allow exchange of a culture medium and a fluid between adjacent fluids or chambers.

The "cavity," "chamber" or "reservoir" refers to a space for containing a culture medium to culture cells or tissue. The "inner corner path" used herein refers to a path of fluid flow by capillary force as a boundary at which the inner surface of an outer wall meets a substrate.

The "culture medium channel" refers to a channel or flow path for providing a culture medium to cells from a chamber or reservoir containing a culture medium.

BRIEF DESCRIPTION OF THE DRAWINGS

For a better understanding of the various described embodiments, reference should be made to the Description of Embodiments below, in conjunction with the following drawings in which like reference numerals refer to corresponding parts throughout the figures.

FIG. 5 shows (a) the microfluidic devices connected to selectively move a fluid from a microfluidic device to another microfluidic device, (b) the microfluidic devices having a common supply path, and (c) the microfluidic devices having separate supply paths.

DETAILED DESCRIPTION

Reference will now be made to embodiments, examples of which are illustrated in the accompanying drawings. In the following description, numerous specific details are set forth in order to provide an understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

Figure 1:
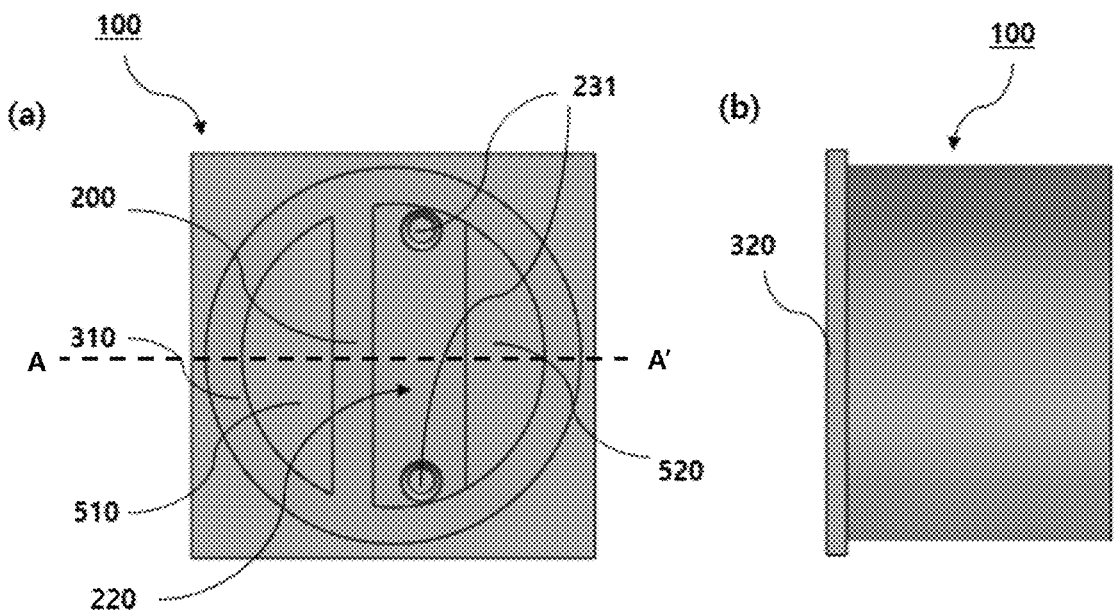
FIG. 1 depicts (a) a plan view and (b) a side view of a microfluidic device in accordance with some embodiments.

FIG. 1 depicts (a) a plan view and (b) a side view of a microfluidic device 100 in accordance with some embodiments. FIG. 1 shows line AA' represents a view from which the cross-section shown in FIG. 2 is taken.

Figure 2:
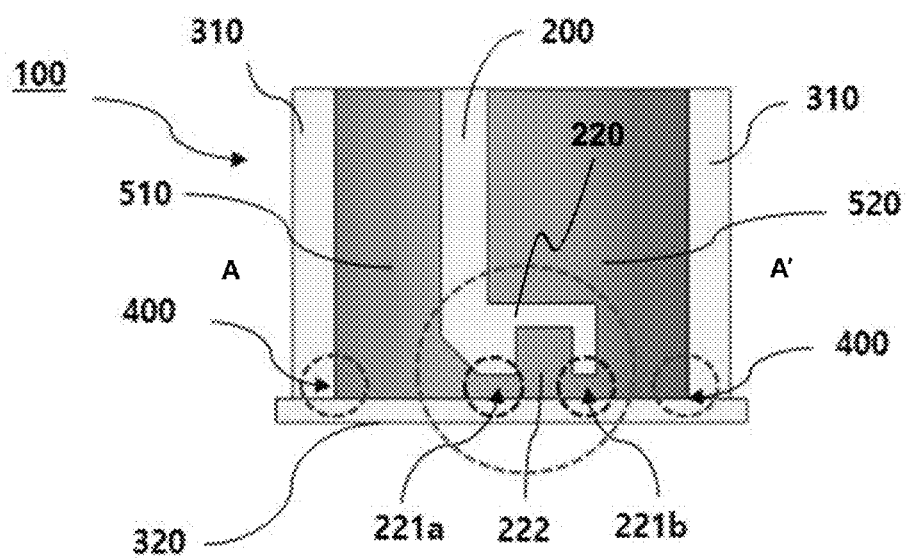
FIG. 2 is a cross-sectional view of the microfluidic device of FIG. 1.

FIGS. 1 and 2, the microfluidic device 100 includes a substrate 320, outer wall(s) 310, a cavity including chambers 510 and 520, and a microfluidic channel module 220, a partition 200, a microfluidic channel module 220 with one or more openings 231.

In some embodiments, the microfluidic device 100 is manufactured to overall have a hydrophilic surface on components. Alternatively, the microfluidic device 100 may be manufactured to have a hydrophilic surface at least in contact with a fluid.

The substrate 320 includes a top surface and a bottom surface, and preferably has a flat plate shape as shown in the illustrated examples.

Figure 5:
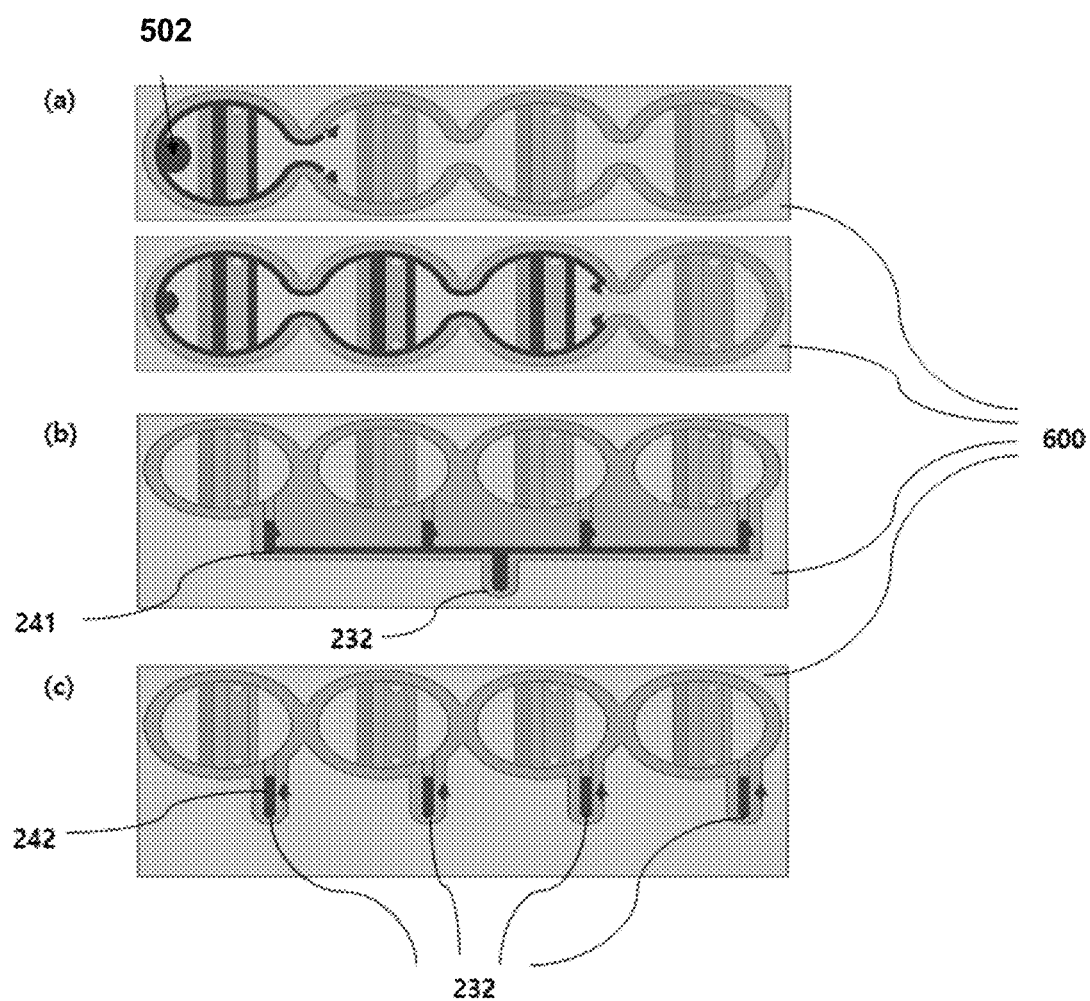
FIG. 5 illustrates four well-type microfluidic devices formed on a common substrate in accordance with some embodiments.

The outer wall 310 includes an inner surface facing a cavity to be described below and an outer surface opposite to the inner surface. In some embodiments, the outer wall has a cylindrical shape with an open top and bottom. However, the shape of the outer wall is not limited to the cylindrical shape with an open top and bottom, and the outer wall may have various shapes such as a hollow polygonal column or elliptical cylindrical shape. In some embodiments, the outer wall 310 has a shape in which a plurality of cylindrical shapes is connected and their sides are open to each other as shown in FIG. 5(*a*). In some embodiments, the outer wall 310 is manufactured in a shape such as a cylinder block including a plurality of cylinders as shown in FIG. 5(*b*) or 5(*c*).

In some embodiments, the outer walls 310 are attached, coupled, or bonded to (or integrated with) the top surface of the substrate 320, thereby forming a cavity with an open top with the substrate 320. There is no limit in the number of cavities formed with the outer walls 310 and the substrate 320. For example, as described with respect to FIGS. 1 and 2, one cavity may be formed, or as described with respect to FIG. 5, four cavities may be formed, or if necessary, 8, 16, 24, 48, 96 or 256 cavities may be formed. As described above, in FIG. 5(a), four cavities are connected to facilitate fluid flow.

When the outer wall 310 is attached, coupled, bonded to (or integrated with) the substrate 320, the boundary at which the inner surface of the outer wall 310 meets the top surface of the substrate 320 forms an inner corner path. For example, in FIGS. 1 and 2, the inner corner path may be a radius shape. In FIG. 5(a), the inner corner path has a shape in which four ellipses are connected. In FIGS. 5(b) and 5(c), the inner corner paths are formed with four separated ellipses.

In some embodiments, the microfluidic channel module 220 is disposed in each cavity. The microfluidic channel module 220 may have an elongated bar or long rod shape with top and bottom surfaces and both ends. In FIG. 1, one end of the microfluidic channel module 220 is attached to one position on the inner surface of the outer wall 310 and the other end is attached to another position on the inner surface of the outer wall 310, and therefore the microfluidic channel module may be disposed so as to cross the inside of the corresponding cavity.

In some embodiments, a part or all of the top surface of the microfluidic channel module 220 forms a partition 200 extending upward (that is, a direction of an opening to the cavity). In FIGS. 2 to 3, 7 and 9, the configuration includes a partition 200 in which a part of the top surface extends up to the top of the cavity. The partition 200 divides the cavity into the two chambers 510 and 520. Each chamber 510 or 520 may accommodate a different culture medium.

Meanwhile, when the microfluidic channel module 220 is disposed in a corresponding cavity, at least a part, preferably all, of the bottom surface of the microfluidic channel module 220 is disposed apart from the top surface of the substrate 320 forming a microfluidic channel (microfluidic flow path) facilitating fluid flow between the bottom surface and the top surface of the substrate 320 by capillary force. In some embodiments, by forming a recess, parallel to the microfluidic channel, on the bottom surface of the microfluidic channel module 220, a plurality of microfluidic channels with different heights is formed. For example, in FIG. 2, as one recess is formed in the bottom surface along a longitudinal direction of the microfluidic channel module 220, three microfluidic channels 221a, 221b and 222 with different heights are formed. However, the number and height of the microfluidic channels are not limited thereto, but may vary if necessary. That is, in some embodiments, the microfluidic device 100 includes n recesses and m protrusions on the bottom surface of the microfluidic channel module (where n is an integer number and m is an integer number). In some cases, n and m satisfy the following relationship m=n+1. In some cases, n and m satisfy the following relationship m=n. In some cases n and m satisfy the following relationship: m=n−1.

In FIG. 2, the microfluidic channels 221a, 221b and 222 may be filled with a fluid moved by capillary force, and have an open structure (e.g., sides of the microfluidic channels are not at least completely enclosed) in which the microfluidic channels are connected to facilitate fluid exchange with a fluid in an adjacent microfluidic channel or the chamber 510 or 520 and at both sides of the microfluidic channel (e.g., right and left sides of 221a of FIG. 2). Therefore, the microfluidic channel of the microfluidic device manufactured as described in this application may be open (in that the microfluidic channel has no or partial side walls), reversible, and transient.

Figure 10:
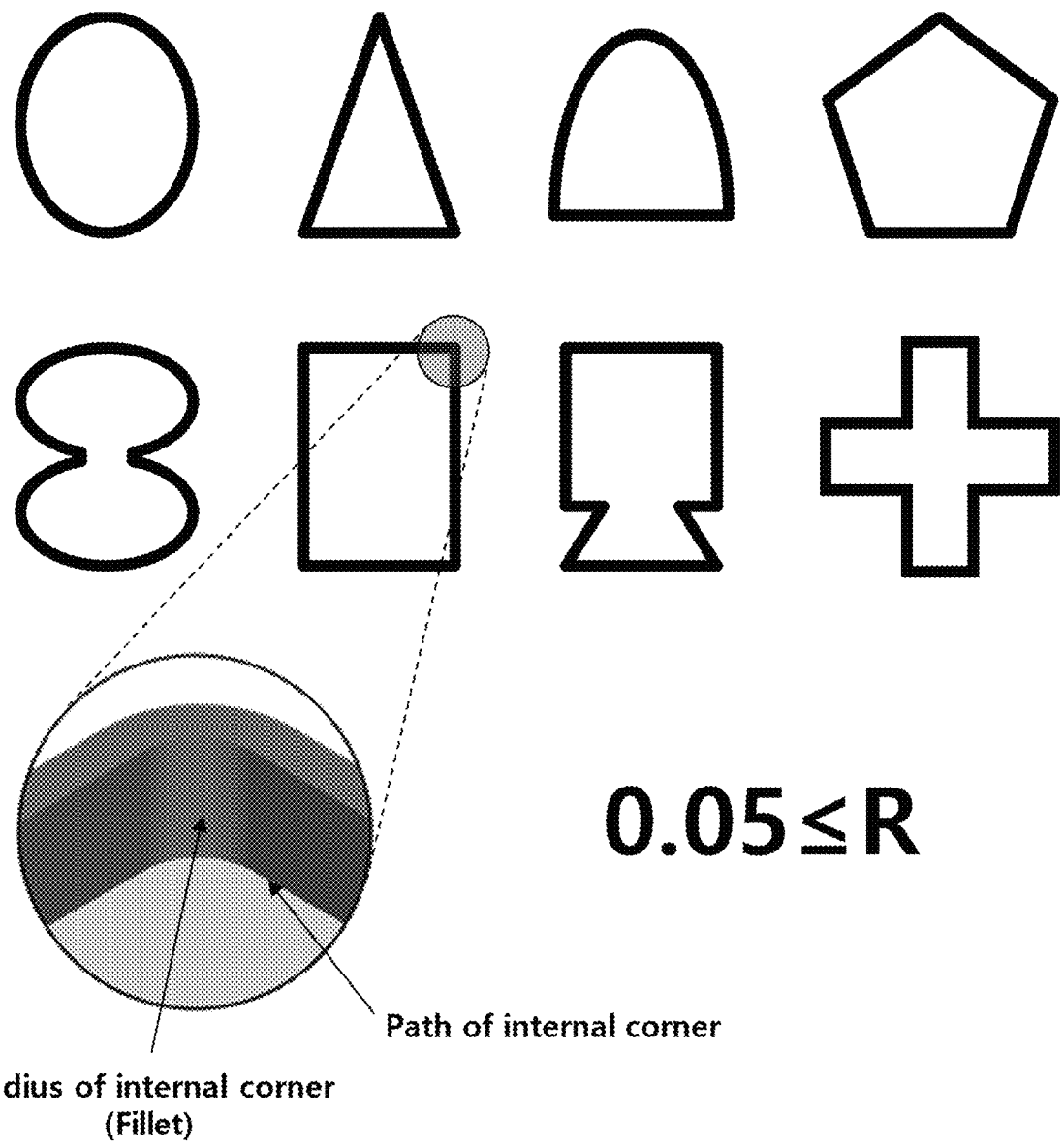
FIG. 10 shows various types of inner corner paths in accordance with some embodiments.

In addition, the inner corner path 340 may have a circular, elliptical, polygonal or atypical shape (e.g., FIG. 10). When the inner corner path 340 has a polygonal shape, since the inner corner paths have to be tangentially connected to perform continuous patterning of a fluid, a fillet having a radius (R) value of 0.05 mm or more may be preferably included at an outer wall corner corresponding to the part at which polygonal sides meet with each other.

The microfluidic device may be manufactured of an engineering plastic so as to have a contact angle of 90 degrees or less (based on distilled water (DW)).

Meanwhile, to provide a fluid into the microfluidic channel, for example, the microfluidic channel 222, or discharge a fluid from the microfluidic channel, in the top surface of the microfluidic channel module 220, one or more openings 231 may be formed by passing from the top surface to the corresponding microfluidic channel. Preferably, for example, as in the exemplary embodiment shown in FIG. 1, to provide a fluid into the microfluidic channel 222 formed by a recess or discharge a fluid therefrom, an opening 231 may be formed at each end of the microfluidic channel module 220 in the top surface corresponding to the vertically upper side of the microfluidic channel 222. With this configuration, the microfluidic channel 222 is connected to facilitate fluid flow with the chamber 520 through the opening 231.

In some embodiments, the inner diameter of the outer wall 310 is at least 3 mm, at least 4 mm, at least 5 mm, at least 6 mm, at least 7 mm, at least 8 mm, at least 9 mm, at least 10 mm, at least 11 mm, at least 12 mm, at least 13 mm, at least 14 mm, or at least 15 mm. In some embodiments, the inner diameter of the outer wall 310 is at most 3 mm, at most 4 mm, at most 5 mm, at most 6 mm, at most 7 mm, at most 8 mm, at most 9 mm, at most 10 mm, at most 11 mm, at most 12 mm, at most 13 mm, at most 14 mm, or at most 15 mm.

In some embodiments, the microfluidic channels 221a and the microfluidic channels 221b have a height of at least 0.05 mm, at least 0.06 mm, at least 0.07 mm, at least 0.08 mm, at least 0.09 mm, at least 0.1 mm, at least 0.11 mm, at least 0.12 mm, at least 0.13 mm, at least 0.14 mm, at least 0.15 mm, at least 0.16 mm, at least 0.17 mm, at least 0.18 mm, at least 0.19 mm, or at least 0.20 mm. In some embodiments, the microfluidic channels 221a and the microfluidic channels 221b have a height of at most 0.05 mm, at most 0.06 mm, at most 0.07 mm, at most 0.08 mm, at most 0.09 mm, at most 0.1 mm, at most 0.11 mm, at most 0.12 mm, at most 0.13 mm, at most 0.14 mm, at most 0.15 mm, at most 0.16 mm, at most 0.17 mm, at most 0.18 mm, at most 0.19 mm, or at most 0.20 mm.

In some embodiments, the microfluidic channels 221a and the microfluidic channels 221b have a width of at least 0.5 mm, at least 0.6 mm, at least 0.7 mm, at least 0.8 mm, at least 0.9 mm, at least 1.0 mm, at least 1.1 mm, at least 1.2 mm, at least 1.3 mm, at least 1.4 mm, at least 1.5 mm, at least 1.6 mm, at least 1.7 mm, at least 1.8 mm, at least 1.9 mm, or at least 2.0 mm. In some embodiments, the microfluidic channels 221a and the microfluidic channels 221b have a width of at most 0.5 mm, at most 0.6 mm, at most 0.7 mm, at most 0.8 mm, at most 0.9 mm, at most 1.0 mm, at most 1.1 mm, at most 1.2 mm, at most 1.3 mm, at most 1.4 mm, at most 1.5 mm, at most 1.6 mm, at most 1.7 mm, at most 1.8 mm, at most 1.9 mm, or at most 2.0 mm.

In some embodiments, the microfluidic channel 222 has a height of at least 0.05 mm, at least 0.1 mm, at least 0.2 mm, at least 0.3 mm, at least 0.4 mm, at least 0.5 mm, at least 0.6 mm, at least 0.7 mm, at least 0.8 mm, at least 0.9 mm, at least 1.0 mm, at least 1.1 mm, at least 1.2 mm, at least 1.3 mm, at least 1.4 mm, at least 1.5 mm, at least 1.6 mm, at least 1.7 mm, at least 1.8 mm, at least 1.9 mm, at least 2.0 mm, at least 2.1 mm, at least 2.2 mm, at least 2.3 mm, at least 2.4 mm, or at least 2.5 mm. In some embodiments, the microfluidic channel 222 has a height of at most 0.05 mm, at most 0.1 mm, at most 0.2 mm, at most 0.3 mm, at most 0.4 mm, at most 0.5 mm, at most 0.6 mm, at most 0.7 mm, at most 0.8 mm, at most 0.9 mm, at most 1.0 mm, at most 1.1 mm, at most 1.2 mm, at most 1.3 mm, at most 1.4 mm, at most 1.5 mm, at most 1.6 mm, at most 1.7 mm, at most 1.8 mm, at most 1.9 mm, at most 2.0 mm, at most 2.1 mm, at most 2.2 mm, at most 2.3 mm, at most 2.4 mm, or at most 2.5 mm.

In some embodiments, the microfluidic channel 222 has a width of at least 0.5 mm, at least 0.6 mm, at least 0.7 mm, at least 0.8 mm, at least 0.9 mm, at least 1.0 mm, at least 1.1 mm, at least 1.2 mm, at least 1.3 mm, at least 1.4 mm, at least 1.5 mm, at least 1.6 mm, at least 1.7 mm, at least 1.8 mm, at least 1.9 mm, or at least 2.0 mm. In some embodiments, the microfluidic channel 222 has a width of at most 0.5 mm, at most 0.6 mm, at most 0.7 mm, at most 0.8 mm, at most 0.9 mm, at most 1.0 mm, at most 1.1 mm, at most 1.2 mm, at most 1.3 mm, at most 1.4 mm, at most 1.5 mm, at most 1.6 mm, at most 1.7 mm, at most 1.8 mm, at most 1.9 mm, or at most 2.0 mm.

Figure 3:
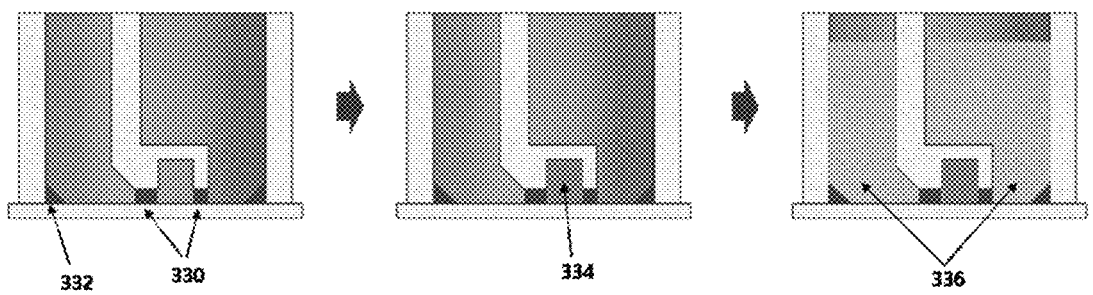
FIG. 3 is a schematic diagram illustrating a fluid patterning process using the microfluidic device in accordance with some embodiments.
Figure 3:
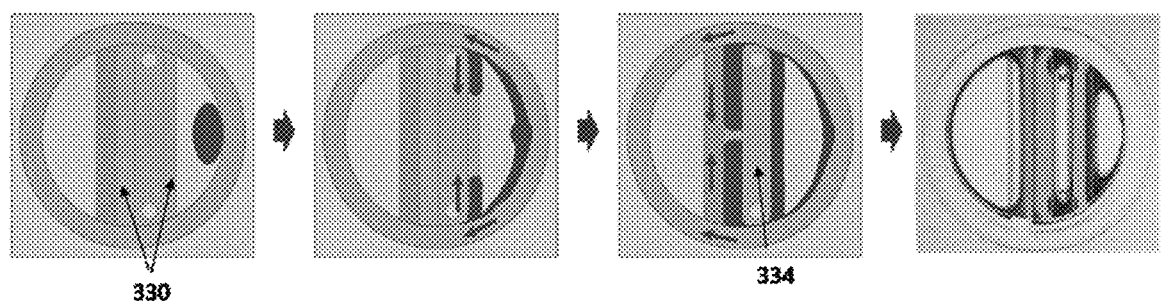
Figure 3:
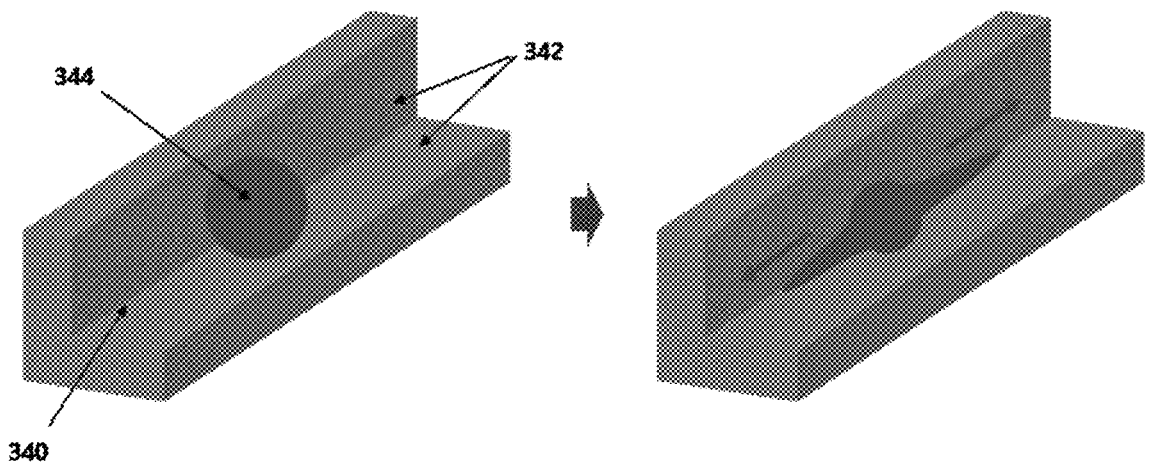

FIG. 3 is a schematic diagram illustrating a fluid patterning method in accordance with some embodiments. First, for first patterning, a first fluid 344 is provided to an arbitrary part on the inner corner path 340 (e.g., shown in FIG. 2) in the second chamber 520. As shown in FIG. 3, section c, a droplet of first fluid 344 provided on hydrophilic surface adjacent to the inner corner path 340 spreads along the inner corner path 340. In some embodiments, the provided fluid 344 flows in both directions along the inner corner path by capillary force (e.g., the provided fluid 344 spreads along the inner corner path to form a spread fluid 332 (e.g., FIG. 3, section b), which continuously flows along the microfluidic channels 221b and 221a as fluids 330, and then sequentially patterns along the inner corner path 340 of the first chamber 510). Afterward, when a second fluid 334 for second patterning is injected through the opening 231, the microfluidic channel 222 formed by the recess is patterned or filled with the second fluid 334 (e.g., FIG. 3, section a). In some embodiments, a culture medium 336 is injected into each of the chambers 510 and 520 (e.g., FIG. 3, section a).

Figure 4:
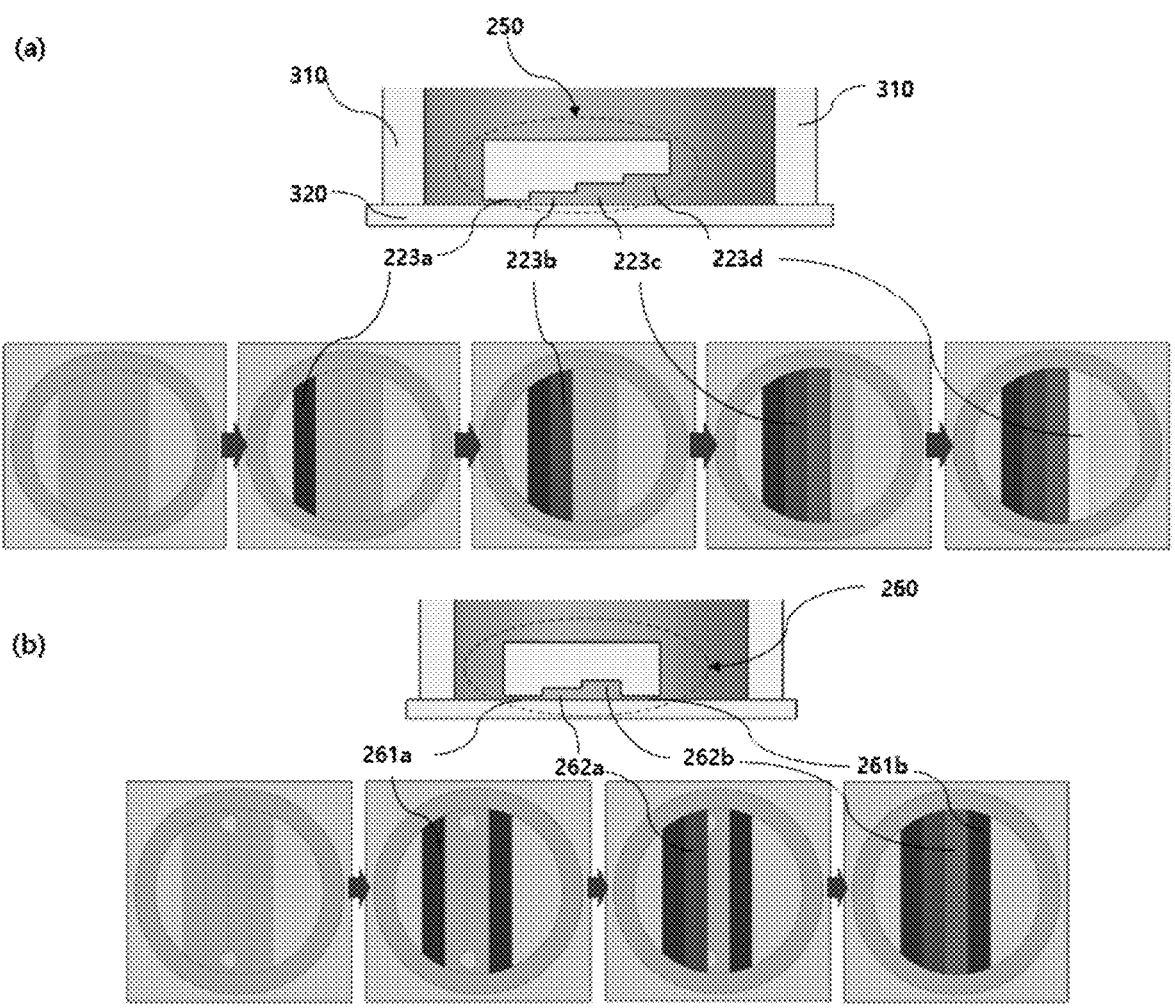
FIG. 4 illustrates (a) a microfluidic device including a step-like microfluidic channel in accordance with some embodiments and fluid patterning using the same and (b) a microfluidic device having a structure in which adjacent microfluidic channels have different heights in accordance with some embodiments and fluid patterning using the same.

FIG. 4 illustrates microfluidic channel modules 250 and 260 in accordance with some embodiments. In FIG. 4(a), four microfluidic channels 223a, 223b, 223c and 223d are formed to have sequentially increased heights by sequentially including step-like protrusions with different heights on the bottom surface of the microfluidic channel module 250. In the exemplary embodiment shown in FIG. 4(b), recesses 262a and 262b with different depths are sequentially formed in a step shape with different heights on the bottom surface of the microfluidic channel module 260.

As shown in FIG. 4(a), when the microfluidic channels 223a, 223b, 223c and 223d with different heights are adjacent to each other, a fluid may be sequentially patterned from the microfluidic channel 223a with the lowest height to a microfluidic channel with a higher height. While the difference in height of the microfluidic channels may vary according to purpose, the microfluidic channels are preferably formed to have a difference in height of 0.05 mm or more, and the highest microfluidic channel preferably has a height of 1 mm or less.

As the microfluidic channels are formed as shown in FIG. 4(b), the microfluidic channels 261a and 261b with the lowest height are included at the left and right sides of the drawing, and two microfluidic channels 262a and 262b with higher heights are sequentially disposed between them. In this configuration, the microfluidic channels 261a and 261b with the lowest height are first patterned at the left and right sides, and a fluid is injected through an opening (not shown in FIG. 4) located in the top surface of the microfluidic channel module 220, resulting in the patterning of the microfluidic channels 262a and 262b. The microfluidic channels 261a and 261b may have the lowest height of 500 μm or less, but are not limited thereto, and the microfluidic channels may have various heights according to purpose or necessity.

FIG. 5 illustrates two or more microfluidic devices 100 implemented on one common substrate 600 in accordance with some embodiments.

In the exemplary embodiment shown in FIG. 5(a), the outer walls of the microfluidic devices are configured such that cavities of the microfluidic devices are connected to facilitate fluid flow between the cavities. In this configuration, since inner corner paths are connected such that a fluid can flow between the cavities, a fluid may be provided to an arbitrary position on an inner corner path of an arbitrary microfluidic device, and yet the fluid can flow to multiple cavities by capillary force and pattern microfluidic channels in the multiple cavities.

In FIGS. 5(b) and 5(c), cavities of the microfluidic device are not connected. In such configurations, the microfluidic devices may be patterned separately by fluid inlets 232 and fluid injection paths 242, which are separately formed (e.g., as shown in FIG. 5(c)), or patterned at one time by one fluid inlet 232 and a branched fluid injection path 241 (e.g., as shown in FIG. 5(b)). Each microfluidic device may be manufactured as a well type.

Figure 6:
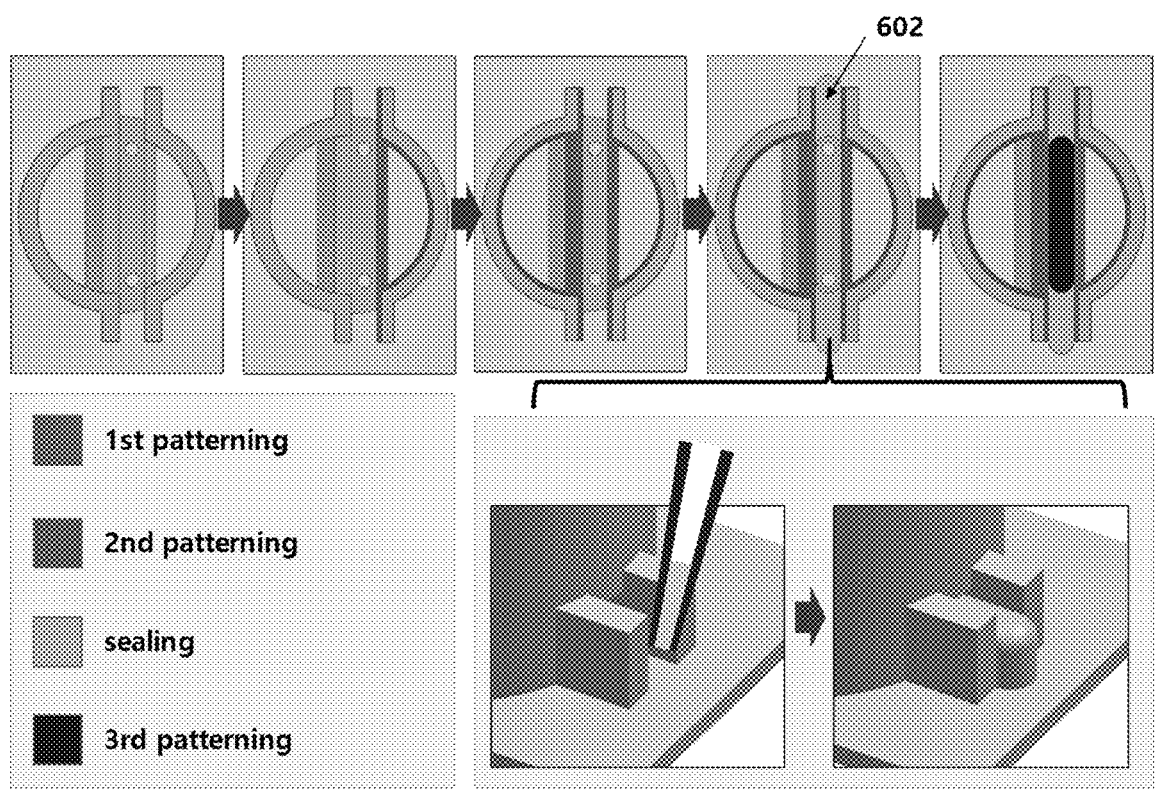
FIG. 6 schematically illustrates the structure of a stopper of the microfluidic device and a process of stopper sealing in accordance with some embodiments.
Figure 7:
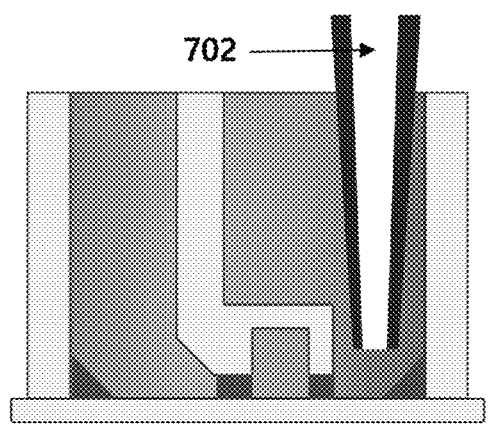
FIG. 7 is a schematic diagram illustrating that patterning areas and thicknesses are adjusted by adjusting the amount of a fluid applied to a microfluidic device in accordance with some embodiments.
Figure 7:
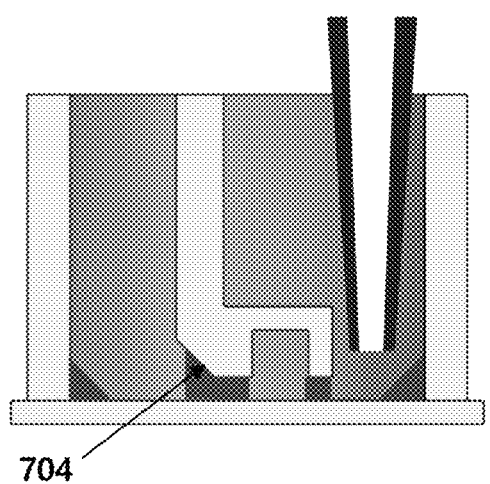
Figure 7:
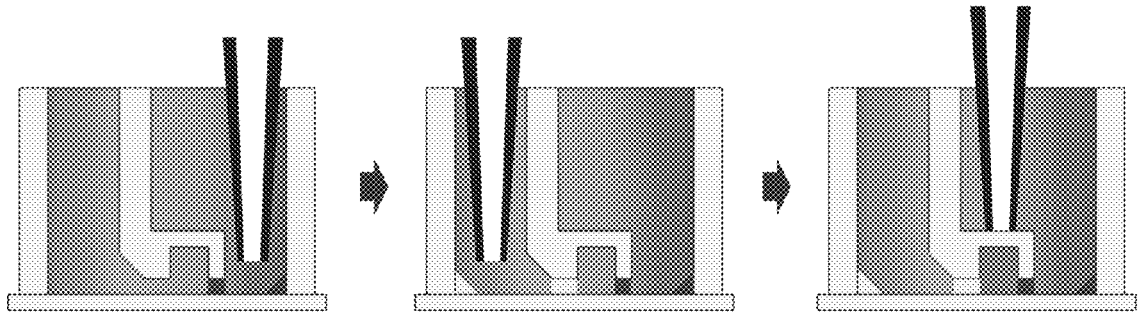

Referring to FIG. 6, in the microfluidic device 100 which has the first chamber 510 and the second chamber 520 divided by the partition 200 extending upward in the microfluidic channel module 220, a stopper portion 602 is included to prevent fluid flow between the first chamber 510 and the second chamber 520. The stopper portion 602 includes a hollow structure for stopping fluid patterning through the inner corner path 340. Applying a sealant (e.g., a gel) to the stopper portion 602 prevents the fluid flow between the microfluidic channel in the first chamber 510 and the microfluidic channel in the second chamber 520. In some embodiments, for additional patterning by blocking both open sides of a microfluidic channel, a curable (e.g., post-curable) material such as a gel is used for patterning.

Various types of fluid patterning may be performed using the microfluidic device 100 described herein. A fluid on the hydrophilic surface changes its shape and flows along the contact surface due to capillary force, and moves without a separate external force until the capillary force is in equilibrium. A patterning (edge-guided patterning; EGP) method through the inner corner path 340 of the microfluidic device 100 allows fluid flow along an inner corner having a right angle, acute angle or obtuse angle using such capillary force (FIG. 3(c)). In some embodiments, the EGP method provides a means capable of patterning a fluid at one time (refer to FIG. 3(b)). Specifically, a fluid provided at an arbitrary position on the inner corner path 340 of the microfluidic device 100 moves along the hydrophilic surface due to capillary force, and further moves to the microfluidic channel 221b by a stronger capillary force caused by the microfluidic channel 221b at both ends thereof, thereby patterning a microfluidic channel with open sides. In addition, the fluid flowing to the microfluidic channel 221b further moves by a different inner corner path connected to the microfluidic channel 221b. According to such a method, desired fluid patterning may be realized through a single injection of a fluid.

In some embodiments, patterning may be performed step-by-step or the position and form of patterning may be controlled by adjusting an amount of the fluid provided for patterning (e.g., using a pipette 702). This is useful when precise adjustment of patterning thickness or width of a polymeric material serving as a cellular or extracellular matrix is needed. When an excessive amount of a fluid is injected, the fluid remaining after filling all flow paths further moves to a direction of a stronger capillary force, such that the thickness or width of a specific area increases. In some embodiments, as shown in FIG. 7(a), at least one edge in the bottom surface of a microfluidic channel module constituting a microfluidic channel is obliquely cut by a process such as chamfering. In such embodiments, when an excessive amount of a fluid is provided as shown in FIG. 7(b), the fluid flows along the oblique side. When a smaller amount of a fluid is injected as shown in FIG. 7(c), only some of the flow paths may be patterned with the fluid moving to a direction of a strong capillary force. This allows a subsequent provision of a different liquid to pattern one or more remaining flow paths.

Figure 8:
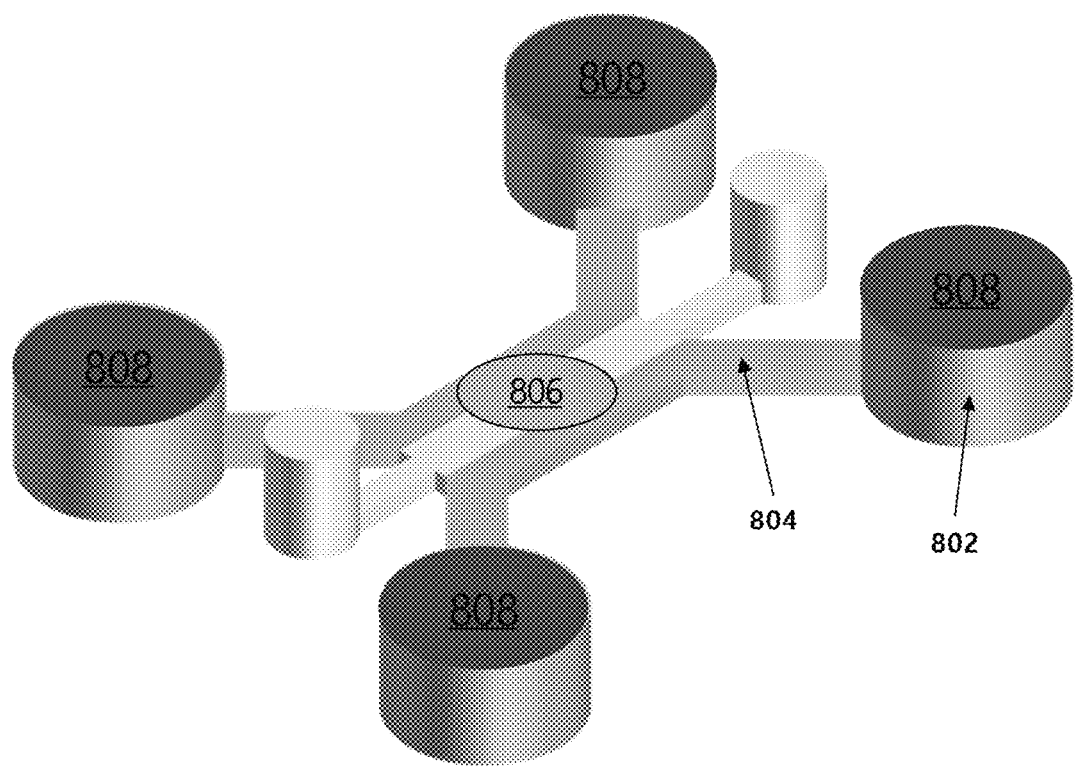
FIG. 8 is a set of diagrams comparing (a) a microfluidic device according to the conventional art and (b) a microfluidic device having an open-type microfluidic channel embedded in a chamber in accordance with some embodiments.
Figure 8:
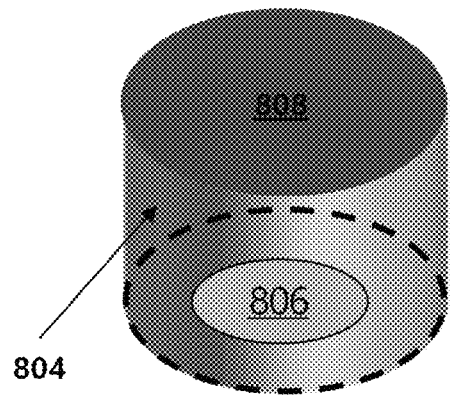

FIG. 8 is a set of diagrams comparing (a) a microfluidic device according to the conventional art and (b) a microfluidic device in accordance with some embodiments. While the conventional microfluidic device has separate reservoirs 802 providing fluid 804 (e.g., culture medium) through microfluidic channels to cell location 806 (thus multiple reservoirs are exposed to air), the microfluidic device in accordance with some embodiments has a single-well shape, which includes at least partially open microfluidic channels.

Figure 9:
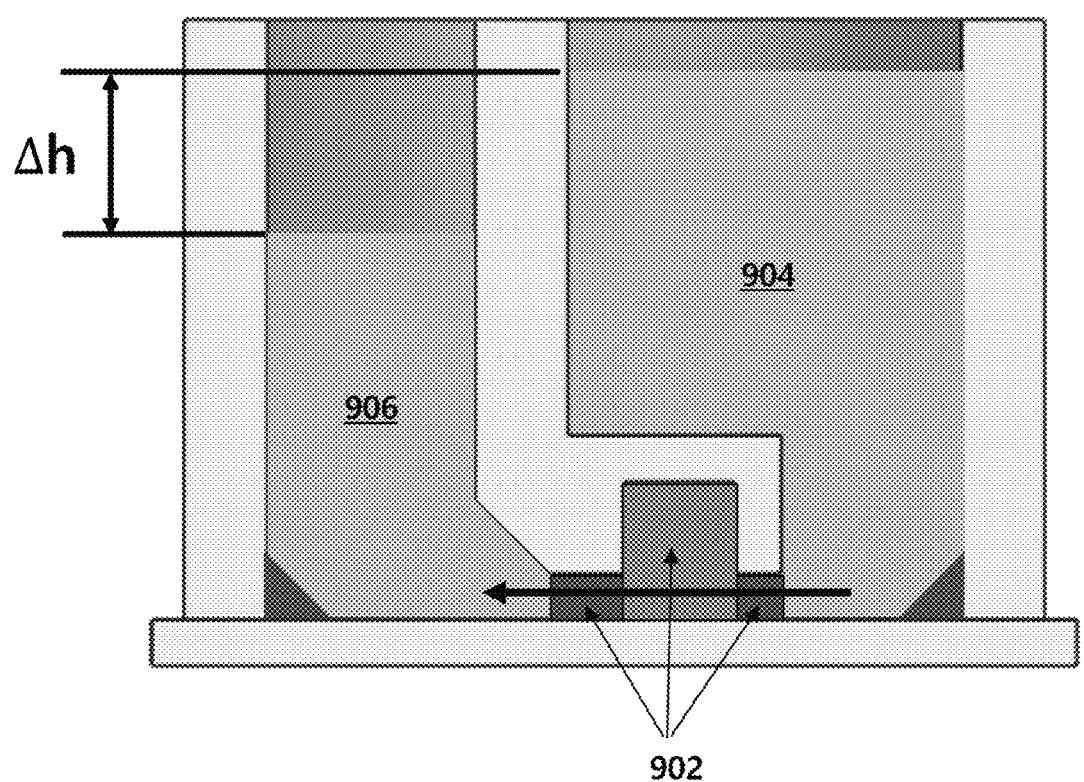
FIG. 9 shows the direction of fluid flow allowed by an open-type microfluidic channel after two chambers divided by a partition are filled with a culture medium at different heights.

FIG. 9 shows the direction of fluid flow allowed by an open-type microfluidic channel after two chambers divided by a partition are filled with liquids. In some embodiments, the microfluidic channels are filled with liquid-permeable material. In some embodiments, the first chamber is filled with a first liquid 904 and the second chamber is filled with a second liquid 906 that is distinct from the first liquid. In some embodiments, the first chamber and the second chamber are filled with a same liquid. In some embodiments, the first chamber is filled with a liquid of a first height and the second chamber is filled with a liquid of a second height. In some embodiments, the gravitational force (and a pressure associated with it) causes flow of liquid from one chamber to the other chamber (e.g., from a chamber having a liquid with a greater height to a chamber having a liquid with a lower height, such as from the first chamber filled with the first liquid 904 to the second chamber filled with the second liquid 906). In some embodiments, the liquid flows between the chambers through other mechanisms (e.g., osmosis, etc.).

Figure 11:
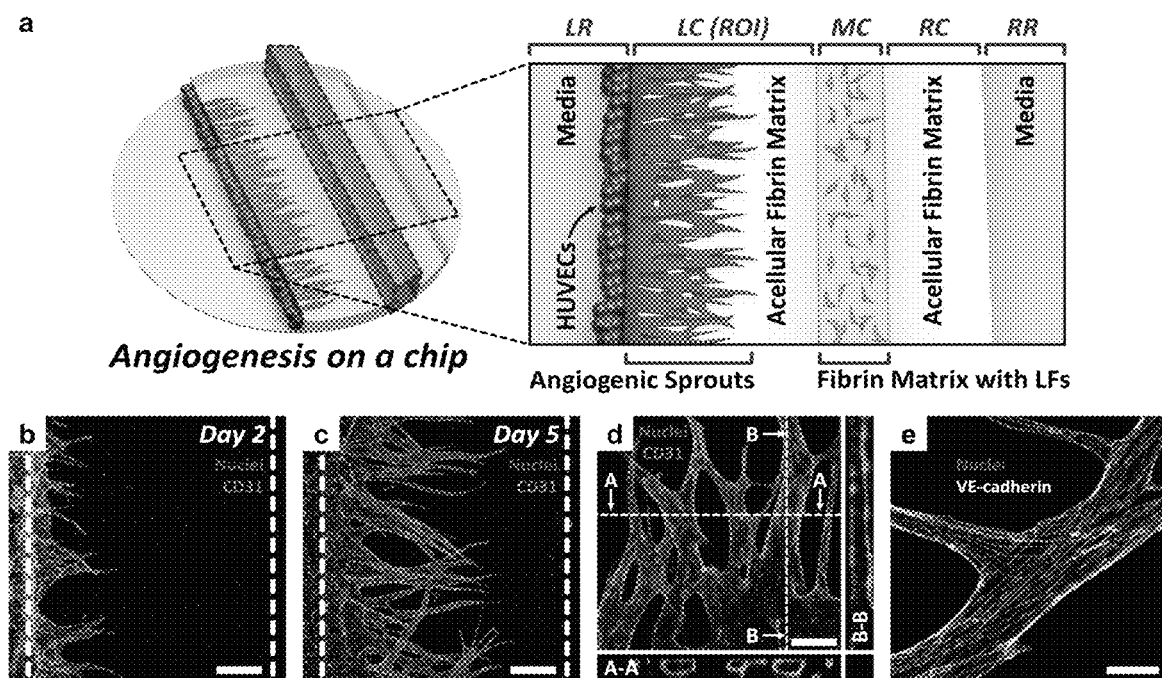
FIG. 11 shows an angiogenesis experiment performed using a device described herein.

FIG. 11 illustrates an angiogenesis experiment performed using a device described herein. (a) Cell-seeding configuration for the angiogenesis experiment. From left to right: human umbilical vein endothelial cells (HUVECs) attached on the left side of the acellular fibrin matrix in the left channel (LC, h=100 μm). Lung fibroblasts (LFs) mixed in fibrin are patterned in the middle channel (MC). Acellular fibrin in the right channel (RC). (b) Fluorescence image of the angiogenic sprout at Day 2 showing endothelial tip cells invading towards the LF channel. Boundaries of the LC acellular matrix are denoted by the dotted lines. Scale bar=200 μm. (c) Fluorescence micrograph at Day 5 show that EC sprouts invaded about 700 μm. Scale bar=200 μm. (d) Confocal cross section image of the sprouts after Day 5 clearing showing open lumen. Scale bar=100 μm. (e) vascular endothelial (VE)-cadherin immunostained image confirms the strong expression of tight junction protein VE-cadherin in the vessels. Scale bar=50 μm.

Figure 13:
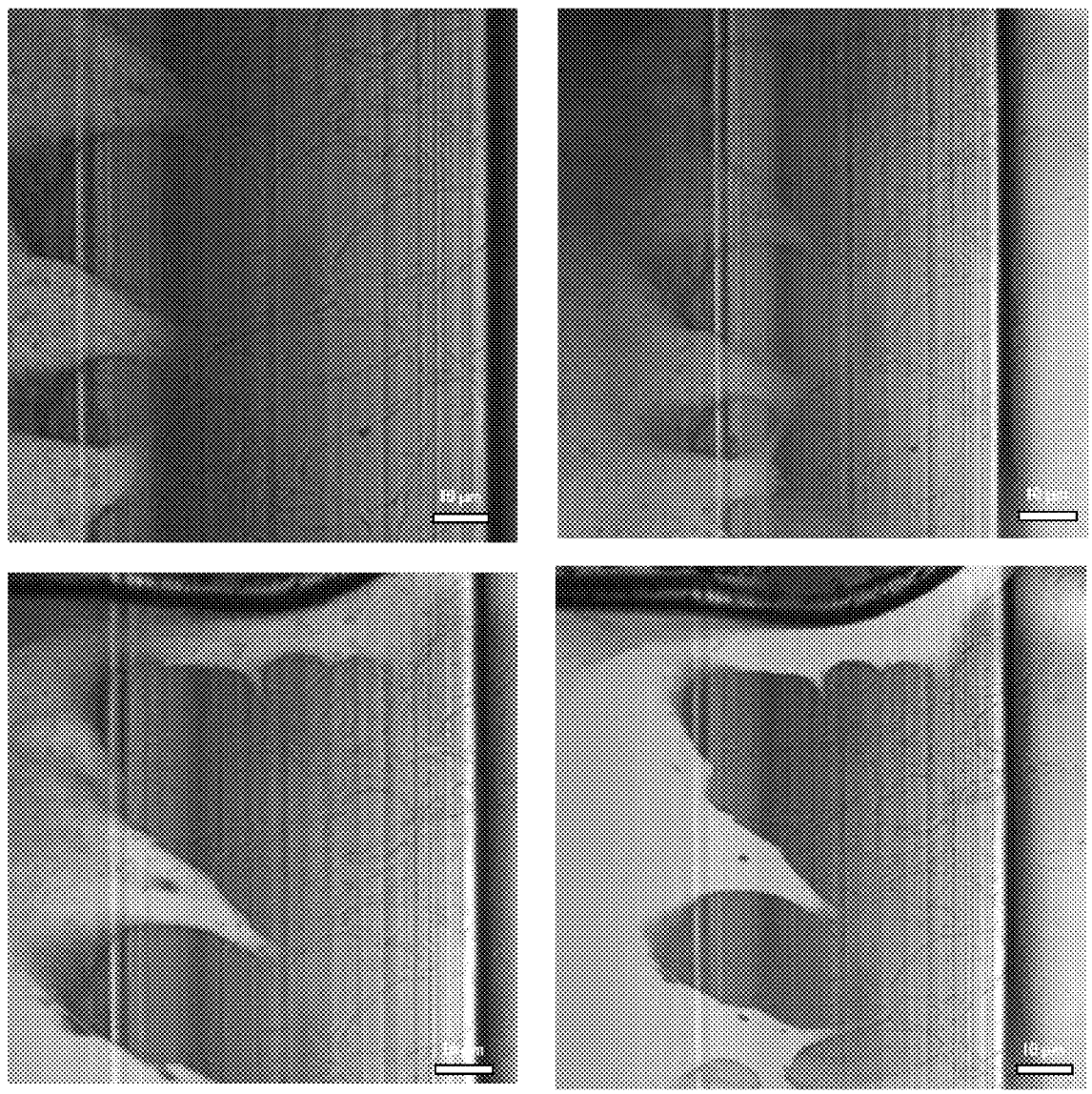
FIG. 13 shows example perfusability test images obtained using a device described herein.

In obtaining the results shown in FIG. 13, the following steps were taken.

Cell Preparation

HUVECs (Lonza) were cultured in endothelial growth medium 2 (EGM-2, Lonze). LF (Lonza) were cultured in fibroblast growth medium 2 (FGM-2, Lonza). The cells were incubated at 37° C. in 5% CO2 for three days prior to loading in the devices. Cultured LFs and HUVECs are removed from the culture dish using 0.25% Trypsin-EDTA (Hyclone). LFs are then re-suspended in a bovine fibrinogen solution at a cell concentration of 5×106 cells ml-1 and HUVECs are re-suspended at a concentration of 7×106 cells ml-1 in EGM-2.

Cell Seeding in the Device

Before starting the cell seeding, the hydrophilicity of the inner surface of the device was improved by 1 minute of plasma treatment (Cute, Femto Science, Korea) with a power of 50 W. To avoid degradation of hydrophilicity, liquid solution patterning was started without exceeding 30 minutes after plasma treatment. Immediately after mixing the cell-free fibrinogen solution with thrombin (0.5 U/ml, Sigma), one of the inner wedges formed by the bottom and side walls of the device was selected and dropped by 3 μl. A small amount of liquid moves along the hydrophilic wedge centered on the dropping position, and the remaining two channels (depth: 100 μm) except for the middle channel (MC) are filled, and they are left at room temperature for 4 minutes and clotted. As a result, the MC becomes a closed channel with only two holes at both ends, creating a situation where a new liquid can be loaded. Immediately after mixing thrombin (0.5 U/ml) with the fibrinogen solution containing LFs (cell concentration of 5×106 cells ml-1), the MC was filled with a pipette. After a 3-minute waiting period, a total of 200 μl of EGM-2 medium was loaded onto two reservoirs in semicircular form after the polymerization was completed. For fixation of LFs in the fibrin matrix, the device was incubated for 18 hours at 37° C. and 5% CO2. After the medium in the medium reservoir was removed, 20 μl of EGM-2 solution (cell concentration 5×106 cells ml-1) containing HUVECs prepared in advance was loaded into left reservoir (LR). To attach the HUVECs to the fibrin matrix lateral surface using gravity, the device was incubated in the incubator for 30 minutes at an angle of 90 degrees. Then, the entire reservoir of the device was filled with EGM-2 and stored in an incubator. After 3 days from the start of co-culture, the medium was replaced with fresh EGM-2.

Immunostaining

Co-cultured tissues in the device were fixed with 5% (w/v) paraformaldehyde (Biosesang) in PBS (Gibco) for 15 minutes, followed by permeabilization with a 20 minutes immersion in 0.15% Triton X-100 (Sigma). Samples were then treated with a 1-hour immersion in 3% BSA (Sigma) to prevent nonspecific antibody binding. Fluorescence-conjugated monoclonal mouse anti-human VE-cadherin (eBioscience) and anti-human CD31 (BioLegend) primary antibody dyes were prepared in a 1:200 dilution and applied to the tissue samples overnight at 4° C. DNA staining was done with a 1:1000 dilution of Hoechst 3342 (Molecular Probes) for 1 hour at room temperature. Imaging was done via confocal microscopy (Olympus FV1000) at 10× and 20× to produce a three-dimensional renderable projection of the angiogenic sprouts.

Figure 12:
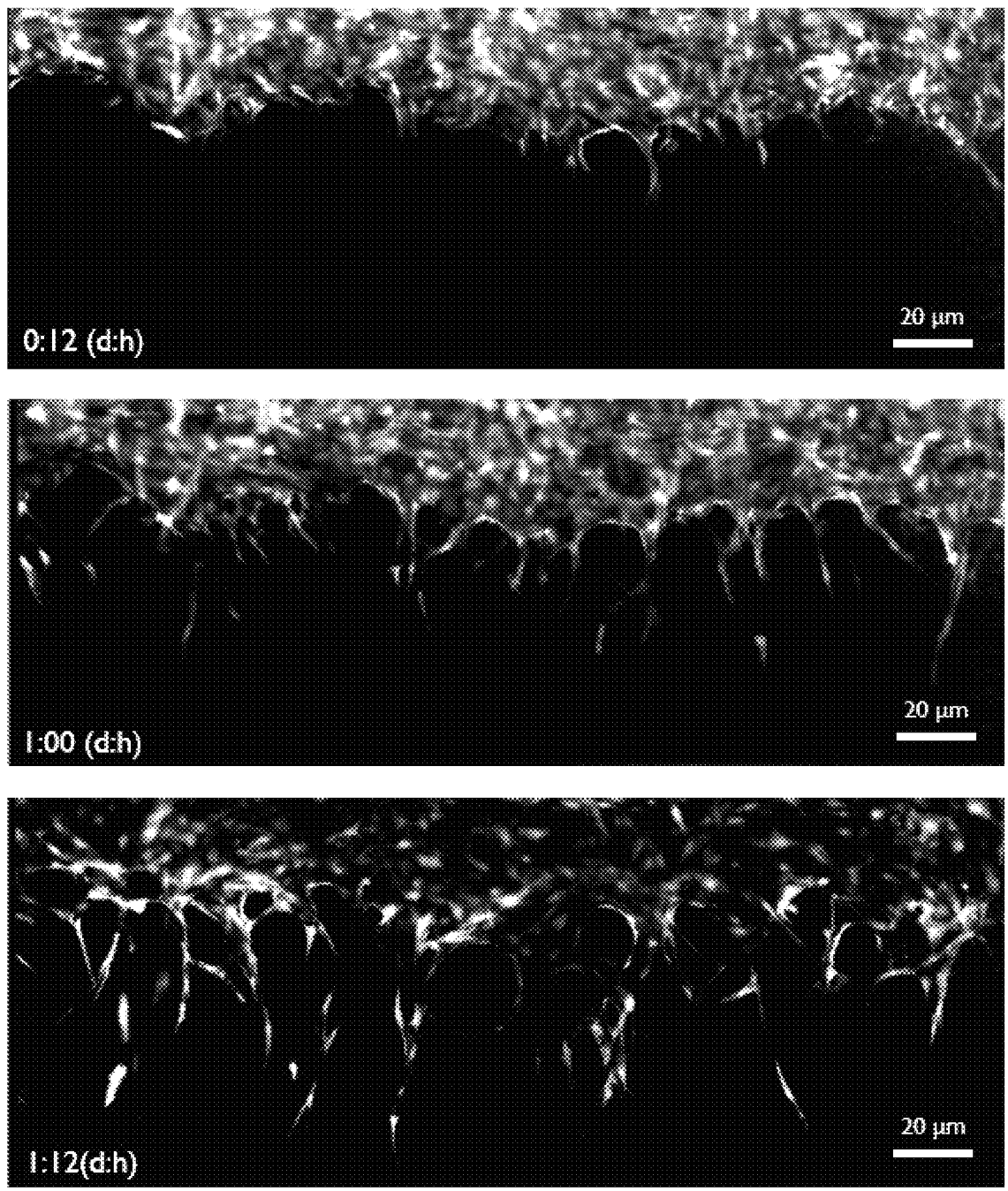
FIG. 12 shows example time-lapse fluorescence images of angiogenesis obtained using a device described herein.

FIG. 12 shows example time-lapse fluorescence images of angiogenesis obtained using a device described herein.

FIG. 13 shows example perfusability test images obtained using a device described herein. Perfusable vessel was verified by flowing FITC-dextran dye from one side of channel.

Figure 14:
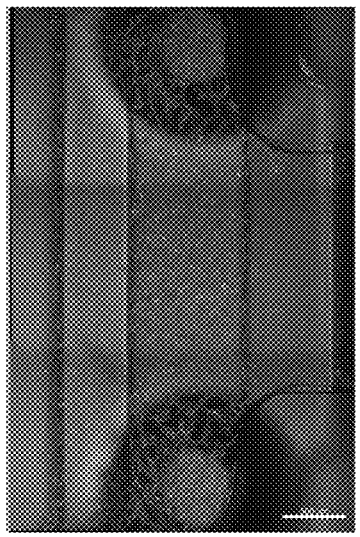
FIG. 14 shows example lymphangiovasculogenesis obtained using a device described herein.
Figure 14:
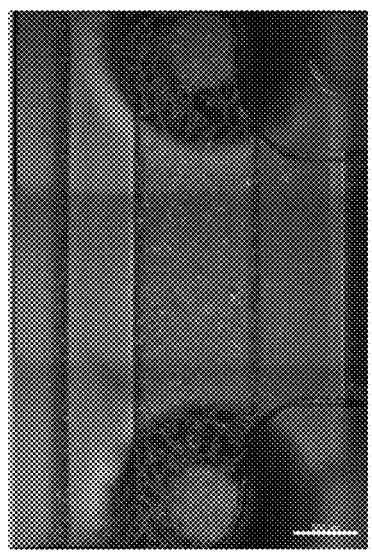
Figure 14:
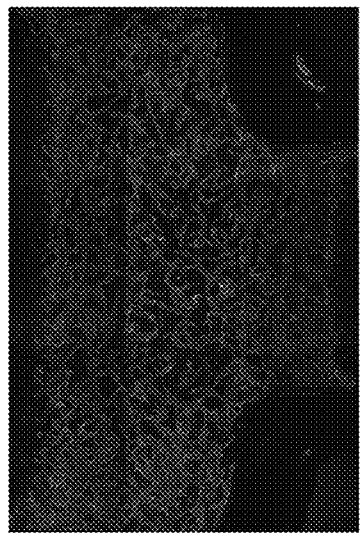
Figure 14:
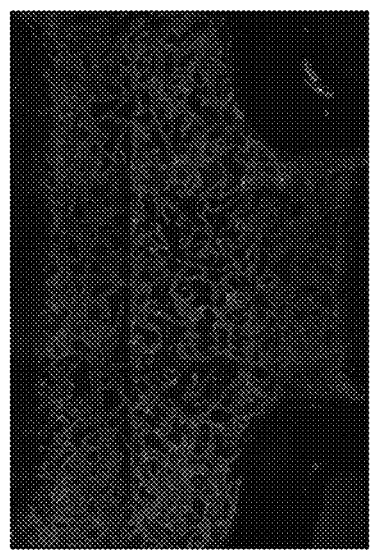
Figure 14:
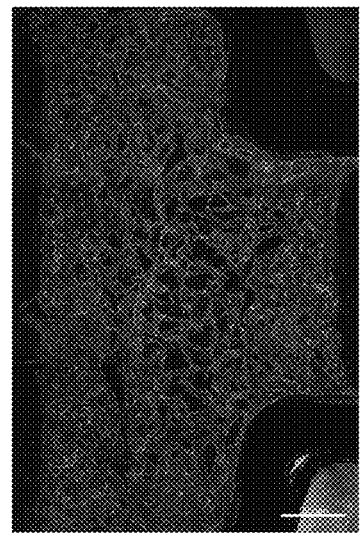
Figure 14:
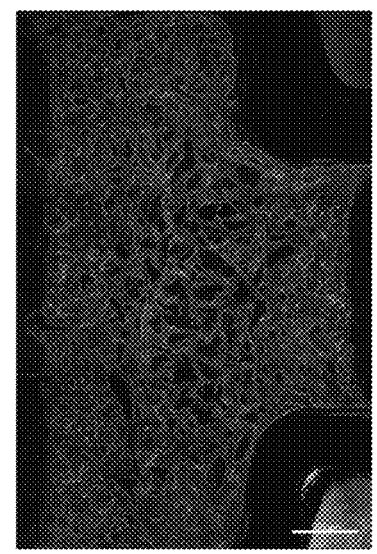

FIG. 14 example lymphangiovasculogenesis obtained using a device described herein. Lymphangiovasculogenesis is formation of network by lymphatic endothelial cells (LECs).

Figure 15:
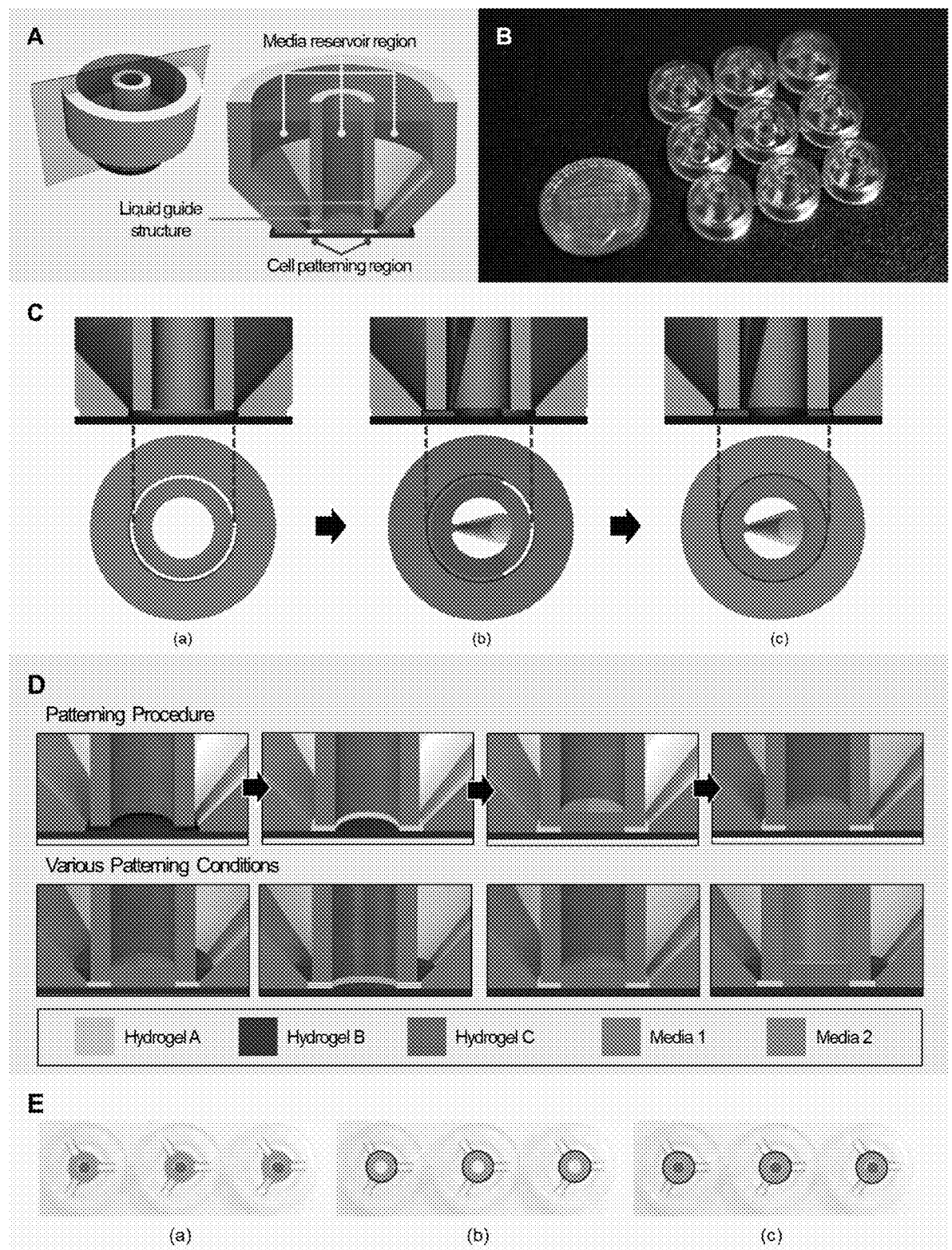
FIG. 15 illustrates a microfluidic device in accordance with some embodiments.

FIG. 15 illustrates a microfluidic device in accordance with some embodiments.

The microfluidic device shown in FIG. 15 has a hollow structure where a hollow center of the structure is facing toward the substrate.

In some embodiments, the microfluidic device shown in FIG. 15 is made by injection molding.

In some embodiments, the hollow structure has a round cross-section (e.g., having a shape of a donut or a circle).

FIG. 15(A) shows the structure of the microfluidic device, which has a round shape. The microfluidic device is divided into cell patterning parts and media reservoir areas.

FIG. 15(B) shows a photograph of a device manufactured by injection molding.

FIG. 15(C) shows that the device is treated to have hydrophilic surfaces. The hydrogel patterning is carried out by a droplet of hydrogel on a surface, where the hydrogel is spontaneously drawn under the structure that acts as a "liquid guide" (e.g., by capillary force).

FIG. 15(D) shows that the device accommodates more than one hydrogel and media in some embodiments.

FIG. 15(E) shows images of an actual microfluidic device, viewed from the bottom through the patterning operations.

Figure 16:
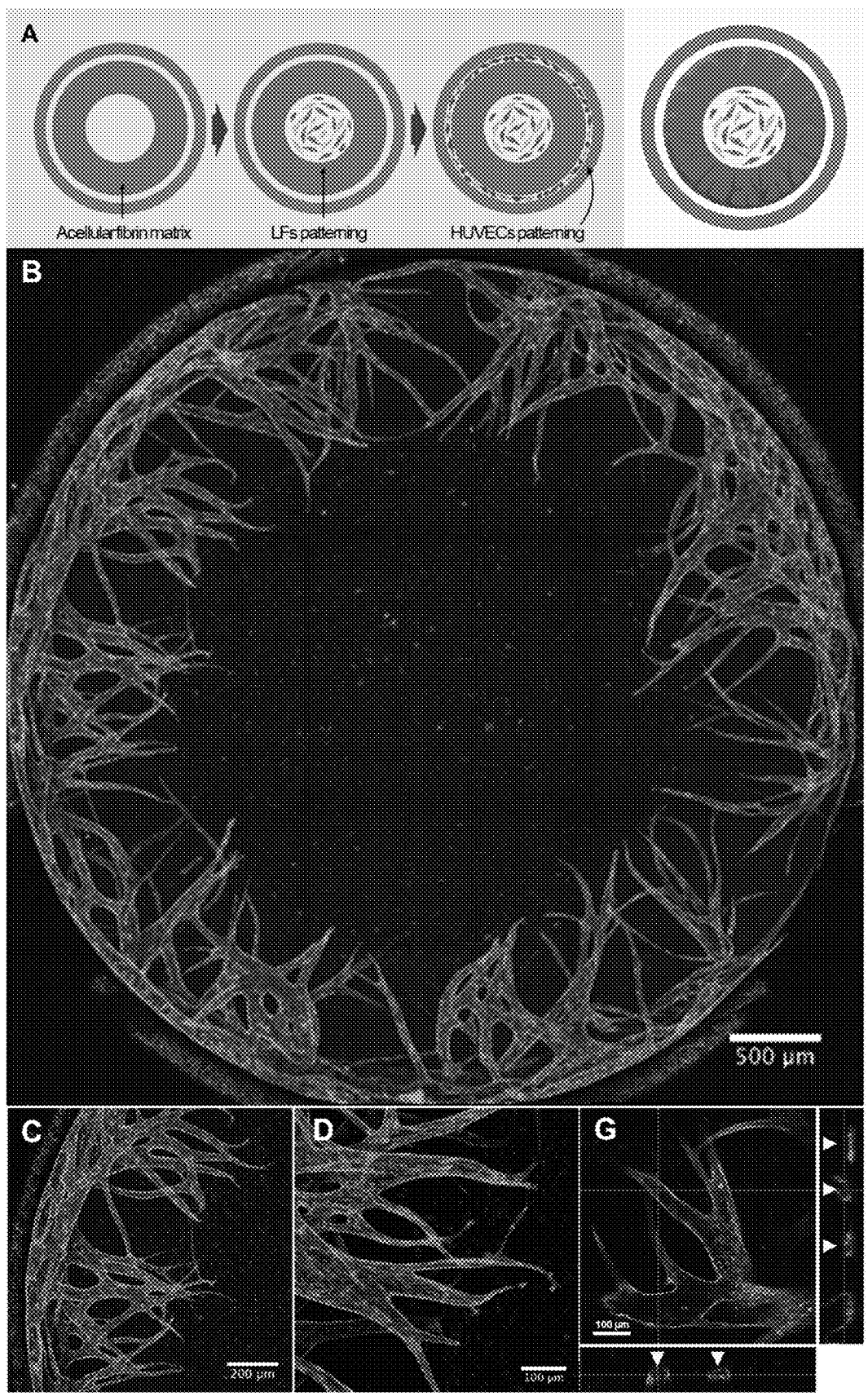
FIG. 16 shows example angiogenesis images obtained using a device described herein.

FIG. 16 shows example angiogenesis images obtained using a device described herein (e.g., the microfluidic device shown in FIG. 15). FIG. 16 shows that the device can serve as a microfluidic platform for angiogenesis studies.

FIG. 16(A) shows that, after the acellular fibrin gel is patterned under the guide structure, Normal Human Lung Fibroblasts (NHLFs) are loaded in the center, and the HUVECs are seeded on the outer edge. Since NHLFs, positioned at the center, secrete vascular endothelial growth factor radially, vascular sprouting also converges toward the center area. FIG. 16(B) is a confocal image of sprouting vessels. FIG. 16(C) is a fluorescence image of a part of the device. FIG. 16(D) a high-magnification image showing morphology of blood vessels. FIG. 16(G) is a confocal cross section image of the blood vessels, which confirms the formation of the lumen.

Figure 17:
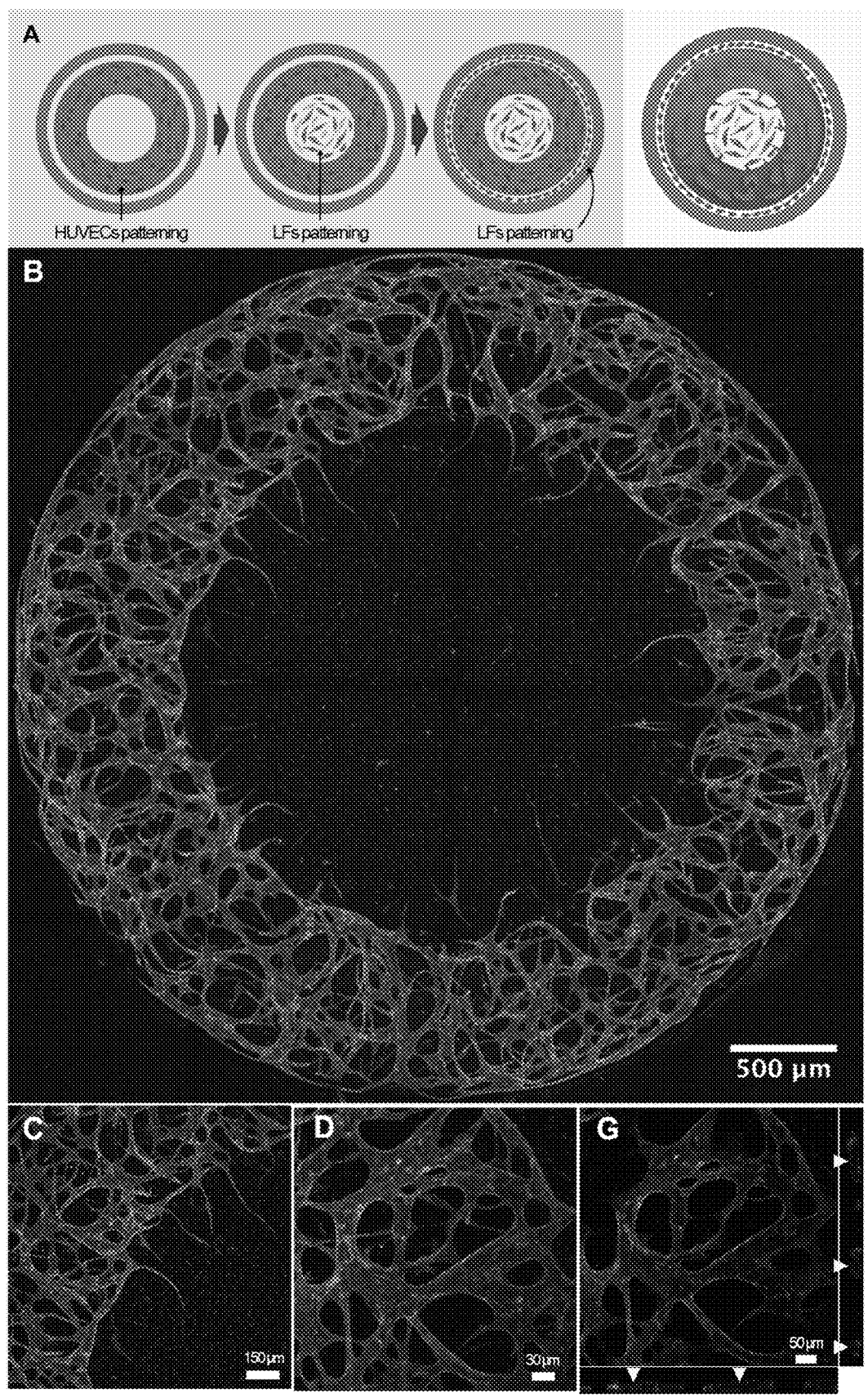
FIG. 17 shows example vasculogenesis images obtained using a device described herein.

FIG. 17 shows example vasculogenesis images obtained using a device described herein. FIG. 17 shows that the device can serve as a microfluidic platform for vasculogenesis studies.

FIG. 17(A) shows that the HUVECs and fibrin gel mixture is patterned under the guide structure and the NHLFs are loaded at the center. Additional NHLFs are seeded on the outer edge. Since the central NHLFs secretes vascular endothelial growth factor in a radial manner, the vascular network is formed uniformly in a circular pattern.

FIG. 17(B) is a confocal image of vascular network. FIG. 17(C) is a fluorescence image of a part of the device. FIG. 17(D) is a high-magnification image showing morphology of blood vessels. FIG. 17(G) is a confocal cross section image of the blood vessels confirms the formation of the lumen.

Figure 18:
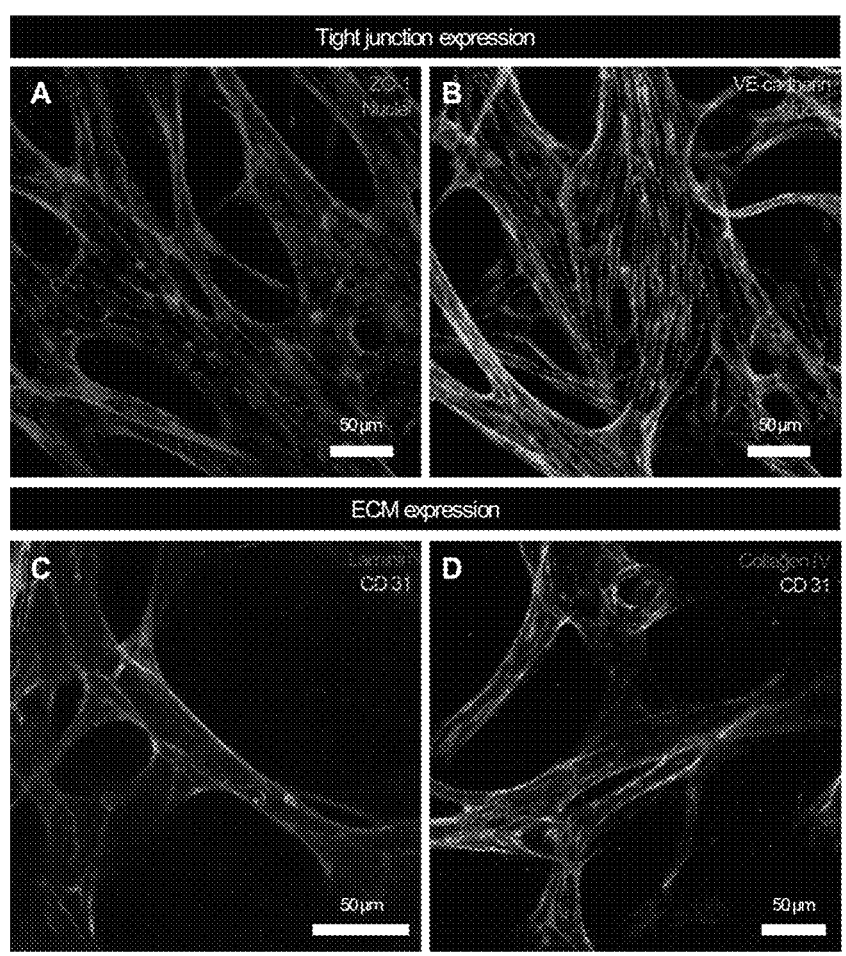
FIG. 18 shows images confirming formation of vascular system using a device described herein.

FIG. 18 shows images confirming formation of vascular system using a device described herein. Immunostaining for ZO-1 (A) and VE-Cadherin (B) tight junction protein expression by CD 31 positive endothelial cells confirms formation of the engineered vascular system. Confocal micrographs of the engineered vessels stained for the major components of substrate membrane, Laminin (C) and Collagen IV (D), also confirm formation of the engineered vascular system.

Figure 19:
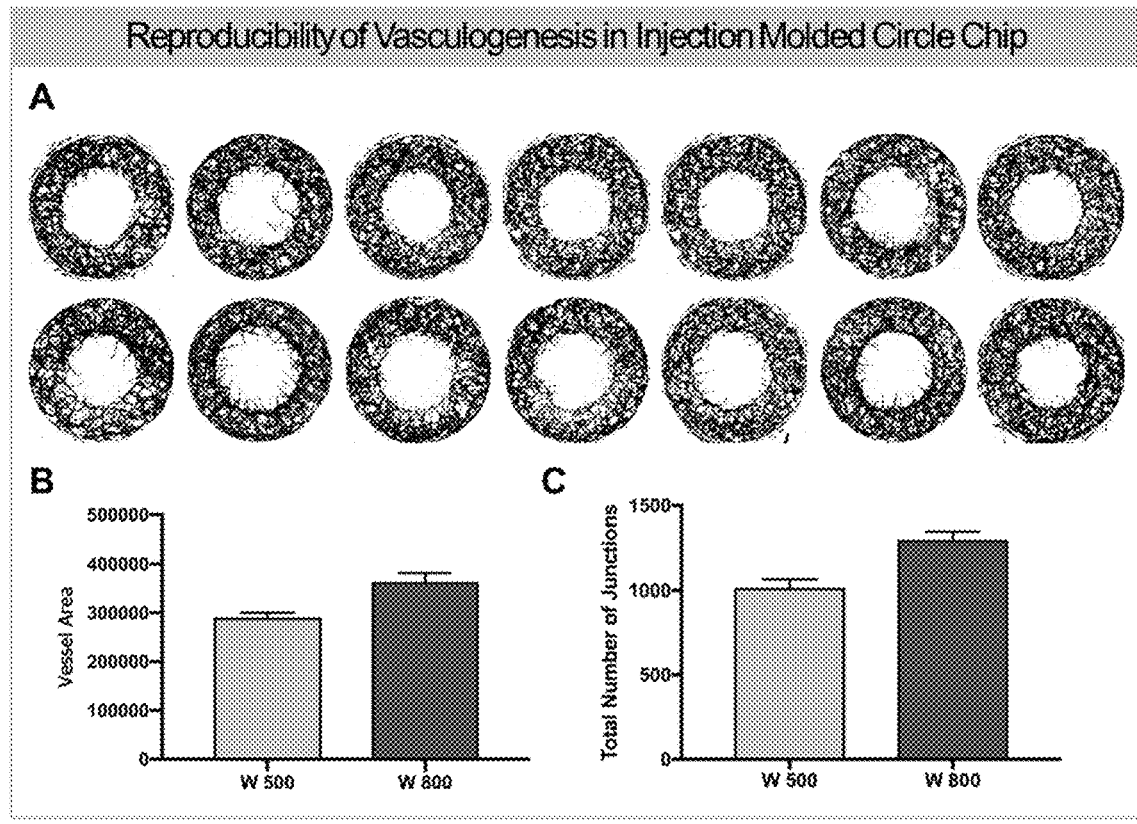
FIG. 19 shows reproducibility of vascular system formed using a device described herein.
Figure 19:
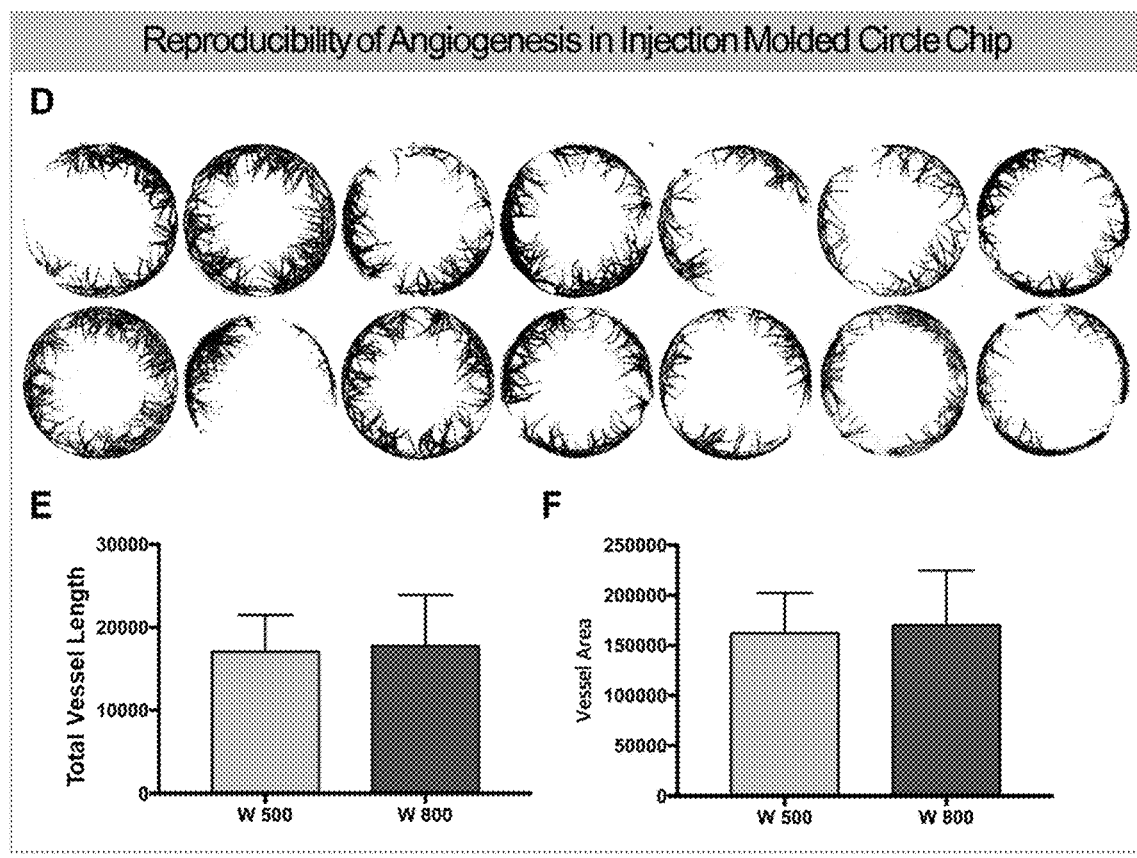

FIG. 19 reproducibility of vascular system formed using a device described herein (e.g., the device shown in FIG. 15). The reproducibility of the outcome obtained from each microchip is important for this platform which is mass-produced through injection molding. To demonstrate reproducibility, vasculogenesis and angiogenesis experiments were carried out under the same conditions. Experimental results were collected and quantified based on vessel characteristics. In the case of vasculugenesis, the representative model was compared and analyzed for vessel area and total number of junctions. In terms of angiogenesis, the total vessel length and vessel area were analyzed. These results show that the vascular system formed using the device is highly reproducible.

Figure 20:
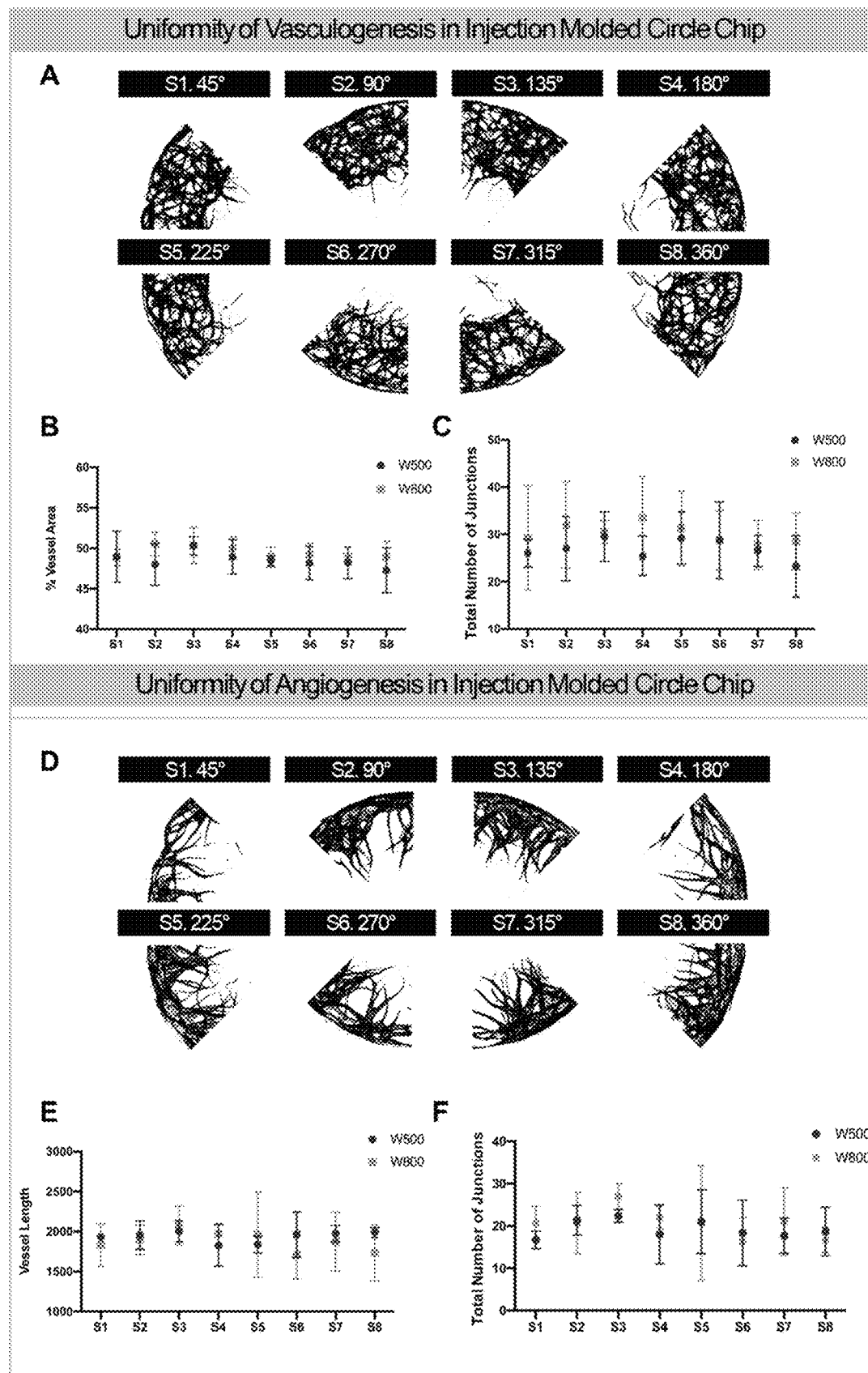
FIG. 20 shows uniformity of vascular system formed using a device described herein.

FIG. 20 shows uniformity of vascular system formed using a device described herein (e.g., the device shown in FIG. 15). The device shown in FIG. 15 is characterized by a circle shape, which has the advantage of being capable of factor supply from the center radially. Eight pieces of each sample were divided identically, and the quantification was performed on each section based on the characteristics of the blood vessels. In the case of vasculogenesis, blood vessel density and total number of junctions were analyzed. And, angiogenesis samples were analyzed by vessel length and total number of junctions. The results show that the vascular system formed using the device has a high uniformity among the sections.

Figure 21:
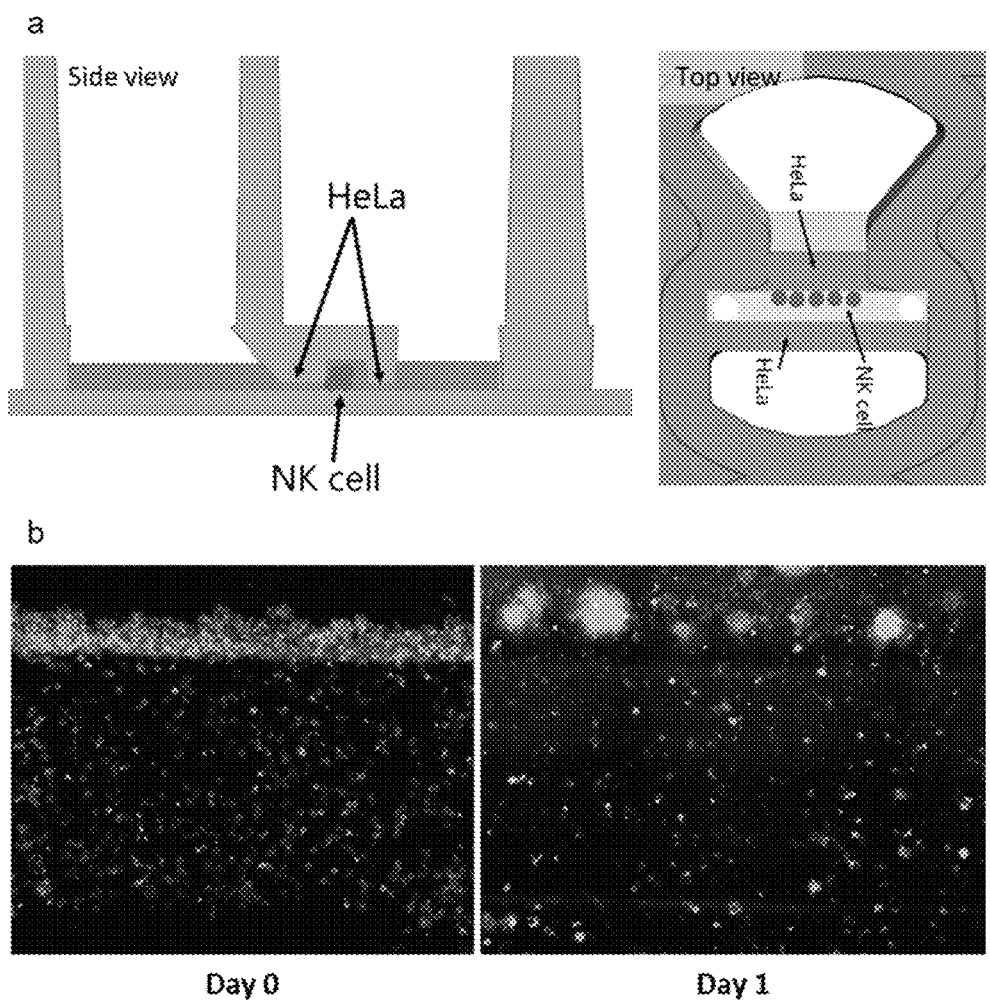
FIG. 21 shows images showing cell assays using a device described herein.

FIG. 21 shows images showing cell assays using a device described herein (e.g., the device shown in FIG. 1). FIG. 21($a$) shows the configuration of patterned cells. HeLa cells encapsulated in collagen were patterned between the lower rails and bottom surface and NK cell suspension was loaded in the channel formed by the patterned collagens. FIG. 21($b$) shows NK-92 cells migrated into the gel by killing HeLa cells in the path of migration. Other cells left in the medium aggregated into spheroids.

Figure 22:
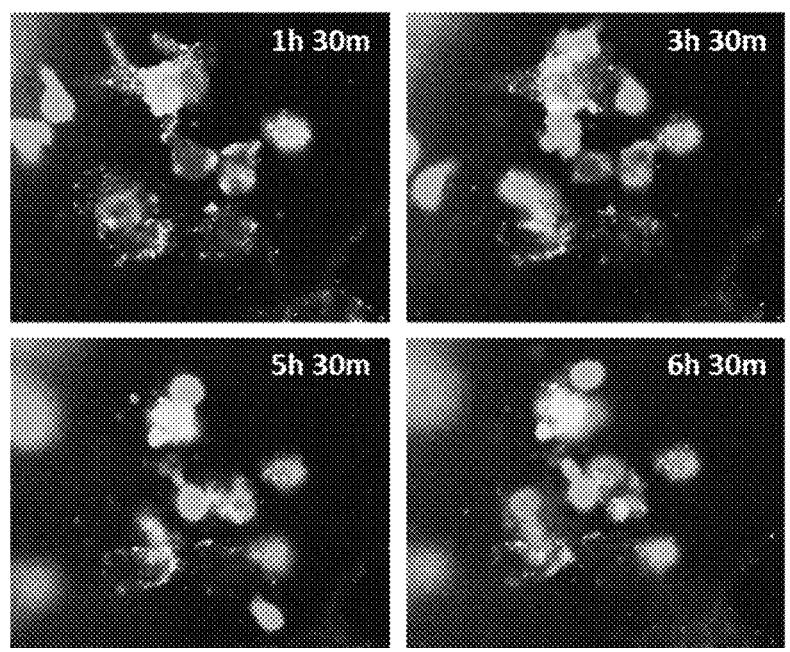
FIG. 22 shows images obtained by real-time monitoring of cytotoxic activity of NK-92 cells using a device described herein.

FIG. 22 shows images obtained by real-time monitoring of cytotoxic activity of NK-92 cells using a device described herein. NK-92 cells move around the HeLa cells by making the edges of HeLa cells lose the connection with collagen to have a sphere shape for longer than one hour and dead signals appeared about two hours later of shrinkage.

Figure 23:
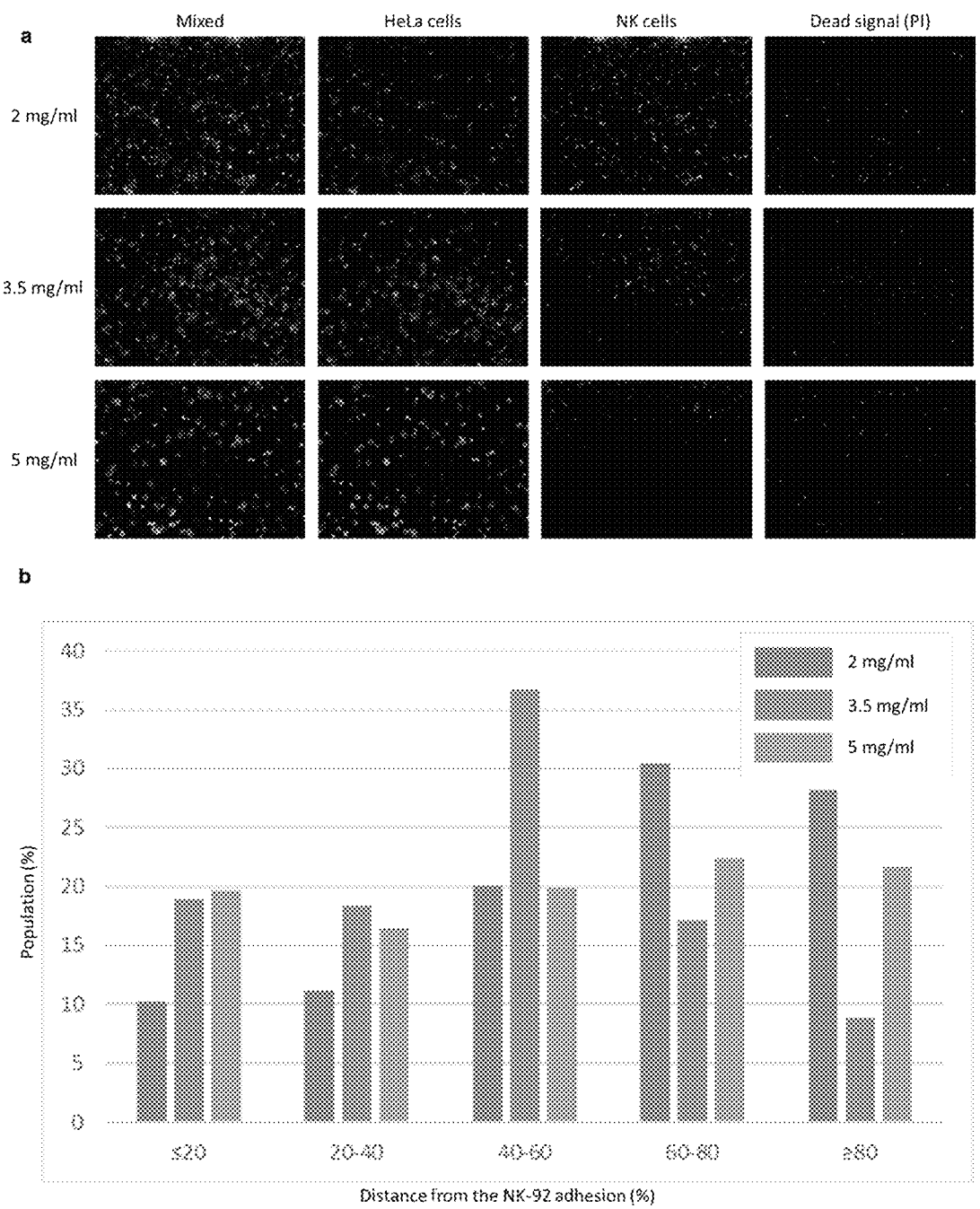
FIG. 23 shows migration and cytotoxic activity of NK-92 cells, as monitored using a device described herein.

FIG. 23 shows migration and cytotoxic activity of NK-92 cells in various collagen concentrations to reconstitute tumor-associated fibrosis, as monitored using a device described herein. FIG. 23($a$) shows that NK-92 cells migrated inactively in the denser collagens and dead signals were frequently observed at the front of migration of NK-92 cells. FIG. 23($b$) shows the populations of dead signals according to the distance from the side where NK-92 cells were adhered. The collagen block with width of 800 μm, patterned between a rail and the bottom surface, is divided into five regions according to the distance and the populations of dead signals were plotted. In 2 and 3.5 mg/ml of collagens, dead signals were mostly observed at the front of NK-92 cells migration. In 5 mg/ml of collagen, however, the environment was so stiff that HeLa cells had lower viability than other concentrations across all regions.

Figure 24:
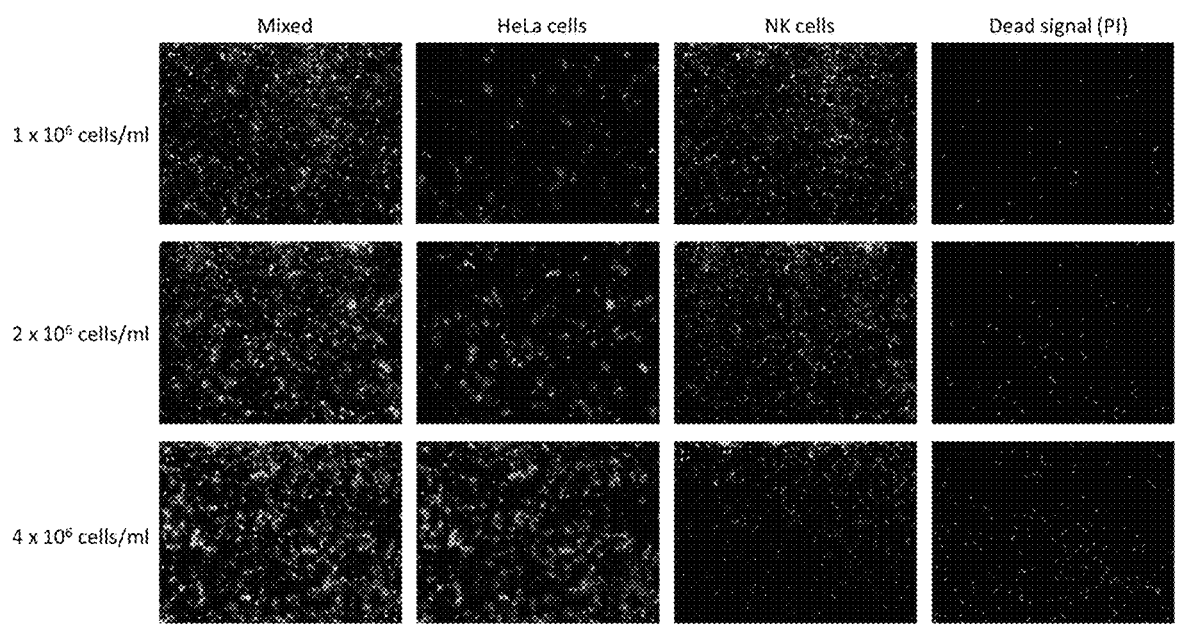
FIG. 24 shows migration and cytotoxic activity of NK-92 cells against various concentrations of HeLa cells, as monitored using a device described herein.

FIG. 24 shows migration and cytotoxic activity of NK-92 cells against various concentrations of HeLa cells, as monitored using a device described herein. After 18 hours of co-culture, NK-92 cells killed almost all of the HeLa cells patterned with $1\times10^6$ cells/ml. In case of the largest number of HeLa cells, migration of NK-92 cells seems to be limited due to the cytotoxic activity of NK-92 cells instead of migrating into the gel.

Figure 25:
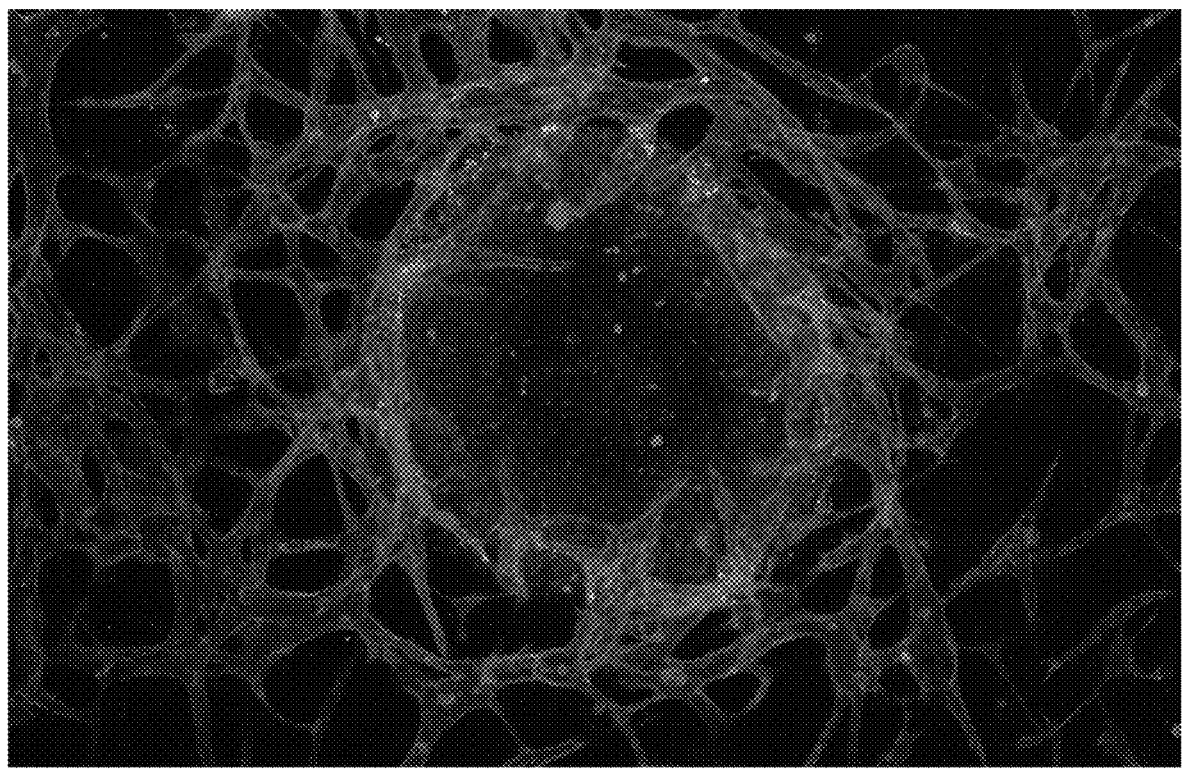
FIG. 25 shows a vascularized tumor spheroid formed by using a device described herein.

FIG. 25 shows a vascularized tumor spheroid formed by using a device described herein (e.g., the device shown in FIG. 15).

Figure 26:
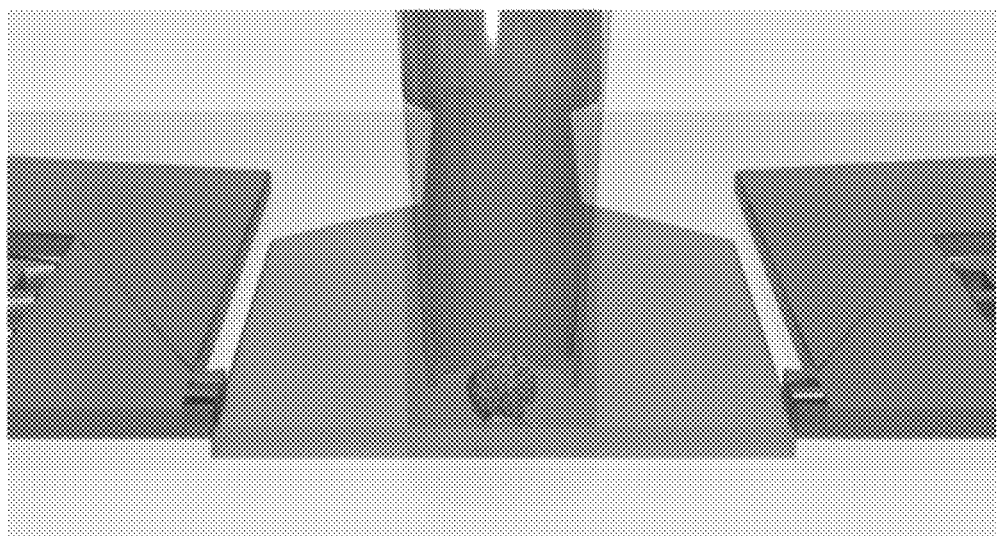
FIG. 26 illustrates a method of forming a vascularized tumor spheroid using a described herein in accordance with some embodiments.
Figure 26:
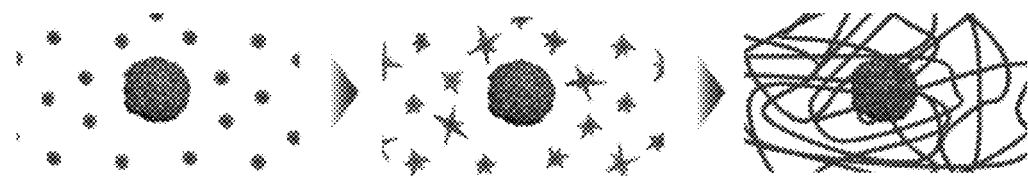

FIG. 26 illustrates a method of forming a vascularized tumor spheroid using a described herein (e.g., the device shown in FIG. 15) in accordance with some embodiments. A tumor spheroid was cultured in a u-shaped culture plate, and was subsequently co-cultured in the microfluidic device with fibroblasts to obtain a vascularized tumor spheroid.

Figure 27:
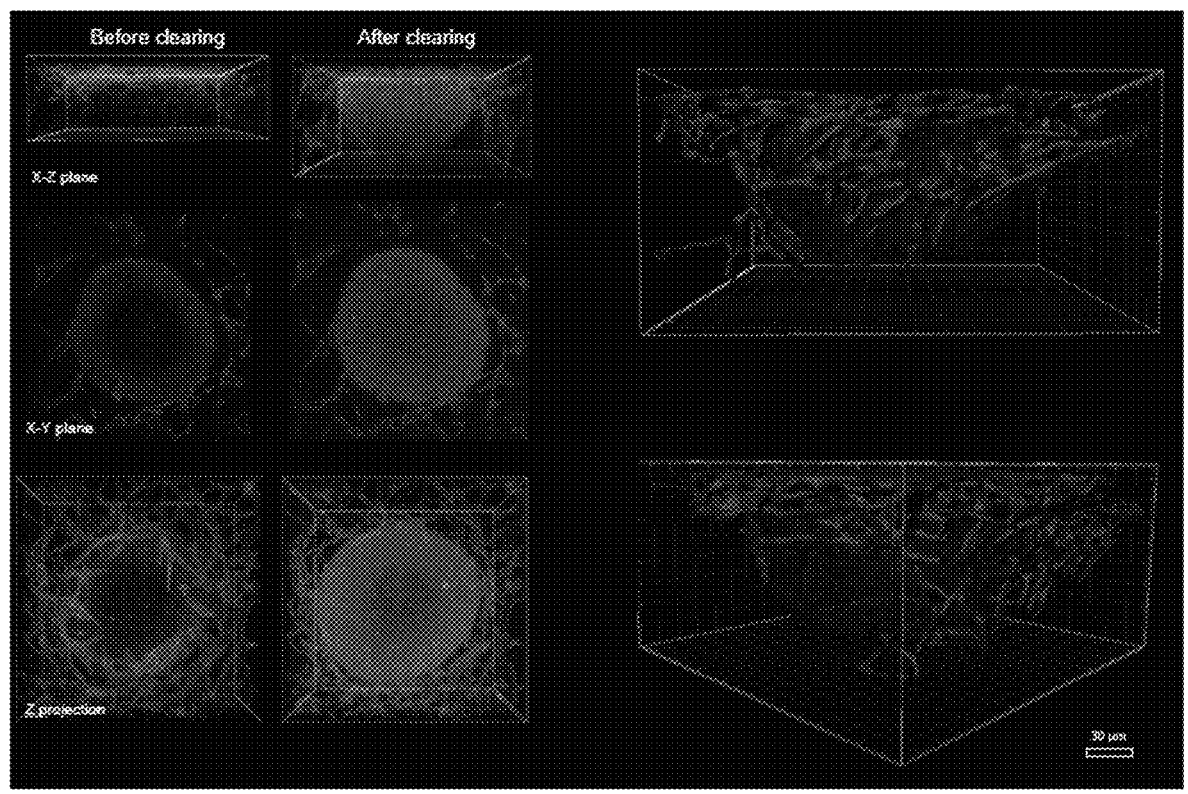
FIG. 27 shows an image of a tumor spheroid formed by using a device described herein.

FIG. 27 shows an image of a tumor spheroid formed by using a device described herein (e.g., the device shown in FIG. 15). Using a tissue clearing method, the tumor spheroid having approximate diameter of 1 mm was imaged.

Figure 28:
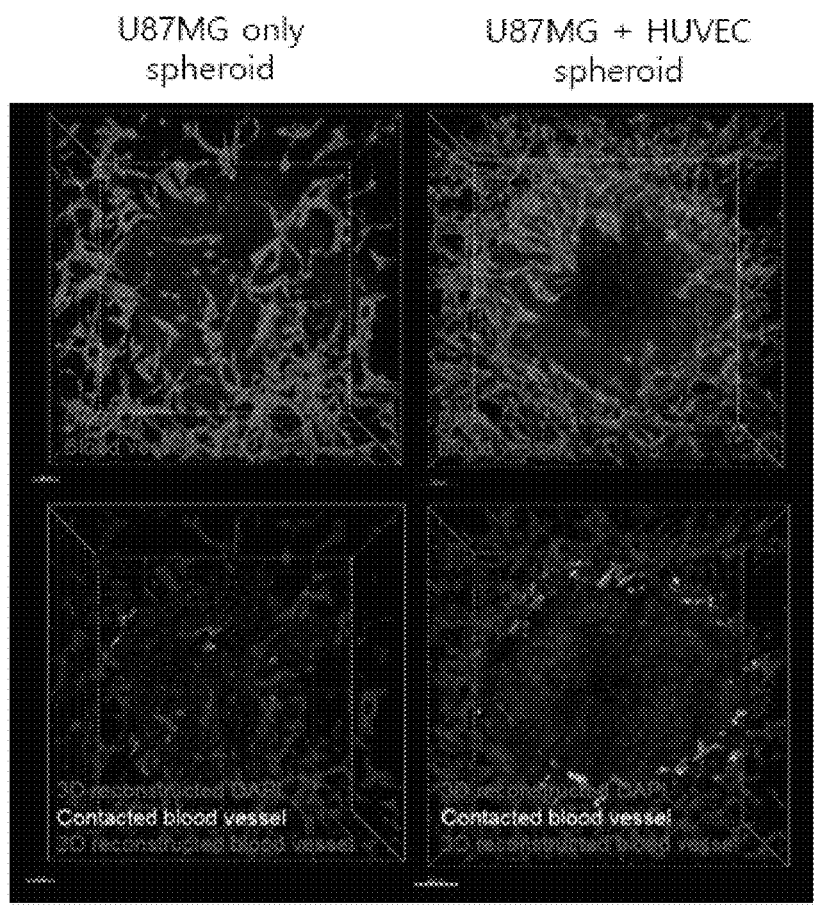
FIG. 28 shows tumor spheroids that have been formed by using a device described herein.

FIG. 28 shows tumor spheroids that have been formed by using a device described herein. FIG. 28 shows that a tumor spheroid co-cultured with vascular endothelial cells is more effective in vasculogenesis than a tumor spheroid that has not been co-cultured with vascular endothelial cells.

Figure 29:
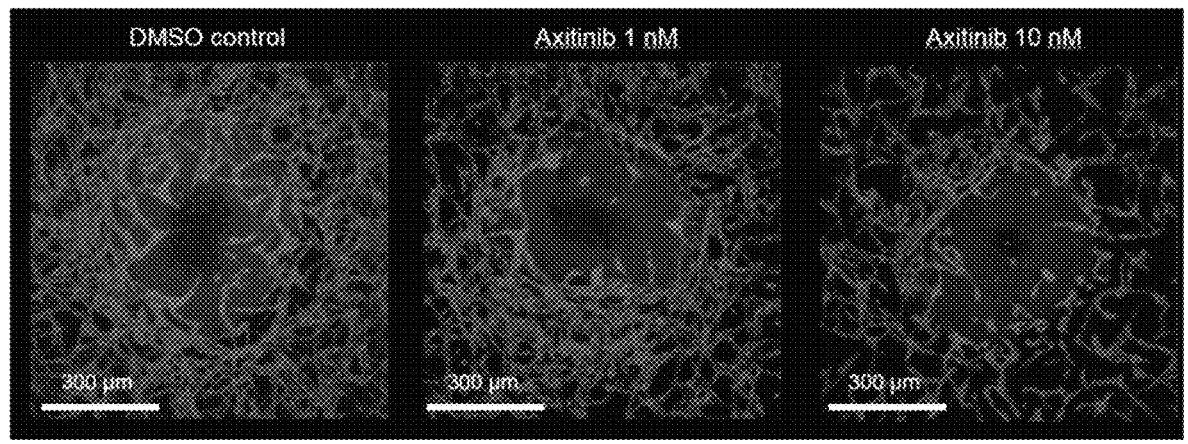
FIG. 29 shows an effect of a tyrosine kinase inhibitor on a tumor spheroid, as monitored using a device described herein.

FIG. 29 shows an effect of a tyrosine kinase inhibitor (e.g., axitinib) on a tumor spheroid, as monitored using a device described herein. Axitinib is a tyrosine kinase inhibitor that selectively inhibits vascular endothelial growth factor VEGFR-1, VEGFR-2, and VEGFR-3. Axitinib also inhibits platelet-derived growth factor (PDGF). FIG. 29 shows that axitinib has reduced the vessel area, the diameter of vessels, and the number of vessels interacting with the tumor spheroid.

Figure 30:
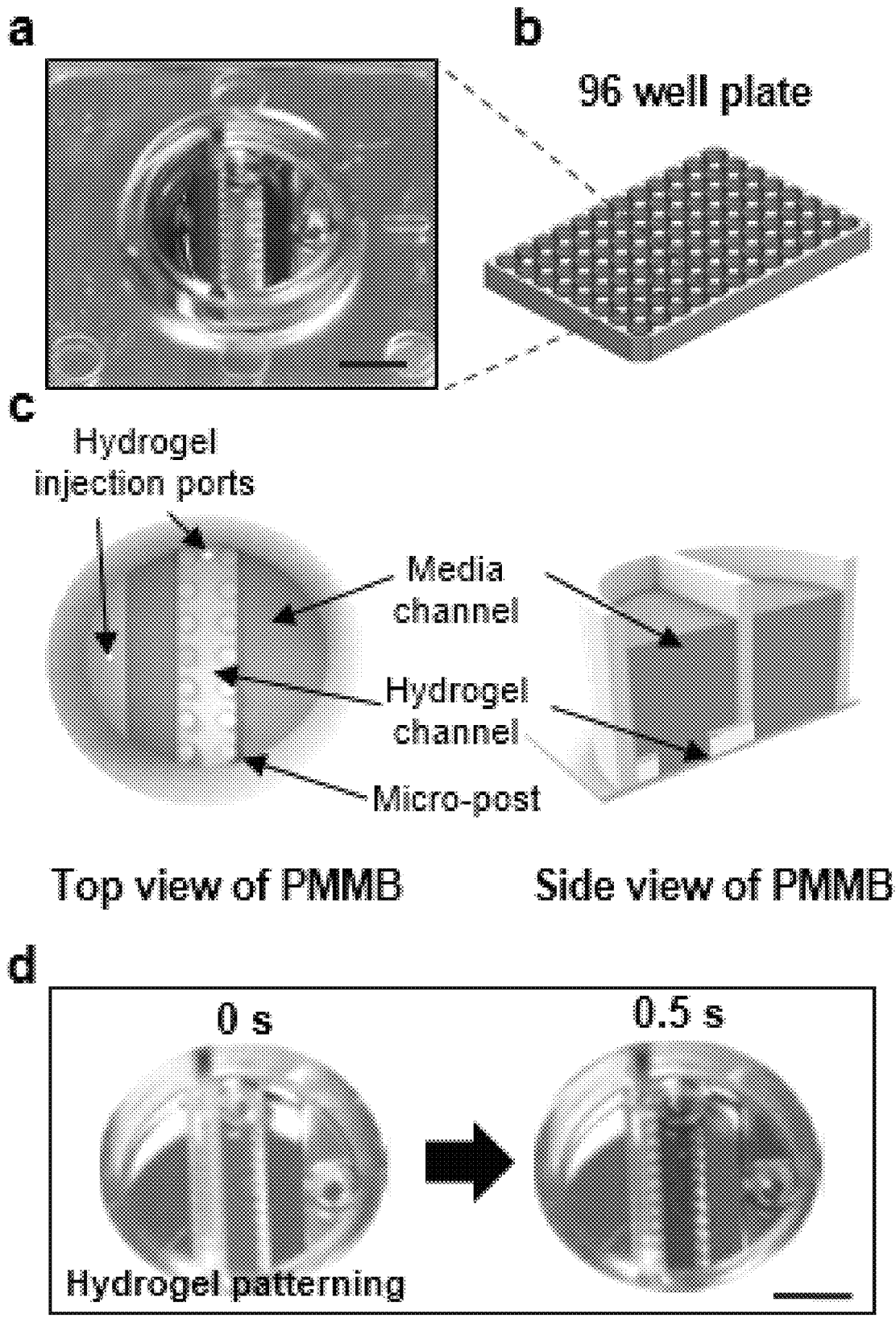
FIG. 30 shows a structure of a device for high-throughput experiment.

FIG. 30 illustrates a structure of a device (called herein PMMB) for high-throughput experiment.

FIG. 30(a) is an example photograph of a PMMB device. FIG. 30(b) is a schematic diagram of a 96 well microplate with 96 independent PMMB devices for high-throughput experiment and drug screening. FIG. 30(c) is a schematic diagram illustrating a PMMB device including two hydrogel injection ports, two media channels, a hydrogel channel, and micro-posts in the top view (left) and side view (right). FIG. 30(d) shows the speed of hydrogel patterning on hydrophilic state on a PMMB device. The scale bar represents 2 mm.

Figure 31:
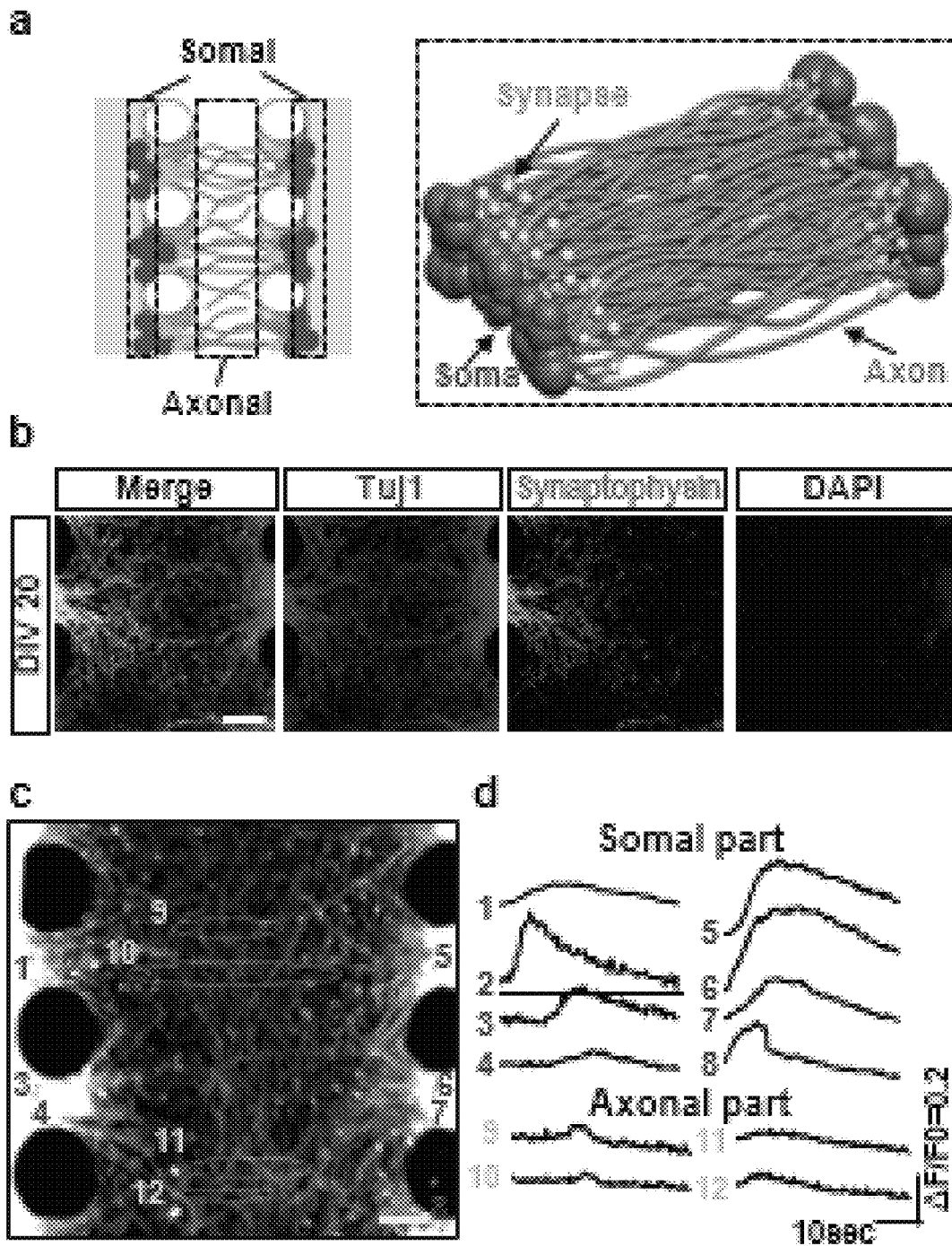
FIG. 31 shows reconstruction of a three-dimensional neural network in the PMMB.

FIG. 31 shows reconstruction of a three-dimensional neural network in the PMMB device. FIG. 31(a) is a schematic diagram illustrating a three-dimensional neural network. CNS neurons were seeded on both side of media channel. Axons of CNS neurons extended into gel channel, forming synapse. FIG. 31(b) Representative fluorescence confocal images of CNS neuron at DIV20 immunostained for Tuj1, synaptophyisin, and DAPI. Scale bar, 100 μm. Functional calcium activity of the three-dimensional neural network was analyzed by using the Oregon Green 488-BAPTA-1 AM at DIV 20. Randomly selected eight soma regions and four axon regions are measured. Representative image of neural network stained with BAPTA-1 AM (FIG. 31(c)). Changes of the fluorescence intensity at twelve selected regions (FIG. 31(d), indicated by numbers shown in FIG. 31(c)) are shown. Scale bar, 100 μm.

Figure 32:
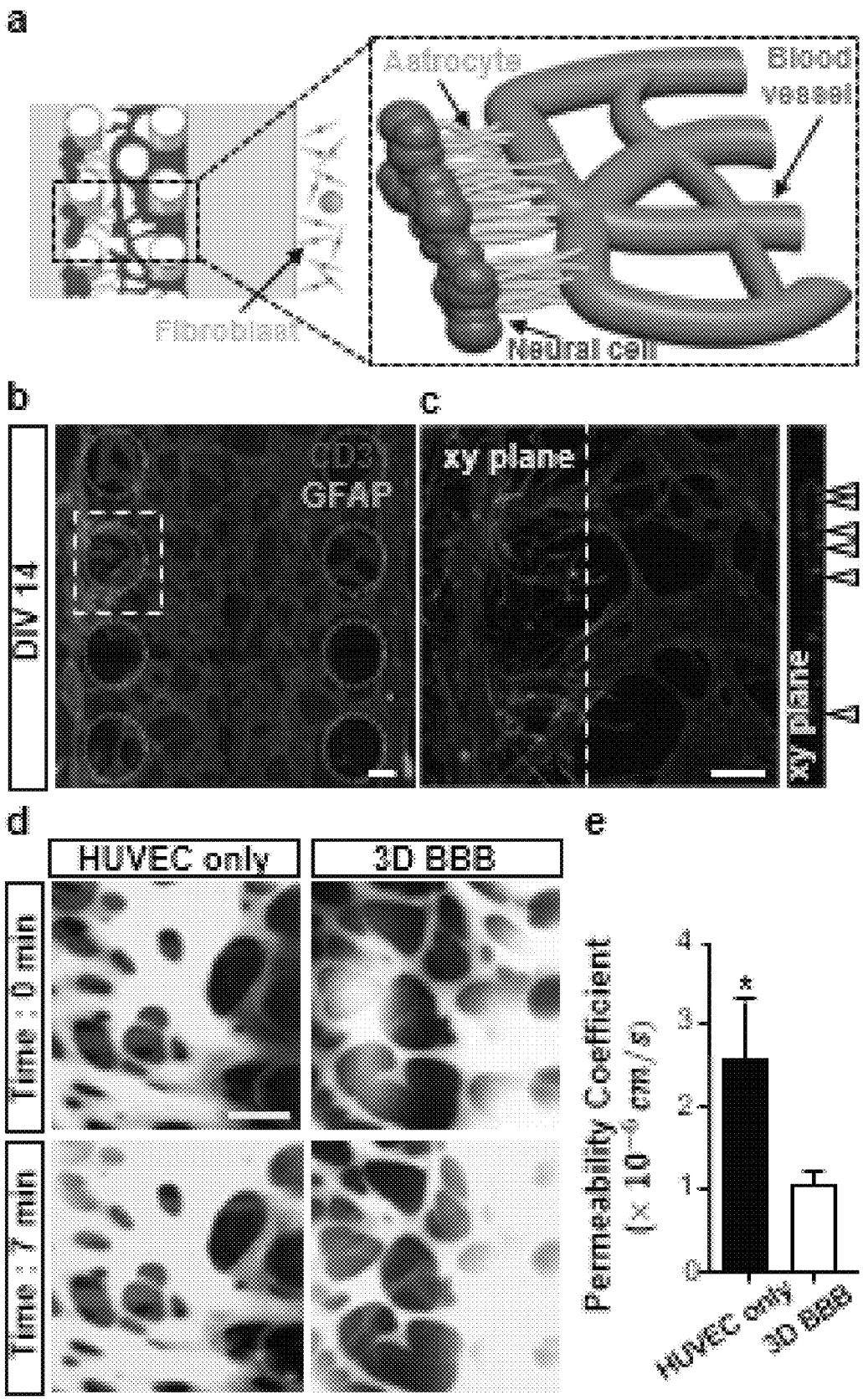
FIG. 32 shows reconstruction of a three-dimensional BBB with coculture of CNS neuron-astrocyte-HUVEC in the PMMB.

FIG. 32 shows reconstruction of a three-dimensional blood brain barrier (BBB) with coculture of CNS neuron-astrocyte-HUVEC in the PMMB device. FIG. 32(a) is a schematic diagram illustrating three-dimensional reconstructed BBB model. HUVECs and LFs were firstly injected with the mixture of hydrogel into the gel channel. After 4 days, CNS cells including neurons and astrocytes were seeded into the media channel opposite to LFs. Astrocytic endfeet were anchored on vascular network. Representative fluorescence confocal images of CNS neuron-astrocyte-HUVEC coculture immunostained with platelet-endothelia cell adhesion molecule-1[PECAM-1] (CD31) and glia fibrillary acidic protein (GFAP) at DIV 14 (of neuron). The confocal image in FIG. 32(c) showed enlarged boxed area of FIG. 32(b) and arrow heads (right) confirmed direct contact between astrocyte and vascular network. Scale bar, 100 μm. FIG. 32(d) shows example time-lapse microscopic photographs of HUVEC with or without astrocyte with 70 kDa FITC-dextran at time 0 and 7 min, respectively. FIG. 32(e) shows quantification results of BBB permeability. The permeability of only HUVECs is 2.6±0.7, while coculture with astrocyte is 1.0±0.2. Graph shows mean±SEM values from ten independent experiments. Scale bar, 200 μm (unpaired, two-tailed-t test with Welch's correction).

Figure 33:
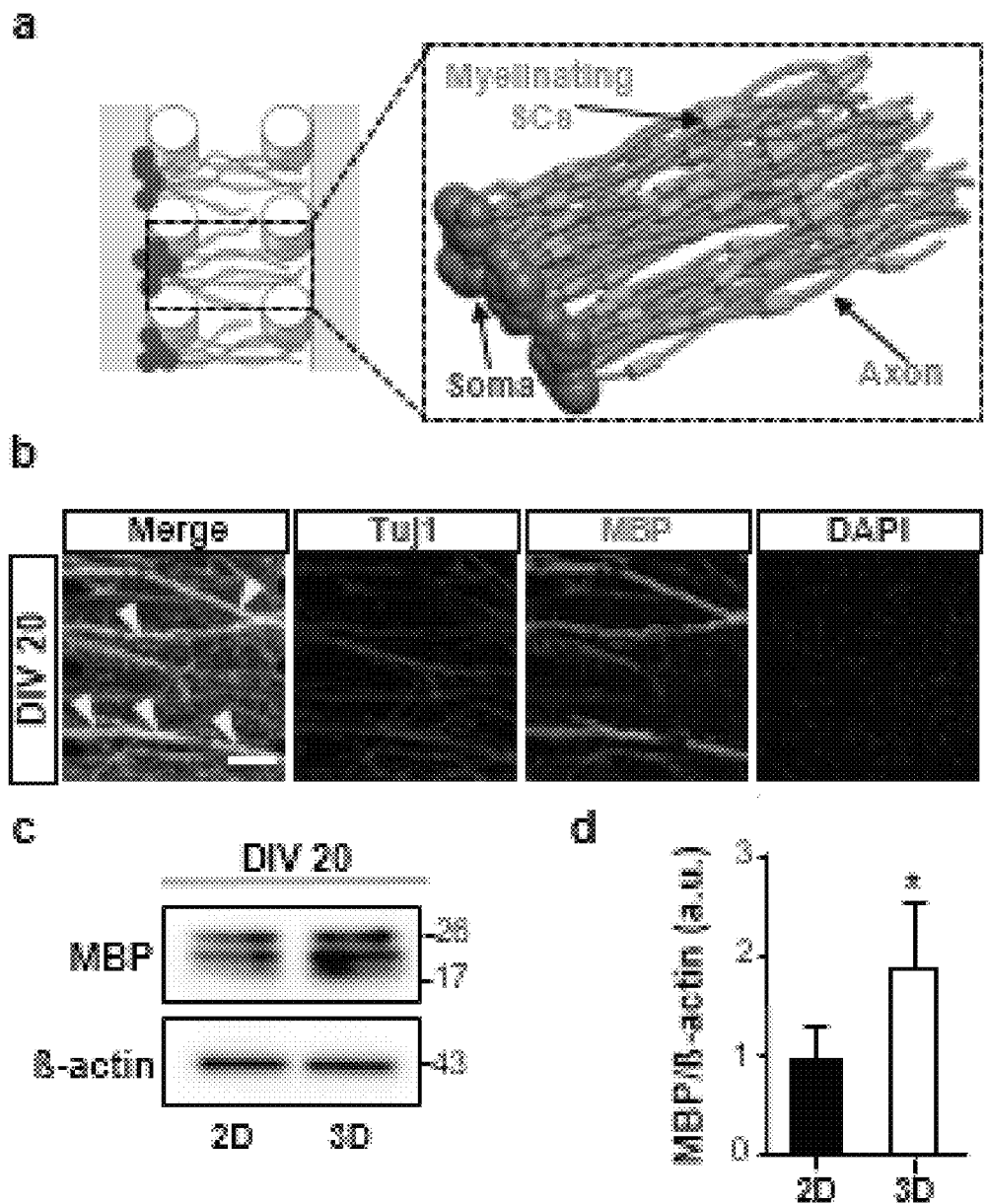
FIG. 33 shows reconstruction of a three-dimensional formation of myelin sheaths in the PMMB.

FIG. 33 shows reconstruction of three-dimensional formation of myelin sheaths in the PMMB device. FIG. 33(a) is a schematic diagram illustrating three-dimensional coculture of PNS neruons-Schwann cells (SCs). SCs were firstly seeded into one hydrogel channel and after 3 hours, PNS neurons were then seeded into other side of media channel. SCs migrated and proliferated, while PNS neurons extend axons into gel channel. Over time, SCs contacted and wrapped around the axons of neurons, forming myelin sheath. FIG. 33(b) shows example fluorescence confocal images of PNS neuron-SC coculture immunostained with tubulin beta III (Tuj1), myelin basic protein (MBP), and DAPI at DIV 20. The expression of MBP became highly localized along the axons of PNS neurons (arrow heads). Scale bar, 200 μm. The level of MBP was determined by western blot analysis at DIV 20. The level of MBP expression on three-dimensional coculture of the PMMB was compared to three-dimensional coculture on a coverslip coated with Matrigel (2D). Representative immunoblots (FIG. 33(c)) and quantification (FIG. 33(d)) of MBP levels are shown. Protein levels were normalized against the level of β-actin which was used as a loading control. Graph shows mean±SEM values from three independent experiments. (unpaired, two-tailed-t test with Welch's correction).

Figure 34:
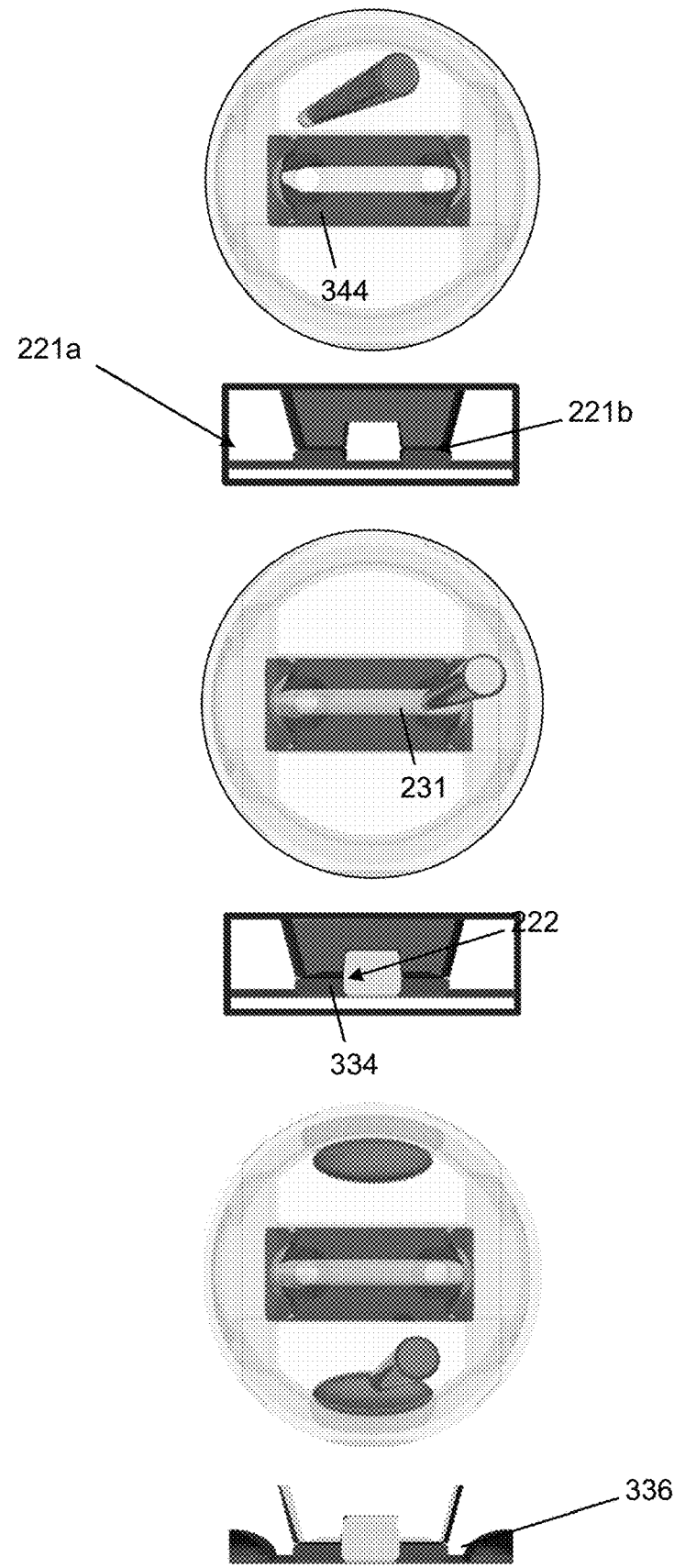
FIG. 34 illustrates a fluid patterning process using a microfluidic device in accordance with some embodiments.

FIG. 34 illustrates a fluid patterning process using a microfluidic device in accordance with some embodiments. The fluid patterning process shown in FIG. 34 is similar to the fluid patterning process shown in FIG. 3 except that the first fluid 344 need not be provided to a location away from microfluidic channels 221a and 221b. Instead, the first fluid 344 may be provided to a location adjacent to microfluidic channel 221a or microfluidic channel 221b. This eliminates the need for the first fluid 344 to flow through the inner corner of the side wall. However, the first fluid 344 may be provided away from microfluidic channels 221a and 221b as shown in FIG. 3. Similarly, in FIG. 3, the first fluid 344 need not be provided to a location away from microfluidic channels and may be provided to a location adjacent to the microfluidic channels, in a manner analogous to that shown in FIG. 34. Returning to FIG. 34, after the first fluid 344 is provided to fill microfluidic channels 221a and 221b, the second fluid 334 is provided to the microfluidic channel 222 (e.g., through the opening 231). In some embodiments, additional fluid (e.g., a culture medium 336) is provided to one or more locations adjacent to the side wall.

Figure 35:
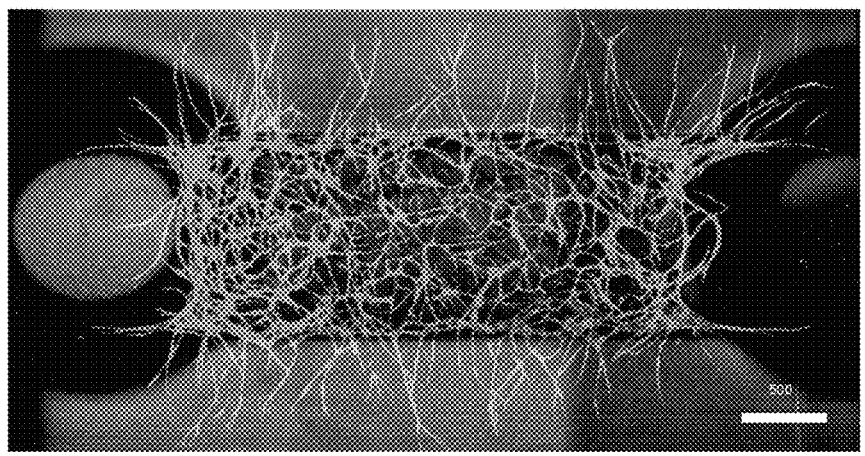
FIG. 35 illustrates angiogenesis on the microfluidic device shown in FIG. 34.
Figure 36:
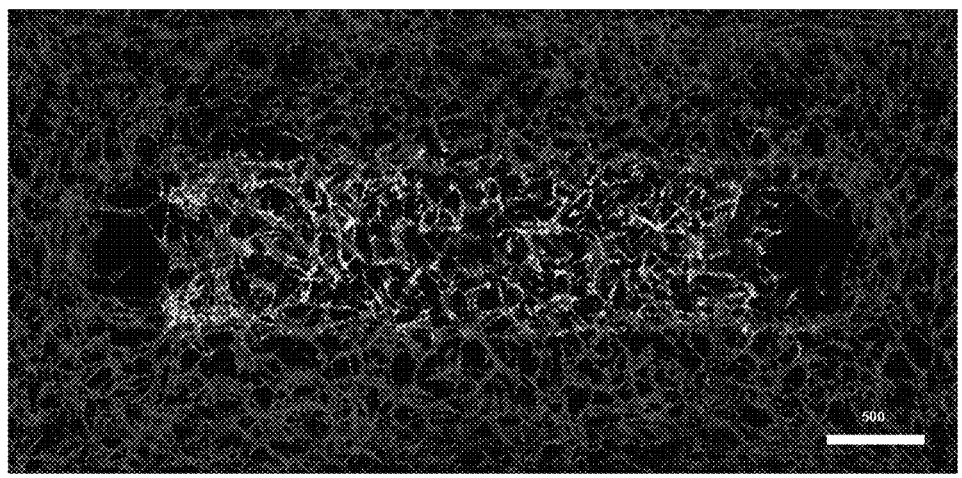
FIG. 36 illustrates vasculogenesis on the microfluidic device shown in FIG. 34.
Figure 37:
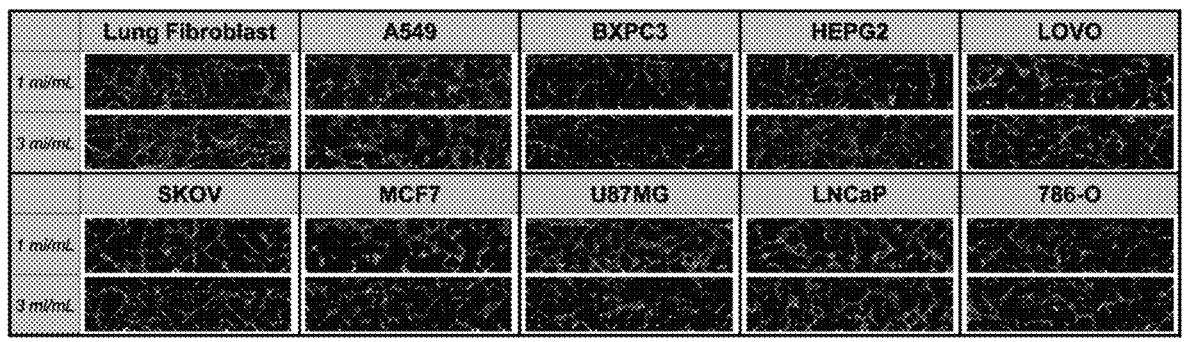
FIG. 37 illustrates angiogenesis on the microfluidic device shown in FIG. 34 using multiple types of cells.

FIG. 35 illustrates angiogenesis on the microfluidic device shown in FIG. 34. FIG. 36 illustrates vasculogenesis on the microfluidic device shown in FIG. 34. FIG. 37 illustrates angiogenesis on the microfluidic device shown in FIG. 34 using multiple types of cells. As shown in FIGS. 35-37, when cells (e.g., cancer cells) were provided in the second fluid 334, the cells formed vasculature in the first fluid 344.

Figure 38A:
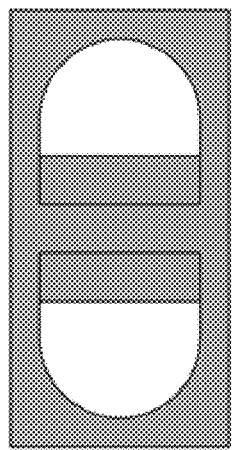
FIGS. 38A-38D illustrate a microfluidic device in accordance with some embodiments.
Figure 38B:
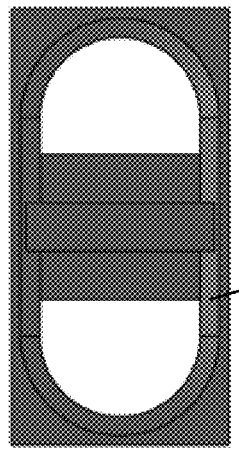
Figure 38C:
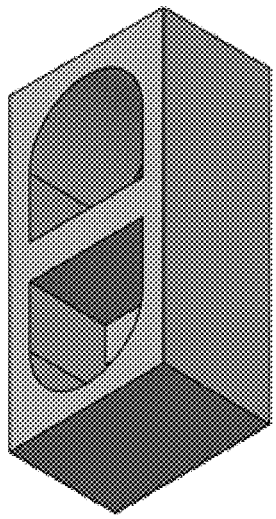
Figure 38D:
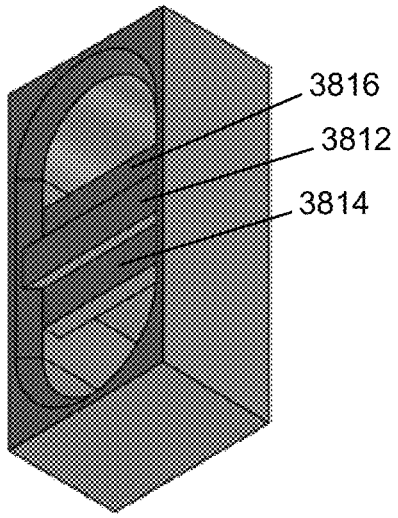

FIGS. 38A-38D illustrate a microfluidic device in accordance with some embodiments. FIG. 38A illustrates a top view of the microfluidic device, and FIG. 38B illustrates a bottom view of the microfluidic device. FIG. 38C illustrates a top isometric view of the microfluidic device and FIG. 38D illustrates a bottom isometric view of the microfluidic device. Typically, the microfluidic device shown in FIGS. 38A-38D is mounted on (e.g., sealingly attached to) a substrate with the bottom surface of the microfluidic device facing toward the substrate. As shown in FIG. 38B (and FIG. 38D), one or more portions (e.g., along the periphery of the well) of the bottom surface of the microfluidic device are chamfered. In addition, the bottom surface of the microfluidic device is shaped so that respective portions 3812, 3814, and 3816 of the bottom surface of the microfluidic device define respective microfluidic channels when the microfluidic device is mounted on a substrate. In some embodiments, when the microfluidic device is mounted on a substrate, the portion 3812 has a first distance, the portion 3814 has a second distance greater than the first distance, and the portion 3816 has a third distance greater than the first distance, as shown in FIG. 38D. In some embodiments, the second distance and the third distance are identical. In some embodiments, the second distance is different from the third distance.

Figure 39A:
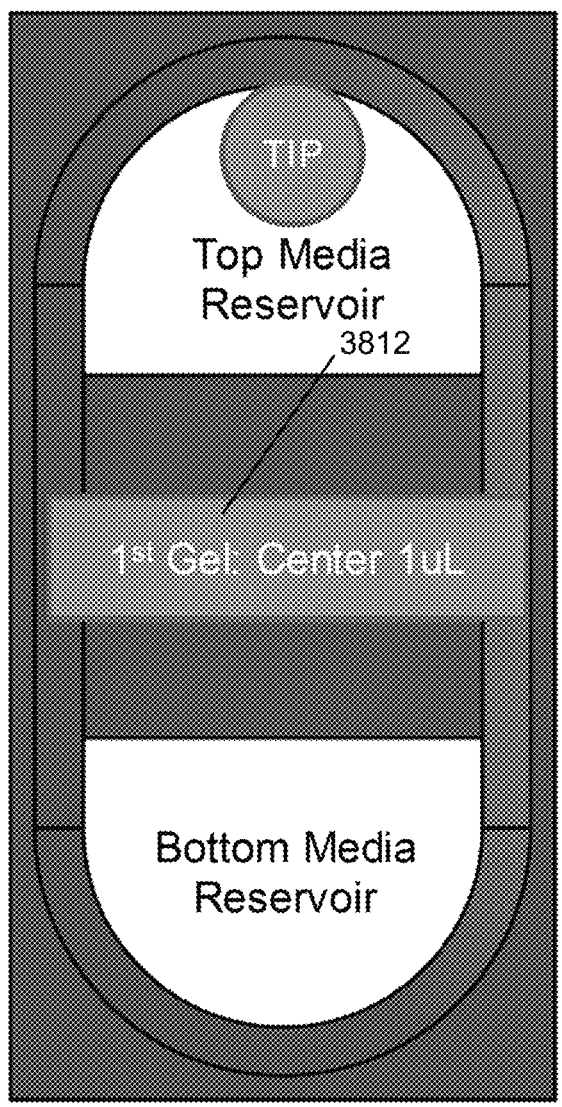
FIGS. 39A and 39B illustrate a fluid patterning on the microfluidic device shown in FIGS. 38A-38D in accordance with some embodiments.
Figure 39B:
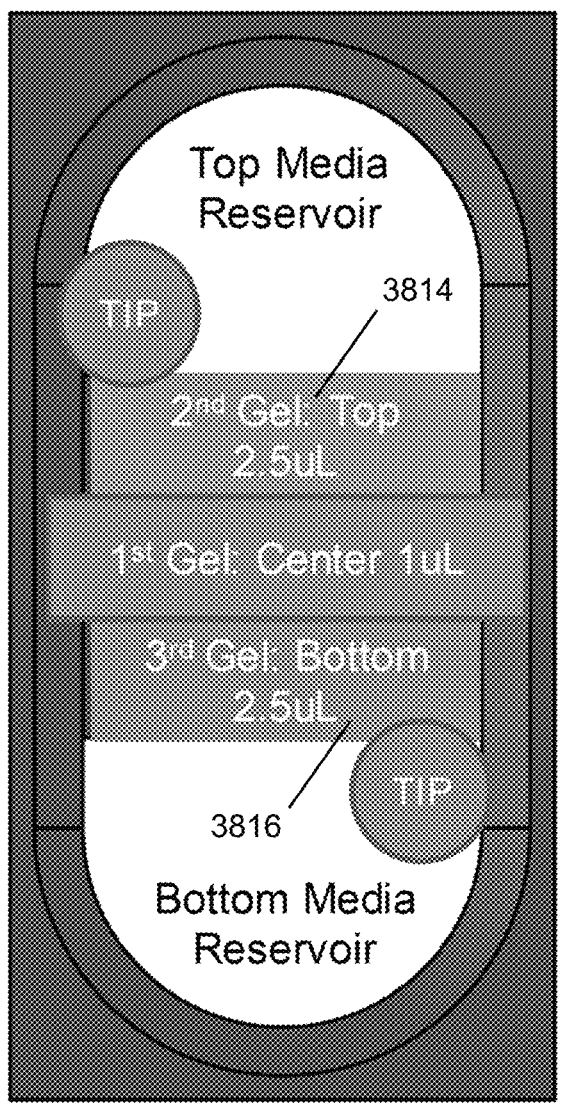

FIGS. 39A and 39B illustrate a fluid patterning on the microfluidic device shown in FIGS. 38A-38D in accordance with some embodiments. FIG. 39A shows that a first fluid (or a first gel) is provided adjacent to an edge of the side wall (e.g., by placing a pipette tip adjacent to the edge of the side wall). The first fluid follows the inner corner paths to fill the microfluidic channel under the portion 3812 of the bottom surface of the microfluidic device. Depending on the size of the microfluidic device, the first fluid may have a volume of 0.9-1 µL. FIG. 39B shows that a second fluid is provided adjacent to the portion 3814 of the bottom surface of the microfluidic device, which fills the microfluidic channel under the portion 3814 of the bottom surface of the microfluidic device, and a third fluid is provided adjacent to the portion 3816 of the bottom surface of the microfluidic device, which fills the microfluidic channel under the portion 3816 of the bottom surface of the microfluidic device. Depending on the size of the microfluidic device, the second fluid and the third fluid may have a volume of 2-2.5 respectively. As a result, all three microfluidic channels may be filled with different fluids.

Figure 40A:
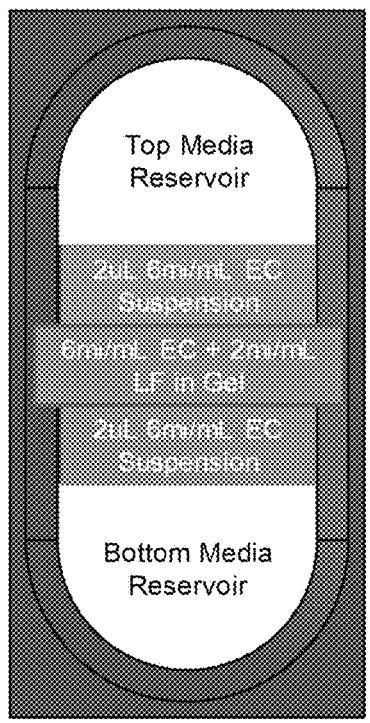
FIGS. 40A and 40B illustrate generation of perfusable center channel vasculature using the fluid-patterned microfluidic device shown in FIGS. 39A and 39B.
Figure 40A:
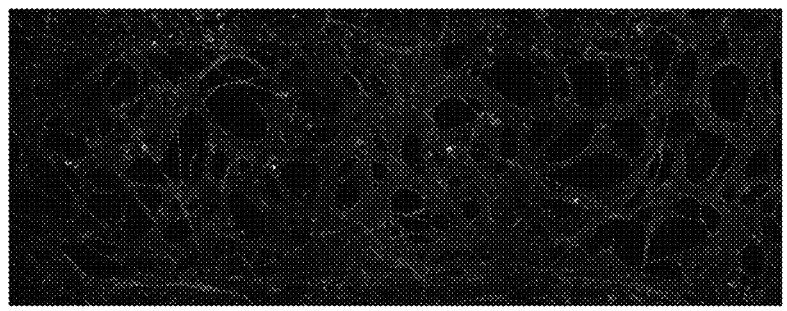
Figure 40B:
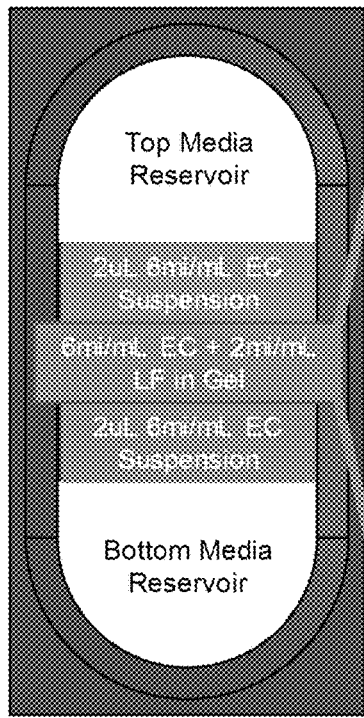
Figure 40B:
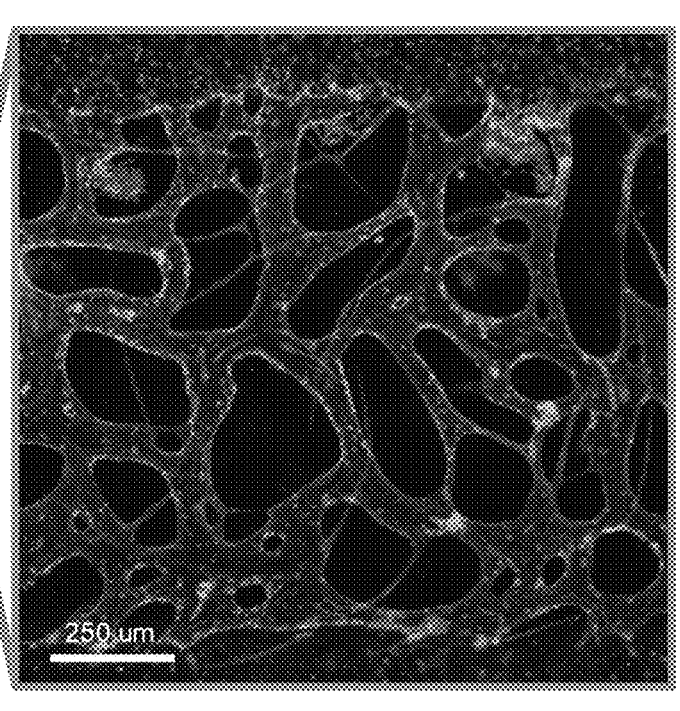

FIGS. 40A and 40B illustrate generation of perfusable center channel vasculature using the fluid-patterned microfluidic device shown in FIGS. 39A and 39B. FIG. 40A shows day 7 seeding of SW620-GFP single cell suspensions into mature perfusable vasculature. The red color represents Alexafluor 594 Lectin stained human umbilical vein endothelial cells (HUVECs). The green color represents SW620-GFP. FIG. 40B shows generation of perfusable center channel vasculature based on micro bead perfusion test.

Figure 40C:
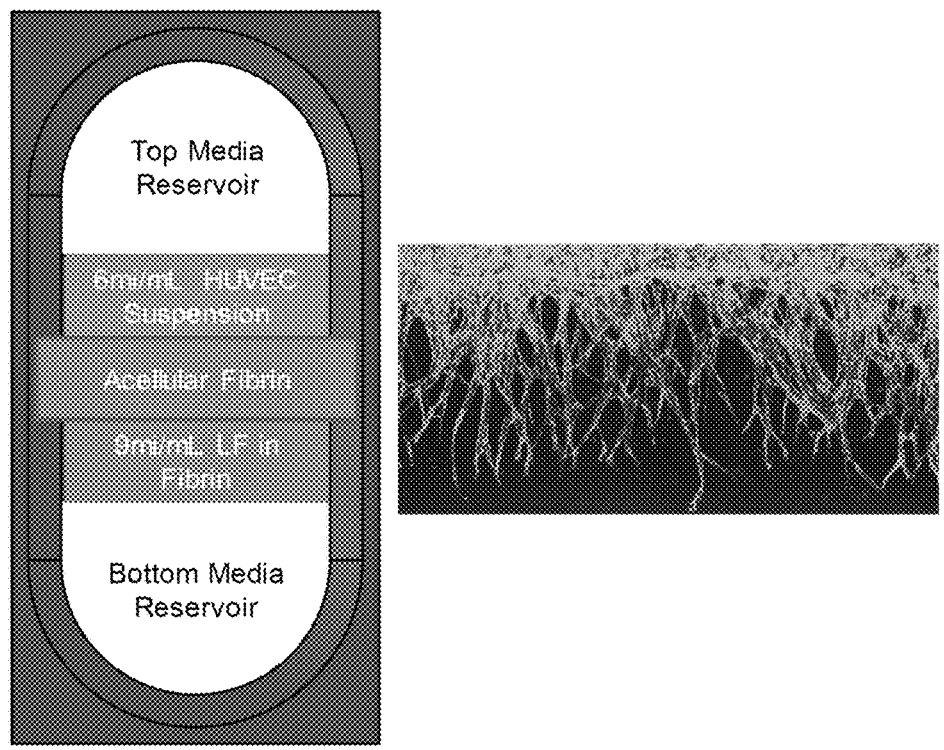
FIGS. 40C and 40D illustrate flow-induced angiogenesis using the fluid-patterned microfluidic device shown in FIGS. 39A and 39B.
Figure 40D:
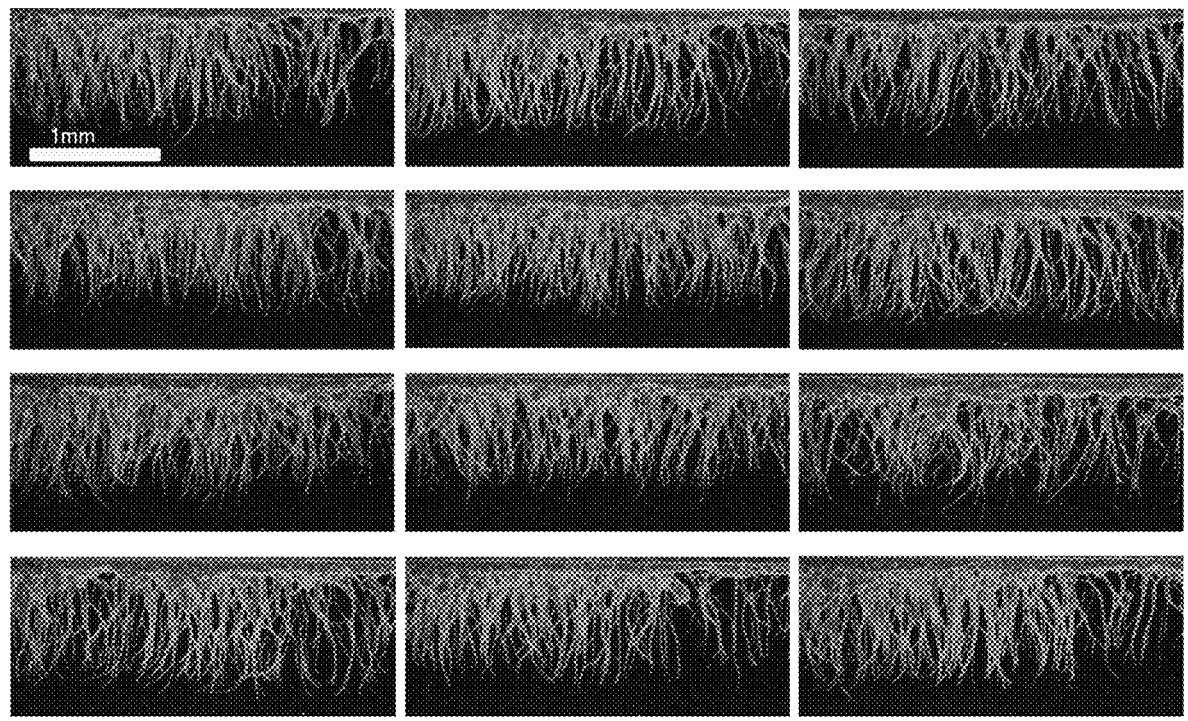

FIGS. 40C and 40D illustrate flow-induced angiogenesis using the fluid-patterned microfluidic device shown in FIGS. 39A and 39B. First, HUVECs were added at the concentration of 6 mi/mL (example volume 2 µL). Then, the culture medium is added to only one reservoir (e.g., the bottom media reservoir) and the microfluidic device was tilted 90 degrees so that the culture medium flows from the bottom media reservoir to the top media reservoir. FIG. 40C shows that the flow induced angiogenesis sprouts in the direction opposite to the direction of the flow (e.g., toward the bottom media reservoir). FIG. 40D shows the results of flow induced angiogenesis in 12 different wells, which shows the consistency in the flow induced angiogenesis.

Figure 40E:
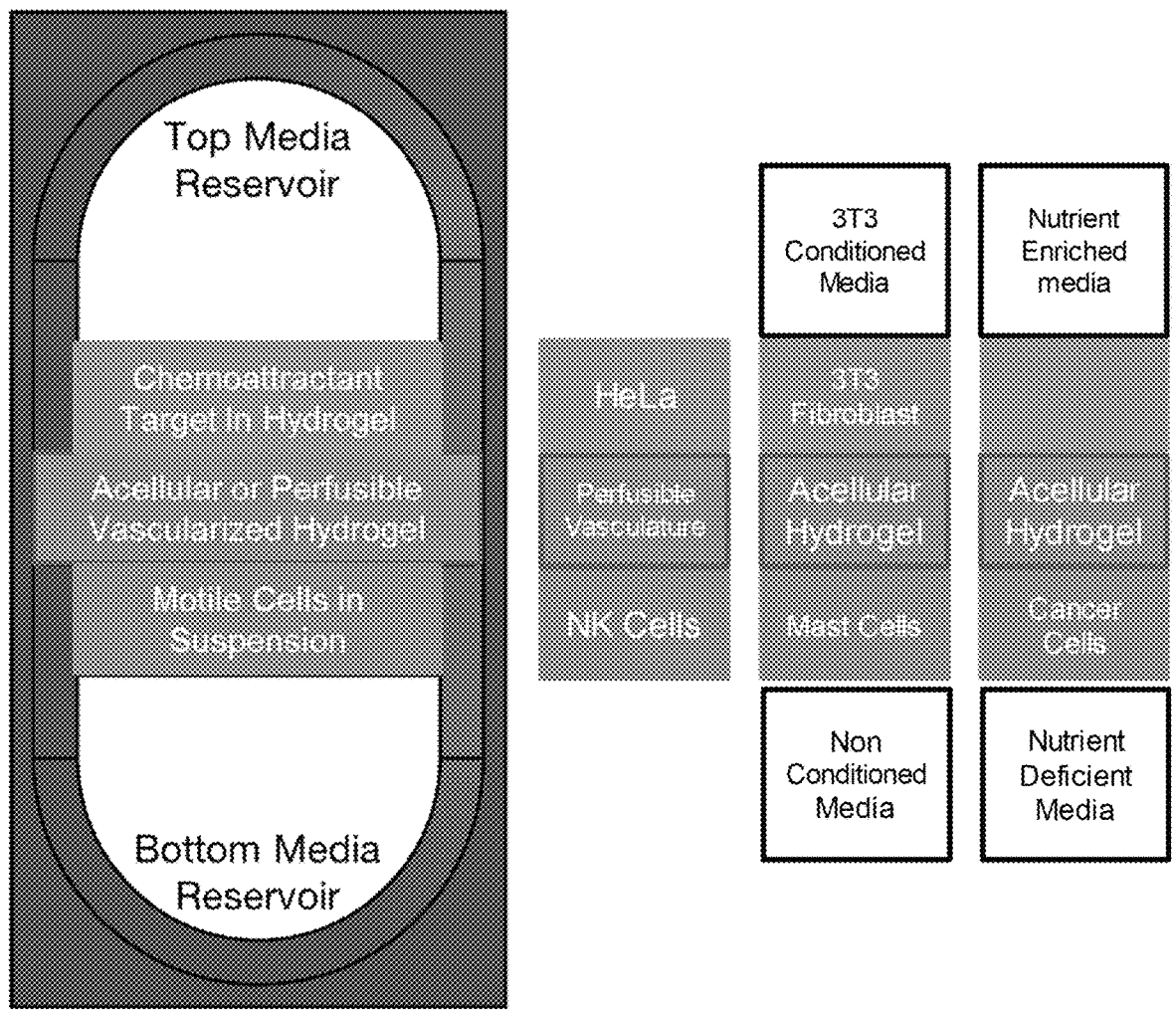
FIG. 40E illustrates example assays that may be performed using the fluid-patterned microfluidic device shown in FIGS. 39A and 39B.

FIG. 40E illustrates example assays (e.g., migratory assays) that may be performed using the fluid-patterned microfluidic device shown in FIGS. 39A and 39B. In some embodiments, the first fluid includes acellular or perfusible vascularized hydrogel, the second fluid includes chemoattractant target in hydrogel, and the third fluid includes motile cells in suspension. In some embodiments, the first fluid includes perfusible vasculature, the second fluid includes HeLa cells, and the third fluid includes NK cells. In some embodiments, the first fluid includes acellular hydrogel, the second fluid includes 3T3 fibroblast cells, and the third fluid includes mast cells. In some embodiments, the reservoir adjacent to the 3T3 fibroblast cells is filled with 3T3 conditioned media. In some embodiments, the first liquid includes acellular hydrogel, and the third fluid includes cancer cells. In some embodiments, the reservoir located adjacent to the third fluid includes nutrient deficient media, and the reservoir located away from the third fluid includes nutrient enriched media.

Figure 41A:
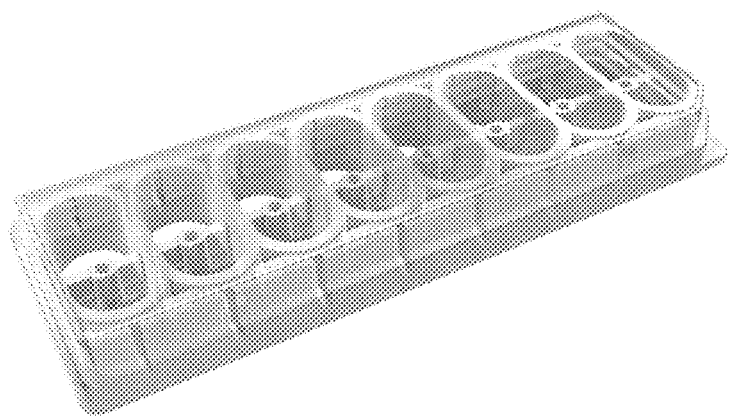
FIGS. 41A and 41B illustrate a microfluidic device in accordance with some embodiments.
Figure 41B:
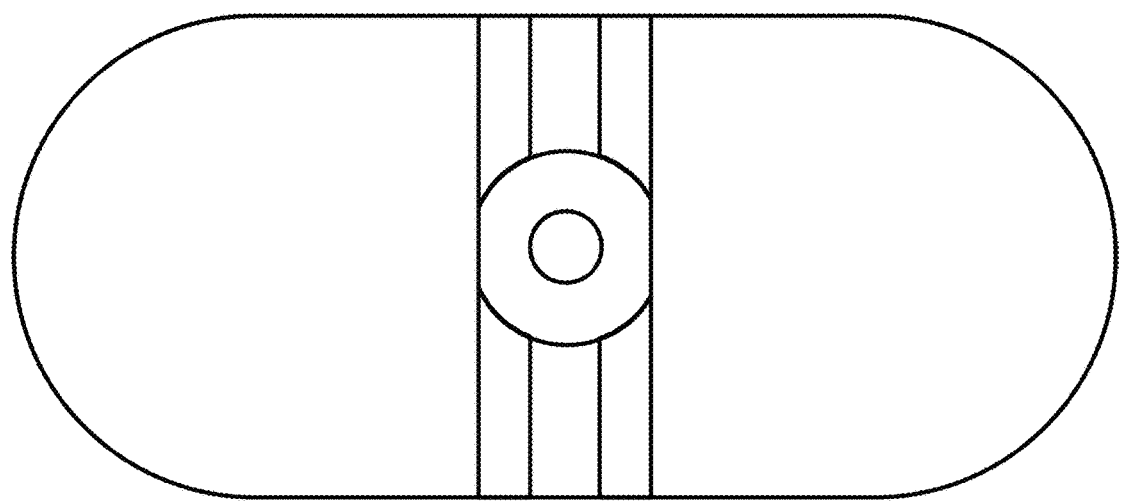
Figure 41C:
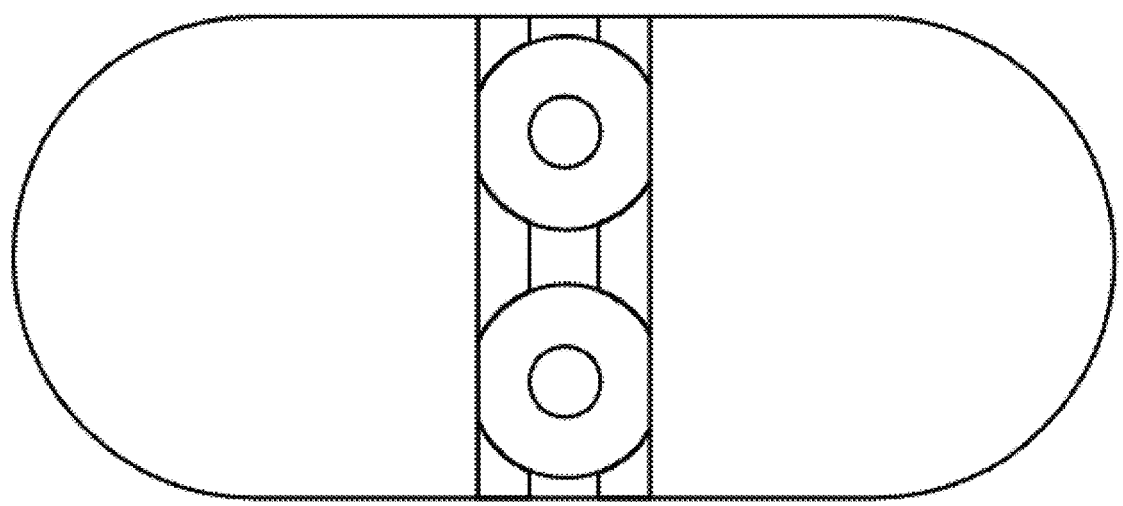
FIG. 41C illustrates a microfluidic device in accordance with some embodiments.

FIGS. 41A and 41B illustrate a microfluidic device in accordance with some embodiments. FIG. 41A is a perspective view of the microfluidic device in accordance with some embodiments. In FIG. 41A, eight wells are formed in a single plate. FIG. 41B shows a bottom view of the microfluidic device. As shown in FIGS. 41A and 41B, a beam in a respective well defines a through-hole. However, in some embodiments, the beam in a respective well defines two or more through-holes as shown in FIG. 41C. In some embodiments, two or more through-holes are defined in separate beams in a common well. In some embodiments, a single beam has indentations to define two or more microfluidic channels.

Figure 41D:
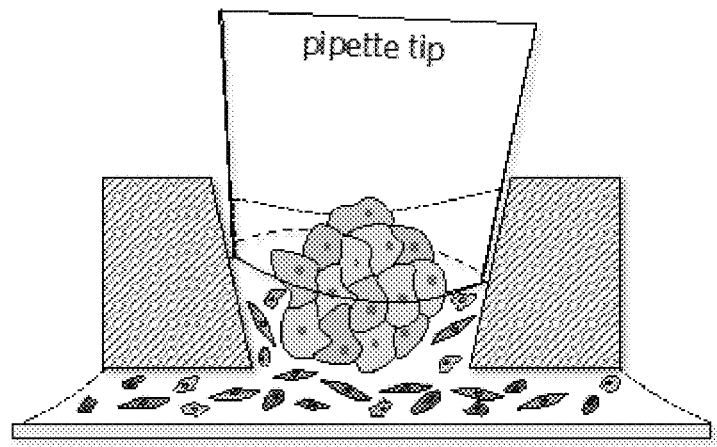
FIGS. 41D-41F are schematic diagrams illustrating a three dimensional cell culture formed by using the microfluidic device shown in FIGS. 41A and 41B.
Figure 41E:
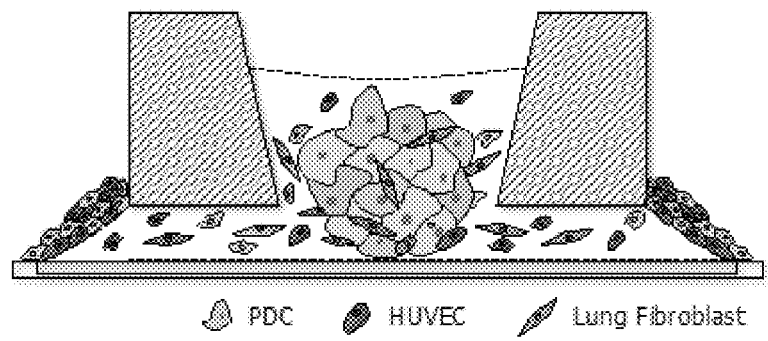
Figure 41F:
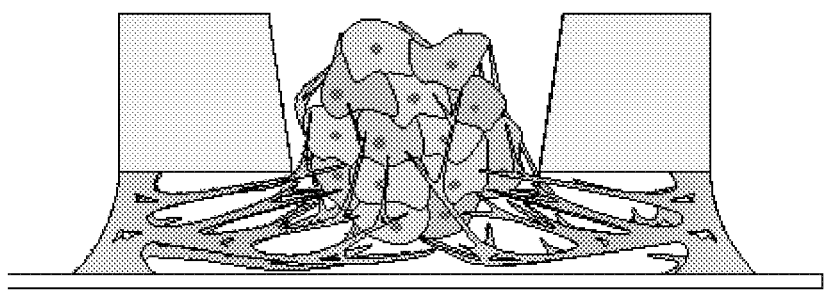

FIGS. 41D-41F are schematic diagrams illustrating a three-dimensional cell culture formed by using the microfluidic device shown in FIGS. 41A and 41B. As shown in FIG. 41D, a tip of a pipette containing a solution with a spheroid is placed adjacent to (e.g., at least partially into) the through-hole defined in the beam and the solution is dispensed from the pipette. This allows positioning of the spheroid in a proximity to a center of a projection of the through-hole onto a substrate on which the microfluidic device is mounted. In addition, the dispensed solution flows along one or more microfluidic channels defined by the beam of the microfluidic device. Thus, the microfluidic device shown in FIGS. 41A and 41B allows a one-step patterning (of the microfluidic channels) combined with placement of the spheroid within the microfluidic channels. This eliminates the need for separate operational steps for patterning of the microfluidic channels and positioning the spheroid within the microfluidic channels.

Figure 41G:
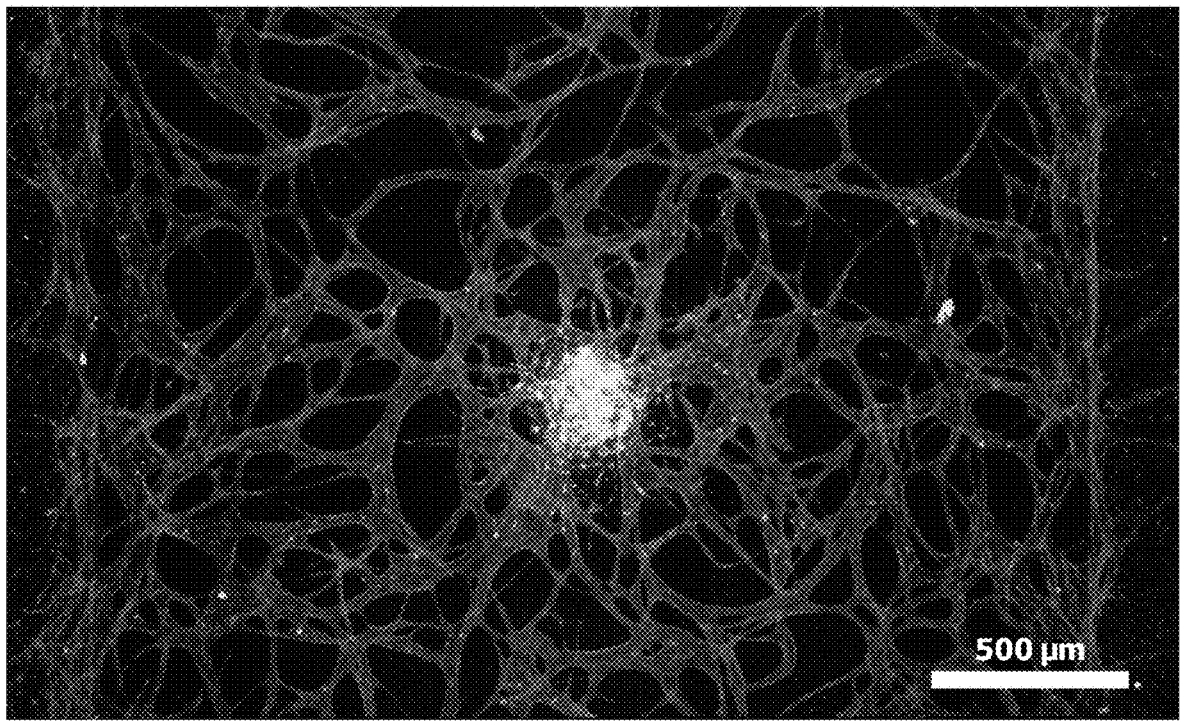
FIGS. 41G and 41H illustrate formation of vascularized cancer spheroid using the microfluidic device shown in FIGS. 41A and 41B in accordance with some embodiments.
Figure 41H:
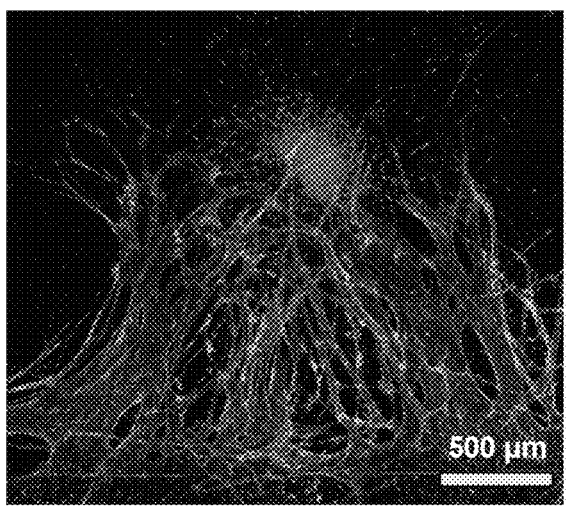

FIGS. 41G and 41H illustrate formation of vascularized cancer spheroid using the microfluidic device shown in FIGS. 41A and 41B in accordance with some embodiments. FIG. 41G shows a vascularized patient-derived gastric cancer spheroid formed on the microfluidic device by dispensing a solution including a patient-derived gastric cancer spheroid, HUVECs at 8 mi/mL, and fibroblasts at 2 mi/mL. FIG. 41B shows angiogenesis from the vascularized patient-derived gastric cancer spheroid, observed from the spheroid after 13 days of culture.

Figure 42:
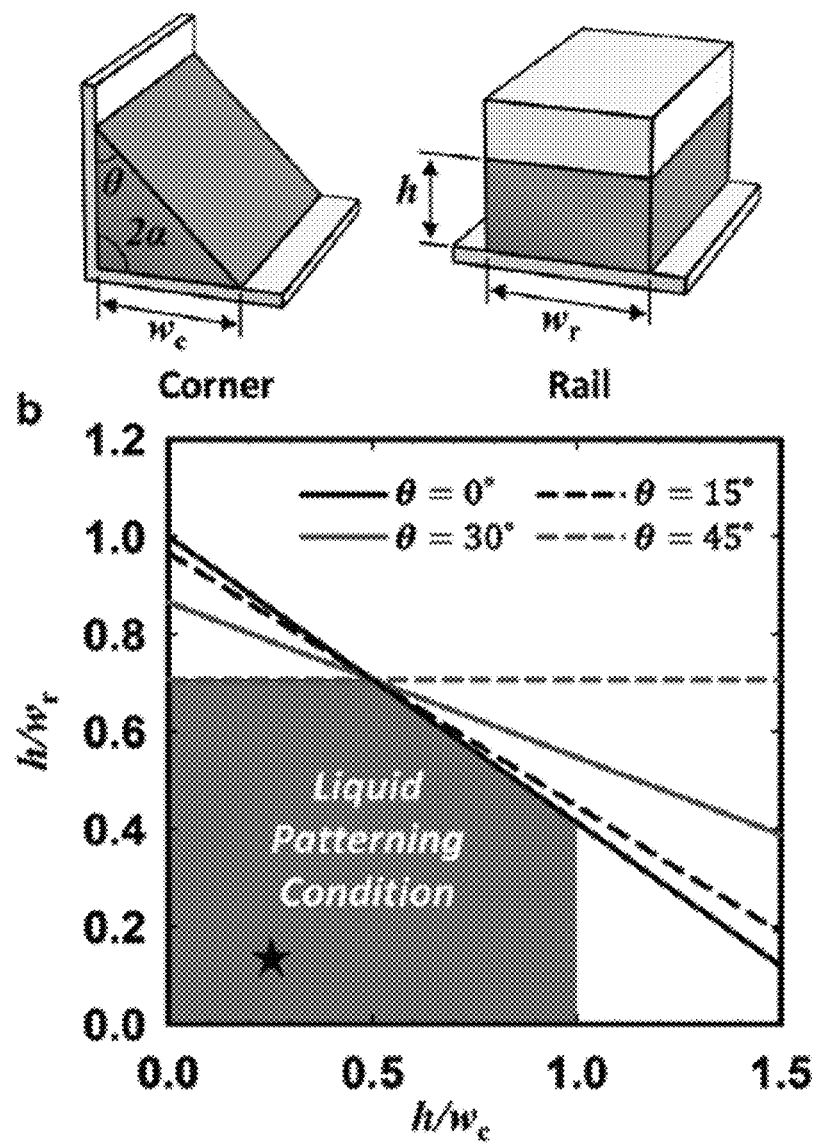
FIG. 42 illustrates liquid patterning conditions for a microfluidic device with a 90-degree side wall in accordance with some embodiments.

FIG. 42 illustrates liquid patterning conditions for a microfluidic device with a 90-degree side wall in accordance with some embodiments. In particular, whether a fluid following an inner corner path of a well enters into a microfluidic channel defined by a beam depends at least in part on the dimensions of the microfluidic device and the amount of the fluid. For example, when the height h of the microfluidic channel is larger compared to the width $w_r$ of the microfluidic channel or the width $w_c$ of the liquid on the inner corner path, the fluid may not successfully fill the microfluidic channel. In some embodiments, whether a fluid following an inner corner path of a well enters into a microfluidic channel defined by a beam also depends on the contact angle θ of the fluid relative to the substrate, as shown in the chart in FIG. 42.

Figure 43A:
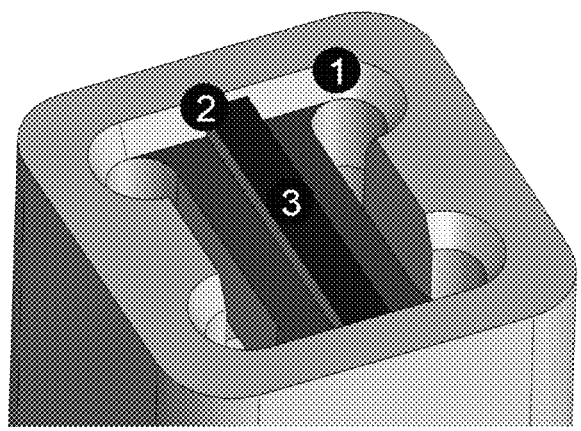
FIGS. 43A-43D illustrate liquid patterning conditions for a microfluidic device with chamfered side walls in accordance with some embodiments.
Figure 43A:
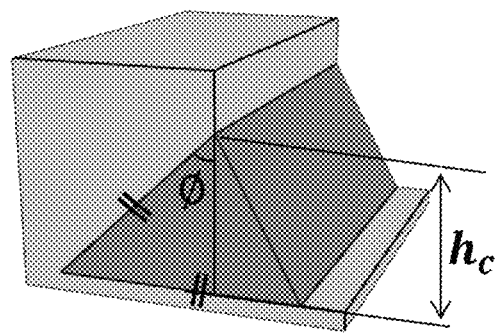
Figure 43A:
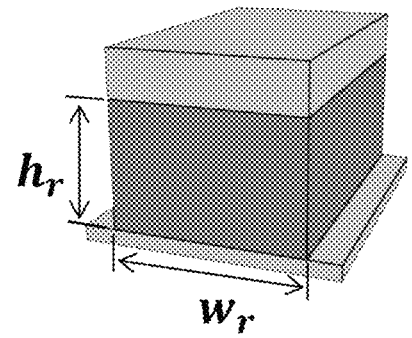

FIGS. 43A-43D illustrate liquid patterning conditions for a microfluidic device with chamfered side walls in accordance with some embodiments. The microfluidic device shown in FIG. 43A is similar to the microfluidic device shown in FIGS. 39A-39D in that its side walls are chamfered. Three regions within the microfluidic device shown in FIG. 43A that are relevant to determining whether a fluid following an inner corner path will enter a microfluidic channel for the first patterning are (1) a high corner region (with a chamfered side and an open top), (2) a low corner region (with a chamfered side and a closed top), and (3) a low rail region (with a closed top with open sides). As shown in FIG. 43A, the pressure $\Delta P_c$ of a fluid following a chamfered inner corner is determined based on the height $h_c$ of the fluid in the chamfered inner corner, the chamfer angle Φ, and the contact angle θ of the fluid. In addition, the pressure $\Delta P_r$ of a fluid filling the low rail region (e.g., the microfluidic channel) is determined based on the height $h_r$ of the low rail region, the width $w_r$ of the low rail region, and the contact angle θ of the fluid. Generally, the fluid would spontaneously flow from the high corner region (1) to the low corner region (2).

Figure 43B:
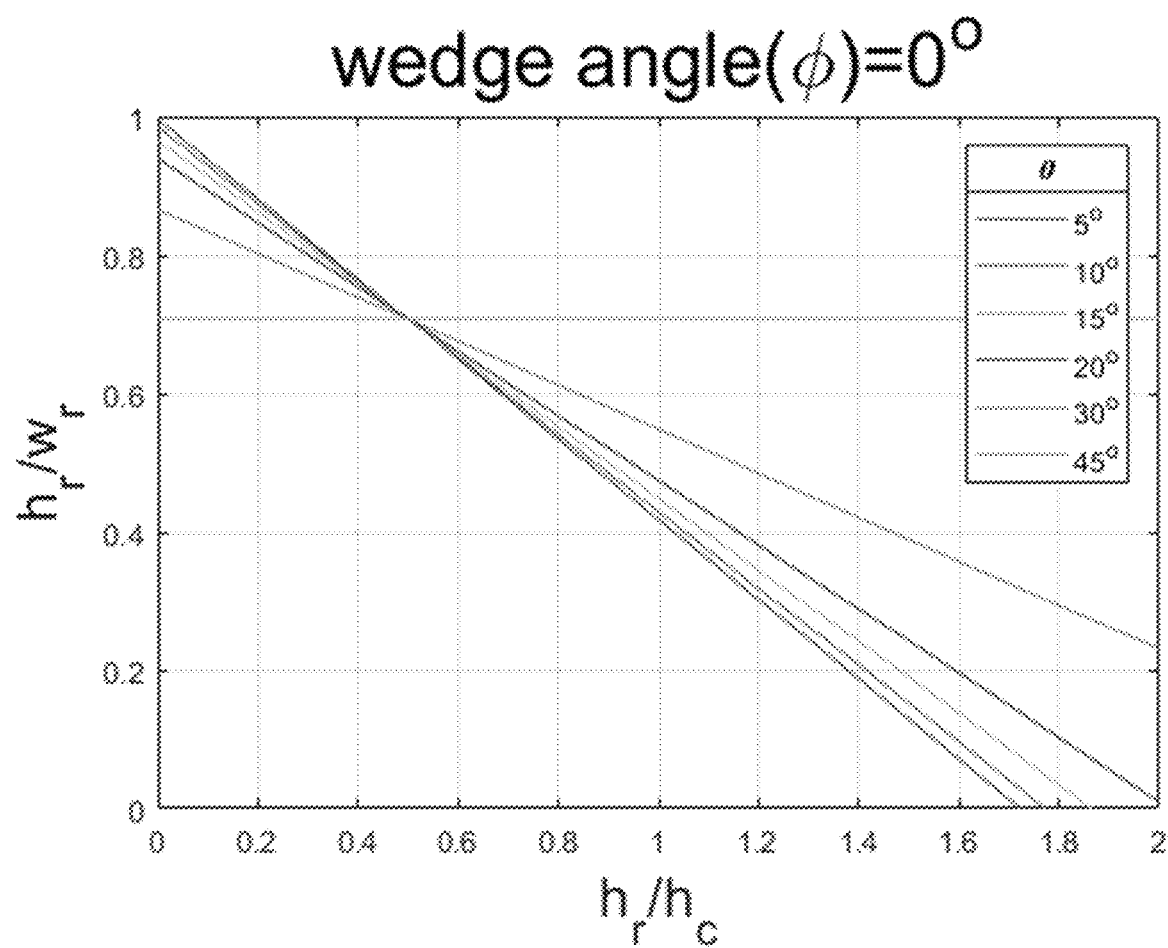
Figure 43B:
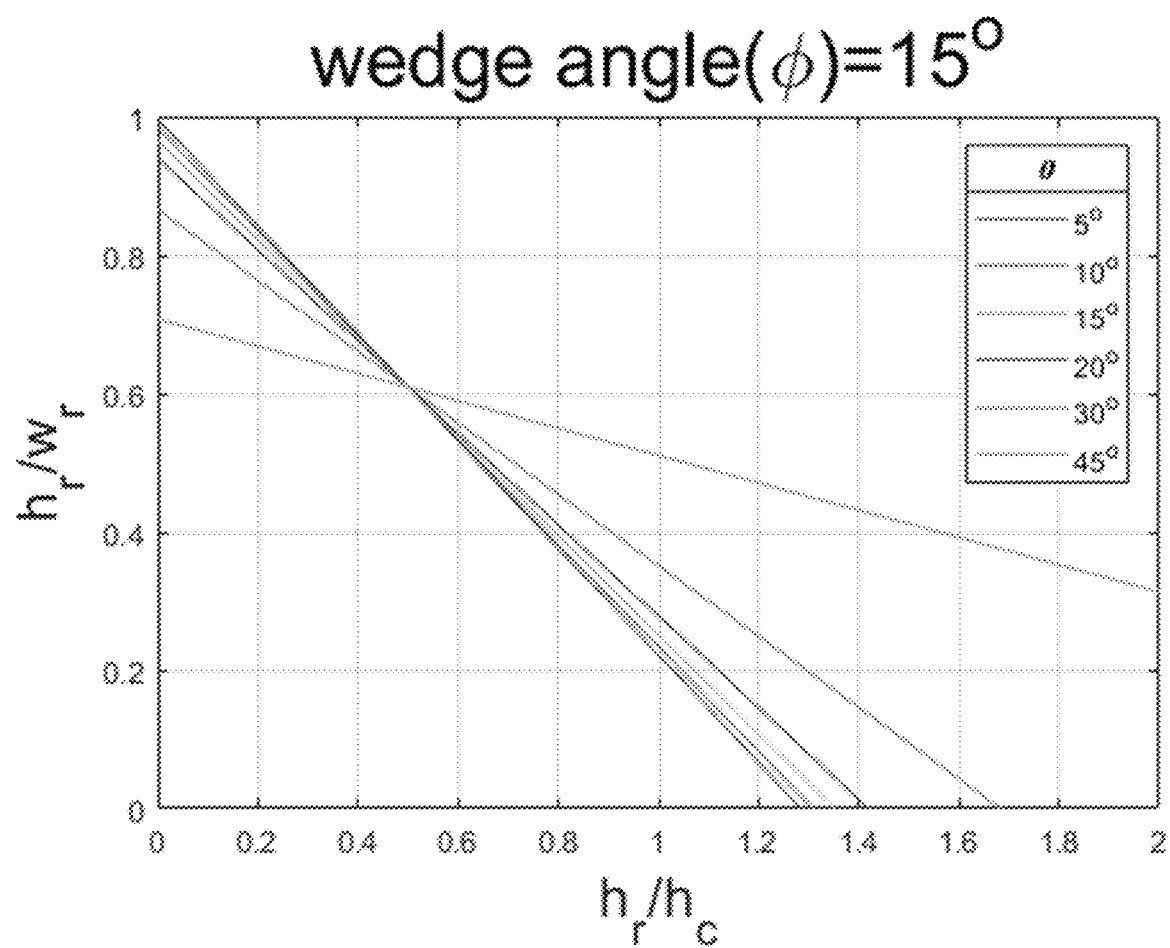
Figure 43B:
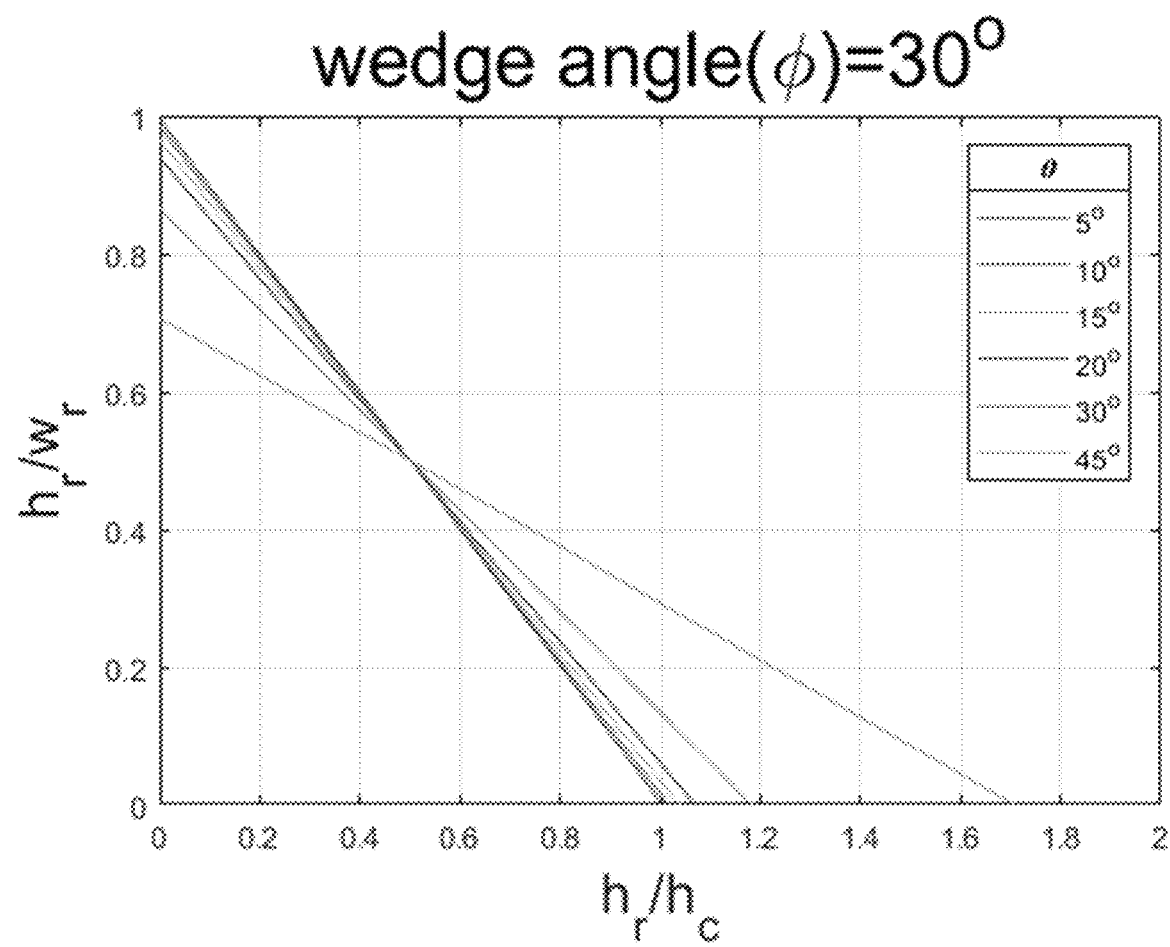
Figure 43B:
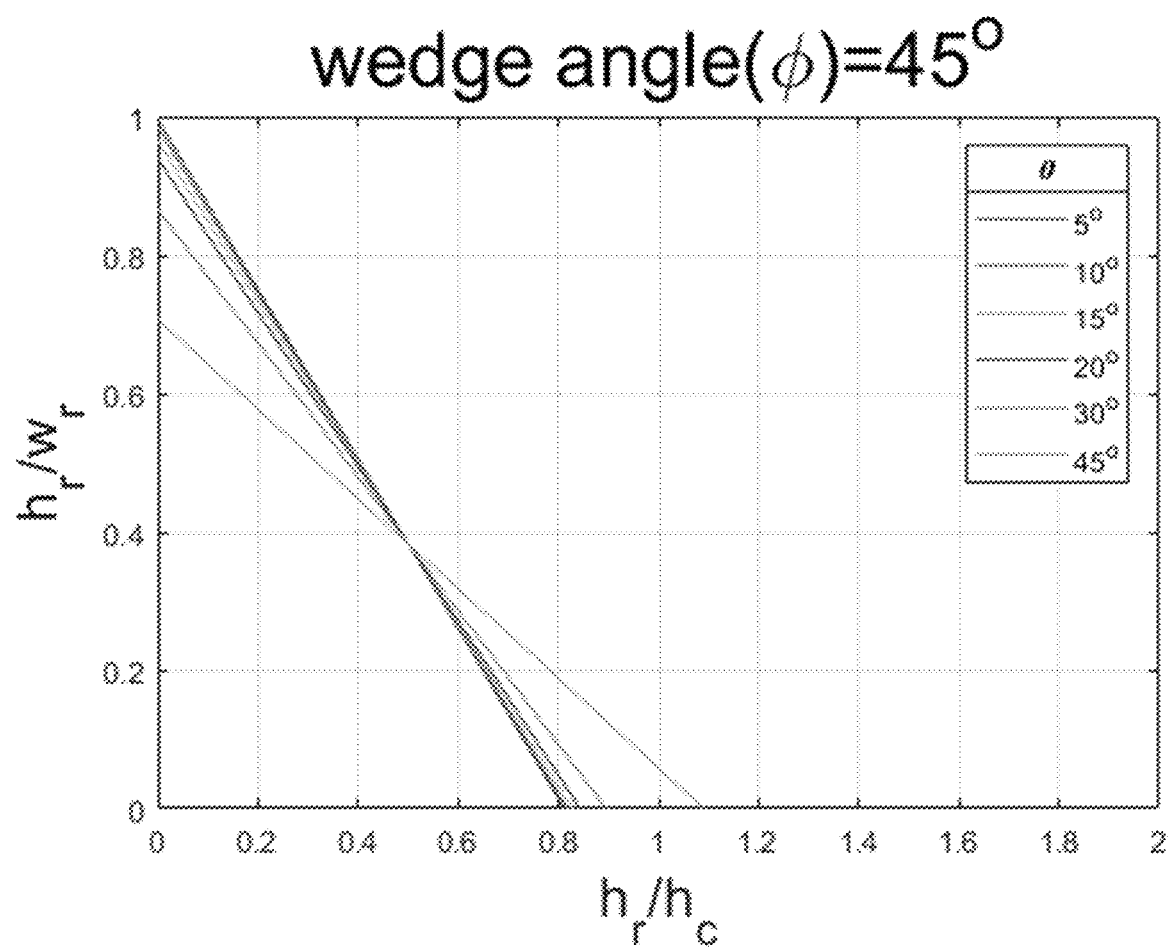
Figure 43B:
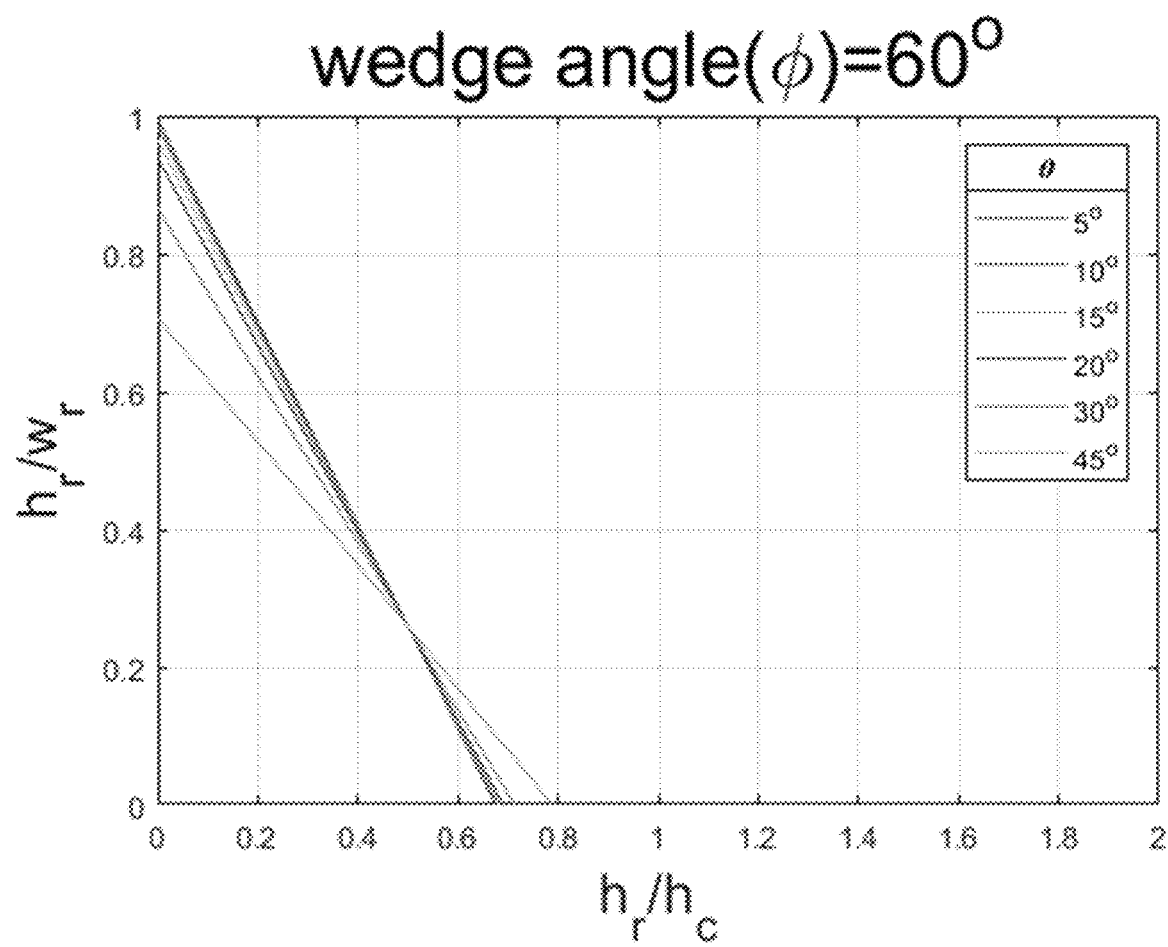
Figure 43B:
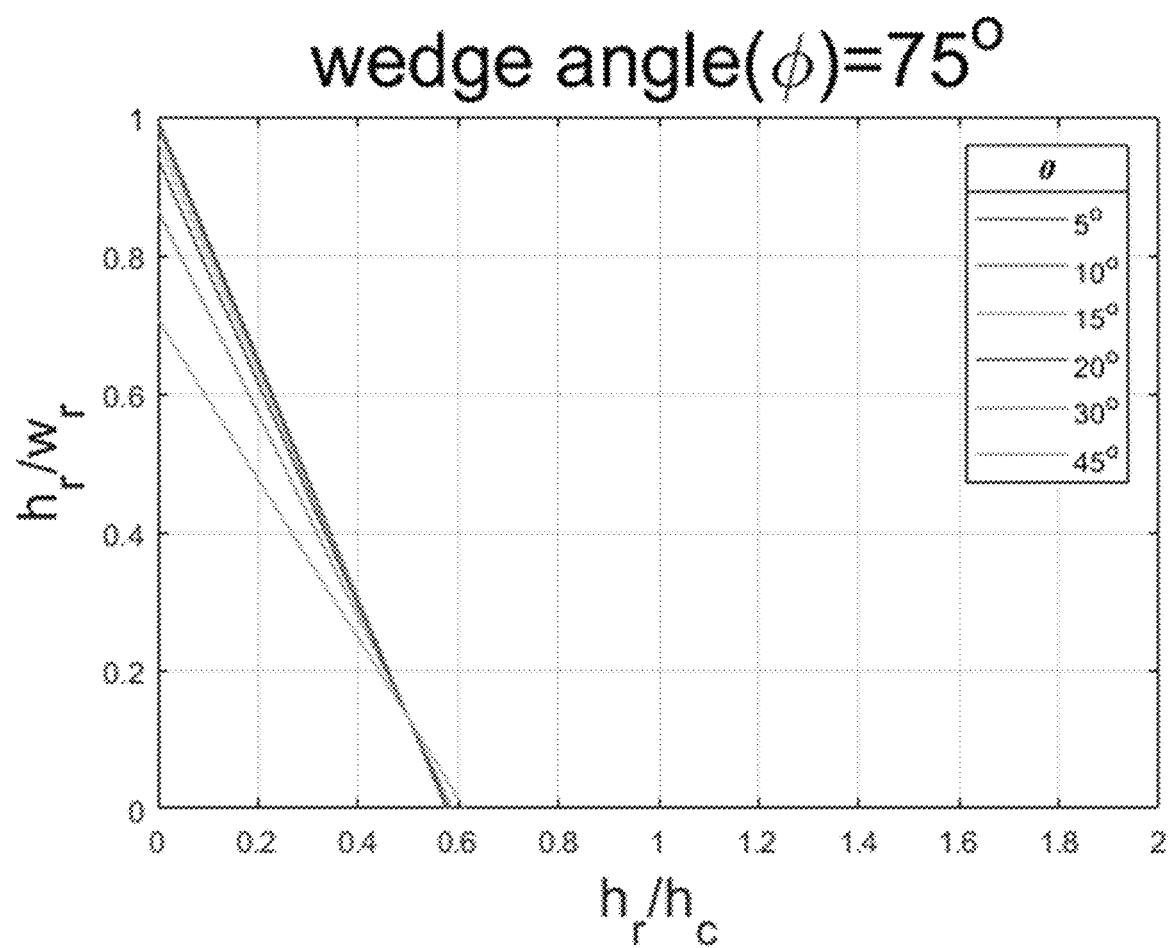

However, the fluid would flow from the low corner region (2) to the low rail region (3) only if the ratio of the height $h_r$ of the low rail region and the width $w_r$ of the low rail region, the ratio of the height $h_r$ of the low rail region and the height $h_c$ of the fluid in the chamfered inner corner, the wedge angle Φ, and the contact angle θ of the fluid satisfy patterning condition (e.g., the condition shown in FIG. 43B). For example, a microfluidic device with $h_r/w_r$ of 0.4 and a wedge angle Φ of 0° allows the fluid to flow from the low corner region (2) to the low rail region (3) when $h_r/h_c$ is 1, while a microfluidic device with $h_r/w_r$ of 1 and a wedge angle Φ of 0° does not allow the fluid to flow from the low corner region (2) to the low rail region (3) when $h_r/h_c$ is 1. In addition, a microfluidic device with a wedge angle Φ of 60° and $h_r/h_c$ of 1 does not allow the fluid to flow from the low corner region (2) to the low rail region (3) regardless of the value of $h_r/w_r$. Thus, increased the wedge angle Φ improves the selectivity in fluid patterning. In addition, FIG. 43B also shows that when the wedge angle Φ is high (e.g., Φ>45°), the effect of the contact angle θ on the patterning condition is reduced.

Figure 43C:
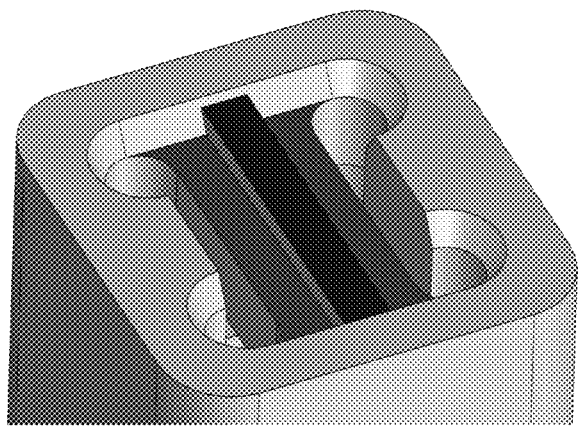
Figure 43C:
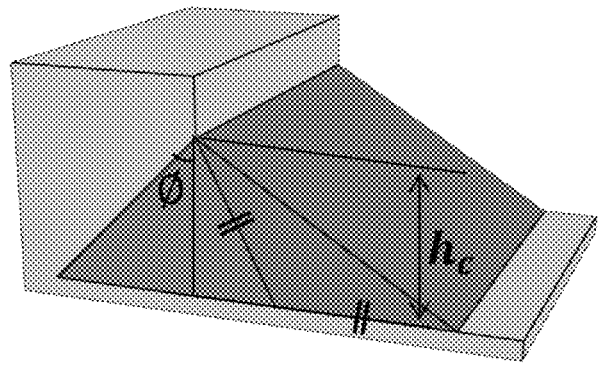
Figure 43C:
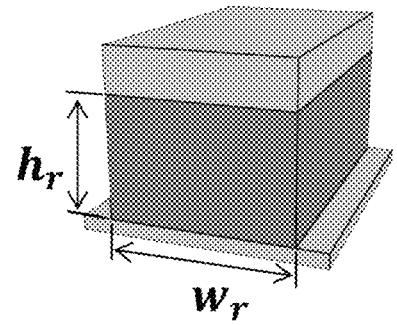
Figure 43D:
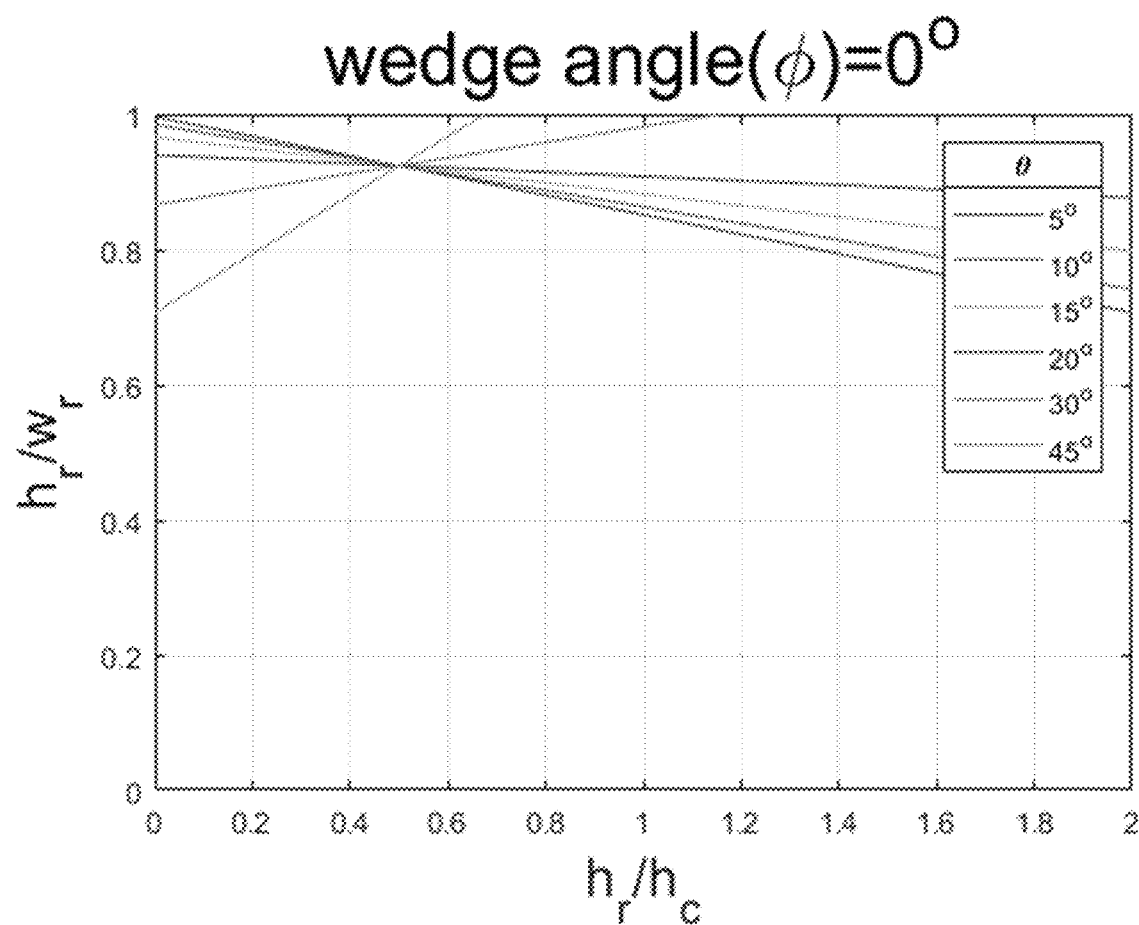
Figure 43D:
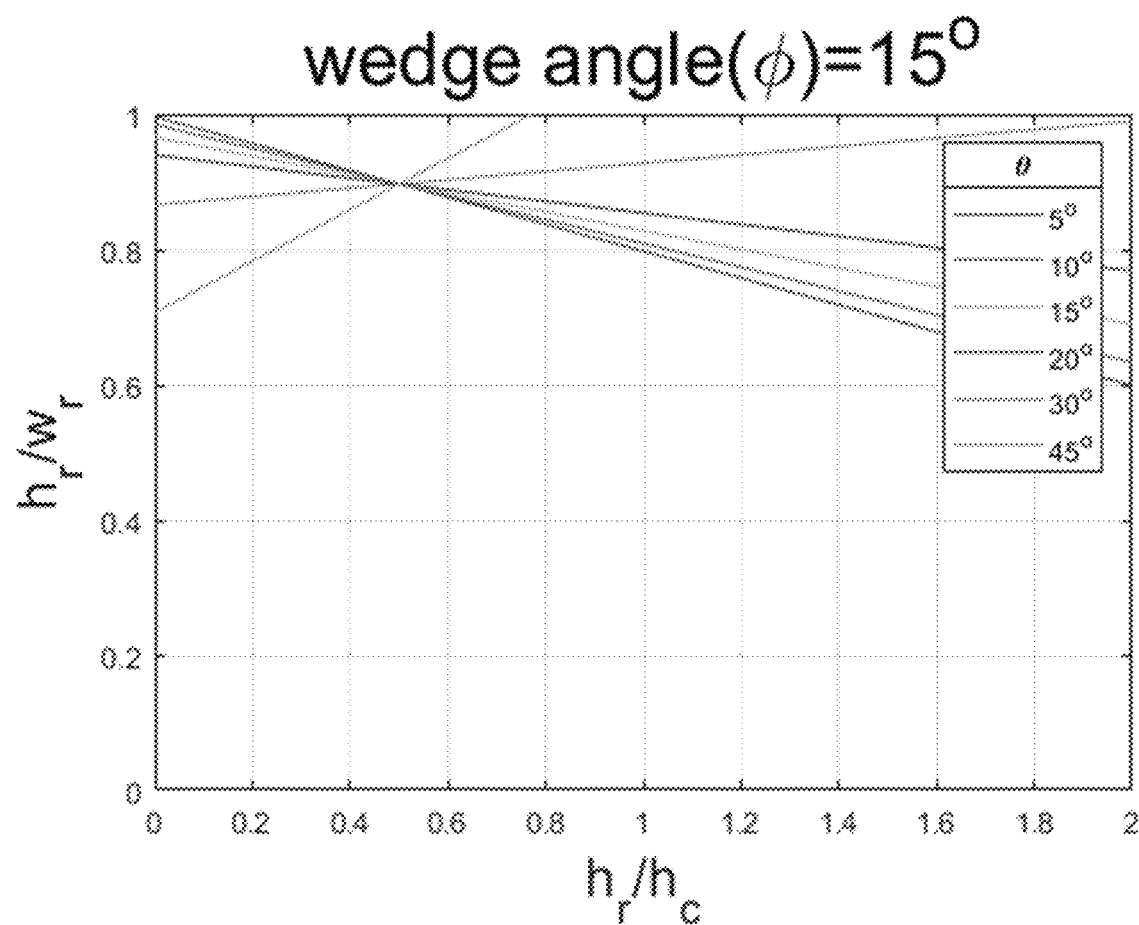
Figure 43D:
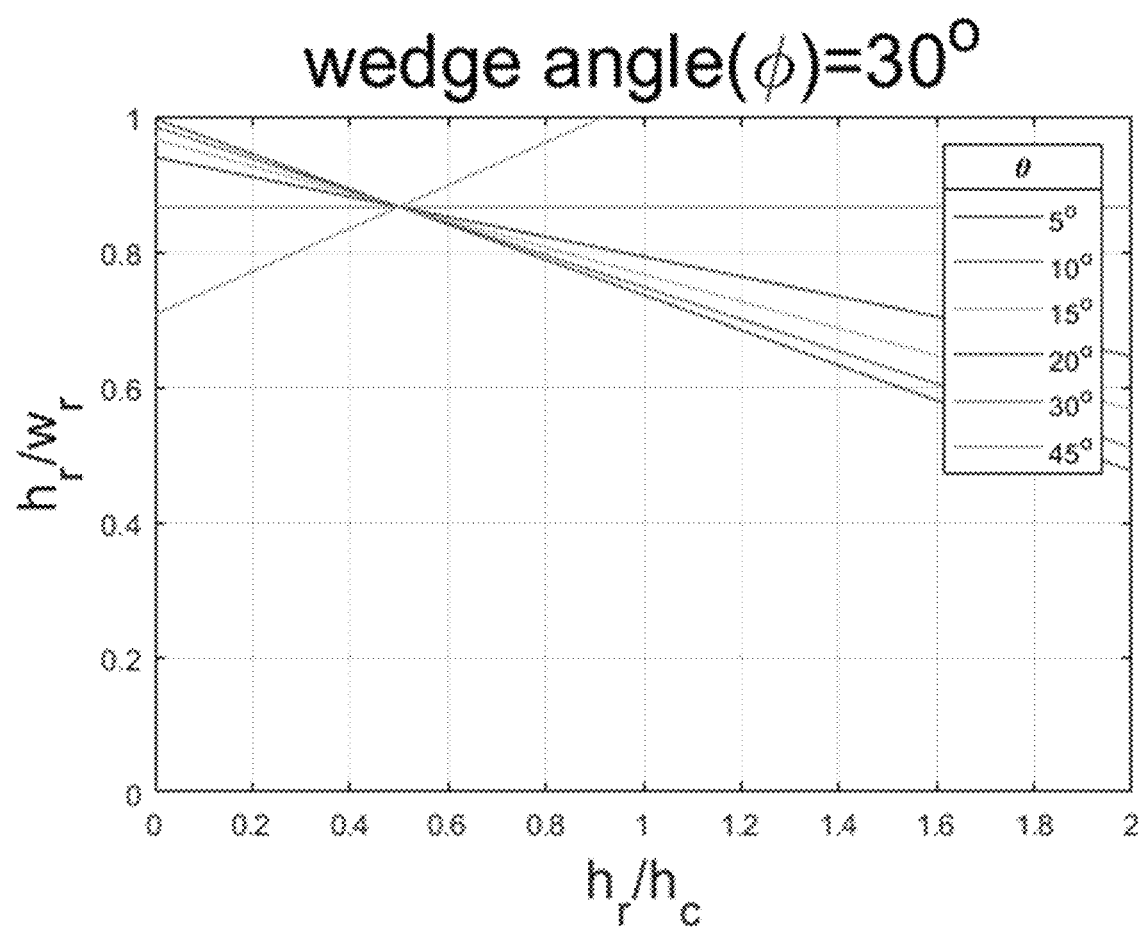
Figure 43D:
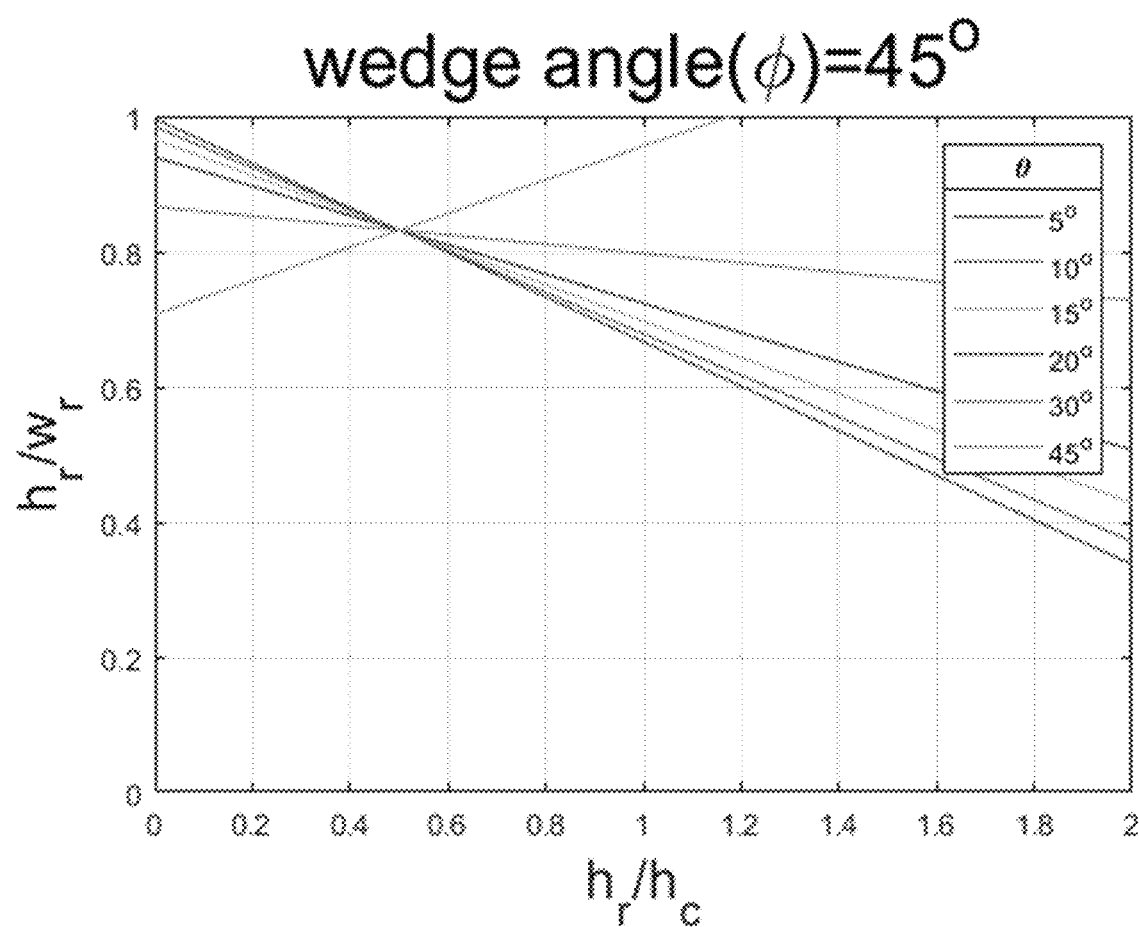
Figure 43D:
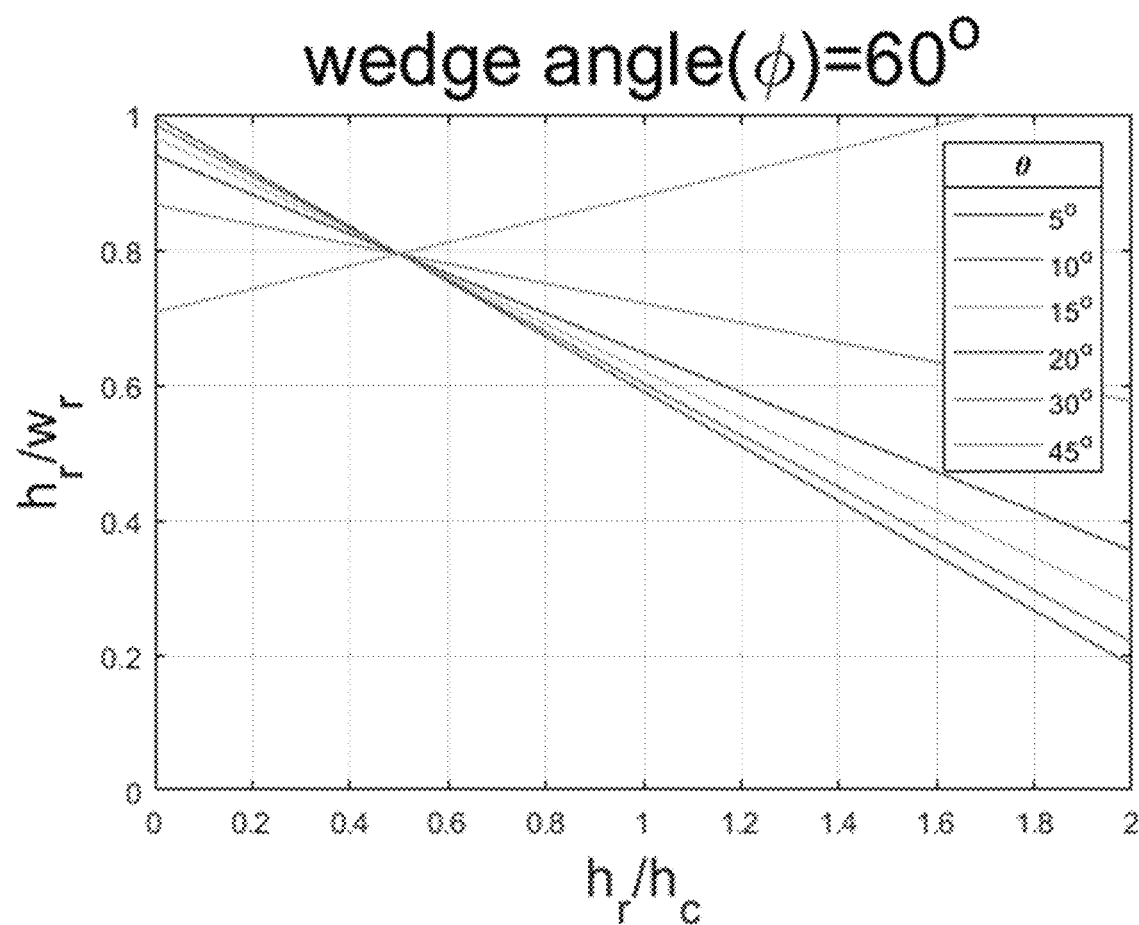
Figure 43D:
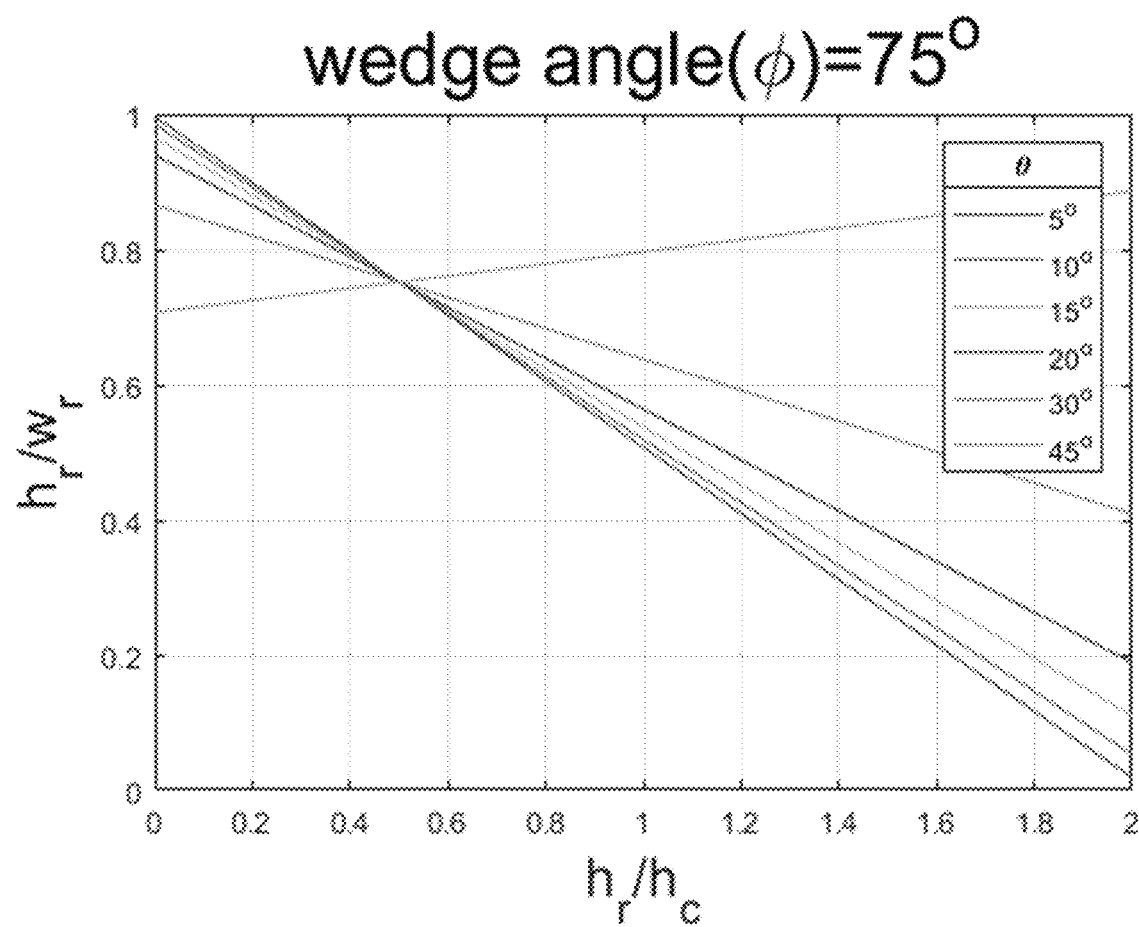

As shown in FIG. 43C, two regions within the microfluidic device that are relevant to determining whether a fluid following an inner corner path will enter a microfluidic channel for the second patterning are (1) a high corner region (with a chamfered side and an open top) and (2) a high rail region (with a closed top with open sides). As shown in FIG. 43C, the pressure $\Delta P_c$ of a fluid following a chamfered inner corner is determined based on the height $h_c$ of the fluid in the chamfered inner corner, the chamfer angle Φ, and the contact angle θ of the fluid. In addition, the pressure $\Delta P_r$ of a fluid filling the low rail region (e.g., the microfluidic channel) is determined based on the height $h_r$ of the low rail region, the width $w_r$ of the low rail region, and the contact angle θ of the fluid. Because the first fluid will be in contact with the chamfered side wall, particular dimensions of the microfluidic device may allow the first fluid to flow into the microfluidic channel (under the low rail) but may not allow the second fluid to flow into the microfluidic channel (under the high rail). Thus, in some cases, a configuration that satisfies both the patterning condition for the first patterning and the patterning condition for the second patterning is used to allow both the first patterning and the second patterning.

As shown above, the chamfered (or slanted) side walls facilitate multiple paths of patterning along the side walls. In some embodiments, patterning fluids are passed along an inner corner path twice (e.g., a first fluid is passed along the inner corner path and subsequently, a second fluid is passed along the inner corner path). In some embodiments, patterning fluids are passed along the inner corner path three or more times (e.g., three or more different fluids are sequentially passed along the inner corner path).

In light of these principles and examples, we turn to certain embodiments.

In accordance with some embodiments, a device includes a substrate (e.g., substrate 320) having a top surface and a bottom surface opposite to the top surface; and one or more beams. A respective beam of the one or more beams (e.g., microfluidic channel module 220) has a bottom surface facing the top surface of the substrate and a top surface opposite to the bottom surface of the respective beam facing away from the top surface of the substrate. The respective beam is positioned adjacent to the substrate. At least a portion of the respective beam is spaced apart from the top surface of the substrate to define one or more microfluidic channels to enable movement of a fluid by capillary force between the bottom surface of the respective beam and the top surface of the substrate along the one or more microfluidic channels. In some embodiments, the bottom surface of the respective beam is hydrophilic. In some embodiments, the top surface of the substrate is hydrophilic.

In some embodiments, the one or more beams include a beam having an indented bottom surface (e.g., the microfluidic channel module 220 in FIG. 2). The indented bottom surface includes a first linear portion, a second linear portion, and a third linear portion. The second linear portion is located between the first linear portion and the third linear portion. The first linear portion is separated from the substrate by a first distance. The second linear portion is separated from the substrate by a second distance that is distinct from the first distance. The third linear portion is separated from the substrate by a third distance that is distinct from the second distance.

In some embodiments, the second distance is greater than the first distance and the third distance (e.g., the microfluidic channel module 220 in FIG. 2).

In some embodiments, the second linear portion of the beam includes one or more through-holes that extend from the second linear portion of the indented bottom surface to the top surface of the beam (e.g., through-holes 231 in FIG. 1).

In some embodiments, the second distance is greater than the first distance and the third distance is greater than the second distance (e.g., FIG. 4).

In some embodiments, the one or more beams include two or more beams that are separated from each other. In some embodiments, the device includes two beams that correspond to the first linear portion of the beam and the third linear portion of the beam without the second linear portion of the beam connecting the first linear portion of the beam to the third linear portion of the beam.

In some embodiments, a respective beam of the two or more beams has an indented bottom surface, the indented bottom surface including a first linear portion, a second linear portion, and a third linear portion. The second linear portion is located between the first linear portion and the third linear portion. The first linear portion is separated from the substrate by a first distance. The second linear portion is separated from the substrate by a second distance that is distinct from the first distance. The third linear portion is separated from the substrate by a third distance that is distinct from the second distance. For example, as shown in FIG. 5, the device includes multiple beams.

In some embodiments, the second distance is greater than the first distance and the third distance.

In some embodiments, the second distance is greater than the first distance and the third distance is greater than the second distance.

In some embodiments, the two or more beams include a first beam and a second beam that is substantially parallel to the first beam.

In some embodiments, the device includes one or more side walls located adjacent to the substrate.

In some embodiments, the one or more beams extend from the one or more side walls (e.g., side wall 310).

In some embodiments, the one or more side walls are in contact with the substrate. A respective side wall of the one or more side walls defines a path corresponding to a contact between the substrate and the respective side wall (e.g., inner corner path 340).

In some embodiments, the respective side wall and the substrate define an angle that is 90 degrees (e.g., the respective side wall is perpendicular to the substrate, as shown in FIG. 42).

In some embodiments, the respective side wall and the substrate define an angle that is less than 90 degrees. For example, the respective side wall may be inclined relative to the substrate (e.g., the respective side wall and the substrate define an angle that is between 80 and 90 degrees, between 70 and 80 degrees, between 60 and 70 degrees, between 50 and 60 degrees, between 40 and 50 degrees, between 30 and 40 degrees, between 20 and 30 degrees, etc.).

In some embodiments, a portion of the respective side wall of the one or more side walls is chamfered. In some embodiments, the chamfered portion of the respective side wall is in contact with the substrate and the chamfered portion and the substrate define an angle that is less than 90 degrees (e.g., FIG. 43A). For example, the chamfered portion satisfies the patterning condition described with respect to FIGS. 43B and 43D.

In some embodiments, the one or more side walls include a first side wall and a second side wall. In some embodiments, the second side wall is separated from the first side wall. The one or more beams include a first beam that extends from the first side wall and a second beam that extends from the second side wall.

In some embodiments, the one or more beams include a first beam and a second beam that is separate from the first beam. The first beam extends from a first wall location on a first side wall of the one or more side walls. The second beam extends from a second wall location on the first side wall that is distinct from the first wall location. The first side wall defines a first through-hole between (i) a first corner location that is located on the first side wall below the first wall location adjacent to a contact between the first side wall and the substrate and (ii) a second corner location that is located on the first side wall below the second wall location adjacent to a contact between the first side wall and the substrate.

In some embodiments, the first beam extends to a third wall location that is distinct from the first wall location and the second wall location. The second beam extends to a fourth wall location that is distinct from the first wall location, the second wall location, and the third wall location. The one or more side walls define a second through-hole between (i) a third corner location that is located on the one or more side walls below the third wall location adjacent to a contact between the one or more side walls and the substrate and (ii) a fourth corner location that is located on the one or more side walls below the fourth wall location adjacent to a contact between the one or more side walls and the substrate.

In some embodiments, a respective beam of the two or more beams has an indented bottom surface, the indented bottom surface including a first linear portion, a second linear portion, and a third linear portion. The second linear portion is located between the first linear portion and the third linear portion. The first linear portion is separated from the substrate by a first distance. The second linear portion is separated from the substrate by a second distance that is greater than the first distance. The third linear portion is separated from the substrate by a third distance that is less than the second distance. The first linear portion extends from a first wall location on a first side wall of the one or more side walls. The third linear portion extends from a second wall location on the first side wall that is distinct from the first wall location. The first side wall defines a first through-hole (e.g., stopper portion 602) between (i) a first corner location that is located on the first side wall below the first wall location adjacent to a contact between the first side wall and the substrate and (ii) a second corner location that is located on the first side wall below the second wall location adjacent to a contact between the first side wall and the substrate.

In some embodiments, the first linear portion extends to a third wall location that is distinct from the first wall location and the second wall location. The third linear portion extends to a fourth wall location that is distinct from the first wall location, the second wall location, and the third wall location. The one or more side walls define a second through-hole (e.g., another stopper portion on the opposite side from stopper portion 602) between (i) a third corner location that is located on the one or more side walls below the third wall location adjacent to a contact between the one or more side walls and the substrate and (ii) a fourth corner location that is located on the one or more side walls below the fourth wall location adjacent to a contact between the one or more side walls and the substrate.

In some embodiments, the one or more side walls define one or more wells. The respective beam is coupled with a vertical divider (e.g., partition 200) to separate a respective well of the one or more wells into a first chamber on a first side of the vertical divider and a second chamber that is distinct from the first chamber, the second chamber being on a second side of the vertical divider that is opposite to the first side of the vertical divider.

In some embodiments, the bottom surface of the respective beam extends curvilinearly. For example, the respective beam is not linear (e.g., the respective beam is curved, such as forming a circle or an ellipse).

In some embodiments, the respective beam includes a hollow portion (e.g., FIG. 15), an open end of the hollow portion being positioned adjacent to the substrate. For example the respective beam has a shape of a vertical pipe, and one end of the pipe is positioned toward the substrate.

In some embodiments, the device includes one or more side walls, a respective side wall of the one or more side walls being tilted so that a first portion of the respective side wall has a first distance to the respective beam and a second portion of the respective side wall that is located above the first portion of the respective side wall has a second distance to the respective beam that is greater than the first distance to the respective beam (e.g., the side wall in FIG. 15).

In some embodiments, the device includes a plurality of pillars extending from the top surface of the substrate and positioned at respective locations below the bottom surface of the respective beam (e.g., FIG. 30). A first subset of the plurality of pillars positioned along a first linear or curvilinear path on the top surface of the substrate. In some embodiments, a second subset of the plurality of the plurality of pillars positioned along a second linear or curvilinear path on the top surface of the substrate that is distinct from the first linear or curvilinear path.

In accordance with some embodiments, a method of covering a substrate with a pattern of liquids includes flowing a liquid between the bottom surface of the respective beam of any device described herein and the top surface of the substrate of the device (e.g., FIG. 3).

In accordance with some embodiments, a method of covering a substrate with a pattern of liquids includes flowing a first liquid between the first linear portion of any device described herein and the top surface of the substrate of the device (e.g., fluid 330 in FIG. 3). The method also includes flowing a third liquid between the third linear portion of the device and the top surface of the substrate of the device (e.g., FIG. 3 or FIG. 7). In some embodiments, the third liquid is identical to the first liquid (e.g., FIG. 3). In some embodiments, the third liquid is distinct from the first liquid (e.g., FIG. 7(c)).

In some embodiments, the method includes flowing a second liquid between the second linear portion of the device and the top surface of the substrate of the device (e.g., liquid 334 in FIG. 3).

In accordance with some embodiments, a method of covering a substrate with a pattern of liquids includes flowing a first liquid between a first beam of the two or more beams of any device described herein and the top surface of the substrate of the device. The method also includes flowing a second liquid between a second beam of the two or more beams of the device and the top surface of the substrate of the device.

In accordance with some embodiments, a method of covering a substrate with a pattern of liquids. The method includes providing a first liquid to a first location on the substrate of any device described herein adjacent to the one or more side walls.

In accordance with some embodiments, a method of covering a substrate with a pattern of liquids includes providing a first liquid to a first side of the first through-hole so that the first liquid flows between the first linear portion of any device described herein and the top surface of the substrate of the device. The method includes providing a second liquid to a second side of the first through-hole that is distinct from the first side of the first through-hole so that the second liquid flows between the third linear portion of the device and the top surface of the substrate of the device (e.g., FIG. 6).

In accordance with some embodiments, a method of covering a substrate with a pattern of liquids includes providing a first liquid to a first side of the first through-hole so that the first liquid flows between the first beam of any device described herein and the top surface of the substrate of the device. The method also includes providing a second liquid to a second side of the first through-hole that is distinct from the first side of the first through-hole so that the second liquid flows between the second beam of the device and the top surface of the substrate of the device.

In some embodiments, the method includes, subsequent to providing the first liquid and the second liquid, sealing the first through-hole (e.g., FIG. 6). The method also includes, subsequent to sealing the first through-hole, providing a third liquid so that the third liquid flows between the second linear portion of the device and the top surface of the substrate of the device.

In some embodiments, the method includes providing a second liquid to a second location on the substrate of the device adjacent to the one or more side walls. The second location is distinct and separate from the first location (e.g., FIG. 7(c)).

In accordance with some embodiments, a method includes, while a first liquid remains between the first linear portion of any device described herein and the substrate, a second liquid remains between the second linear portion of the device and the substrate, and a third liquid remains between the third linear portion of the device and the substrate, providing a fourth liquid to the first chamber (e.g., fluid 904 in FIG. 9).

In some embodiments, the method includes providing a fifth liquid to the second chamber (e.g., fluid 906 in FIG. 9).

In some embodiments, the fourth liquid has a first height in the first chamber and the fifth liquid has a second height in the second chamber that is less than the first height.

In some embodiments, at least one of the first liquid, the second liquid and the third liquid includes cells.

In accordance with some embodiments, a method includes causing angiogenesis or vasculogenesis using any device described herein.

In accordance with some embodiments, a method includes causing cellular reaction using any device described herein by: providing a first liquid between the first linear portion and the substrate; providing the first liquid between the third linear portion and the substrate; providing a second liquid between the second linear portion and the substrate, the second liquid being distinct from the first liquid, the second liquid containing cells of a first type; and providing a third liquid distinct form the first liquid, the third liquid containing cells of a second type adjacent to the first linear portion so that the third liquid comes in contact with the first liquid.

In accordance with some embodiments, a method includes causing cellular reaction using any device described herein by providing a first liquid between the respective beam and the substrate; providing a second liquid in a region surrounded by the first liquid so that the second liquid comes in contact with the first liquid, the second liquid being distinct from the first liquid, the second liquid containing cells of a first type; and providing a third liquid distinct from the first liquid adjacent to the respective beam so that the third liquid comes in contact with the first liquid, the third liquid containing cells of a second type.

In some embodiments, the method includes causing angiogenesis. The first liquid contains fibrin. The cells of the first type include fibroblast cells. The cells of the second type include vascular endothelial cells (e.g., FIG. 11 and FIG. 16).

In some embodiments, the method includes causing vascular genesis. The first liquid contains vascular endothelial cells. The cells of the first type include fibroblast cells. The cells of the second type include fibroblast cells (e.g., FIG. 17).

In some embodiments, the cells of the first type include cancer cells (e.g., HeLa cells); and the cells of the second type include lymphocytes (e.g., NK cells).

In accordance with some embodiments, a method for obtaining a vascularized tumor spheroid includes placing a tumor spheroid in any device described herein. The method also includes co-culturing the tumor spheroid with fibroblast cells (e.g., FIG. 26).

In accordance with some embodiments, a method includes placing a vascularized tumor spheroid in any device described herein, and providing a liquid containing kinase inhibitor (e.g., FIG. 29).

In accordance with some embodiments, a method includes forming a three-dimensional matrix of cells with any device described herein by: providing a first liquid between the bottom surface of the respective beam and the substrate; providing a second liquid on a first side of the first liquid, the second liquid being distinct from the first liquid, the second liquid containing cells of a first type; and providing a third liquid on a second side of the first liquid that is opposite to the first side, the third liquid being distinct from the first liquid (e.g., FIG. 30).

In some embodiments, the cells of the first type include neuron cells; and the third liquid contains cells of a second type, the cells of the second type including neuron cells (e.g., FIG. 31).

In some embodiments, the cells of the first type include neuron cells; and the third liquid contains cells of a second type, the cells of the second type including vascular endothelial cells and fibroblast cells (e.g., FIG. 32).

In some embodiments, the cells of the first type include neurolemmocytes; and the third liquid contains cells of a second type, the cells of the second type including neuron cells (e.g., FIG. 33).

The microfluidic device with the above-described characteristics has the following advantages. First, the microfluidic device can solve problems caused by low gas saturation in three-dimensional cell culture. That is, in the conventional art, since a culture medium in a reservoir is provided to cells in a microfluidic channel through a long and narrow culture medium channel, gas saturation in the culture medium is reduced while the gas provided from the top surface of the culture medium passes through the culture medium channel, and thus an environment disadvantageous for cells is provided. On the other hand, the microfluidic device is connected to facilitate fluid flow with a culture medium through both open sides of a microfluidic channel and an opening, and therefore a cell culture environment maintaining high gas saturation may be provided.

In addition, the microfluidic device provides rapid and simple fluid patterning. That is, in the microfluidic device, an inner corner path which facilitates fluid flow by capillary force is formed and connected with the microfluidic channel of the microfluidic channel module to facilitate fluid flow, and therefore a suitable amount of the fluid is provided to an arbitrary position on the inner corner path, resulting in easy patterning of the entire microfluidic channels and inner corner paths. This is compared with a need for three or more times of independent fluid injection, for example, when the same fluid is injected into three fluid channels, as in the conventional art. Accordingly, the microfluidic device provides a considerably excellent effect on experiment precision, time and utilization. As described above, since fluid patterning using the microfluidic device can obtain the same patterning result even when a fluid is applied to an arbitrary position on the inner corner path, it can be useful even when a uniform and reproducible repeated experiment is required. This is because the fluid patterning moves until the capillary force applied to the fluid along the inner corner path of the microfluidic device is in equilibrium. When the inner corner path of the microfluidic device has the same contact angle, the fluid patterning can be uniformly performed regardless of external factors such as the experience and skill of an experimenter or operator.

In addition, the microfluidic device may allow patterning of a fluid to a desired area within several seconds, preferably, 1 second after the fluid is applied, and therefore is suitable for an environment requiring rapid and uniform patterning. For example, in three-dimensional co-culture of two or more types of cells, patterning is very important to prevent the mixing of fluids containing different cells. In this case, to fix cells to a specific position under an environment in which free mass transfer is possible, a polymer material, for example, fibrin gel is used together with cells. Here, to cure the fibrin gel mixed with the cells, a generally-used cross-linking agent is added, and for a stable and highly-reliable experiment, rapid and uniform fluid patterning is required.

In addition, the microfluidic device is manufactured of plastic (e.g., an engineering plastic), and the microfluidic device can be manufactured by curing a melted resin by injection molding, hot embossing or 3D printing, and therefore has an advantage of being applicable to economical mass-production. In some embodiments, the plastic is a hydrophilic material. In some embodiments, the plastic is a hydrophobic material.

In some embodiments, the substrate is made of plastic (e.g., an engineering plastic). In some embodiments, the substrate is made of glass.

As described above, the microfluidic device having the above-described structure and advantages does not need other external forces, for example, a pressure, except capillary force, in patterning of a fluid, does not require a separate sensor for precise control of a fluid injection position, and considerably reduces the probability of injection failure, and therefore the microfluidic device can be applied to cell culture using automation equipment.

A microfluidic device, which includes a microfluidic channel embedded in a chamber and open at both sides is manufactured using a material having a hydrophilic surface characteristic, and a fluid can be patterned in a microfluidic channel using capillary force. In accordance with some embodiments, an inner corner path and the microfluidic channel can be used in rapid and precise fluid patterning at one time by applying a suitable amount of the fluid to be patterned on the inner corner path of the microfluidic device. In addition, the microfluidic channel is incorporated or embedded in the lower portion of the chamber, and thus connected to facilitate fluid flow with a culture medium without passing through a long and narrow culture medium channel as shown in the conventional art. Therefore, since cells can easily use a gas entering from an air contact surface, which is on the top surface of the culture medium in the chamber, an advantageous culture environment can be imparted to the cells in the microfluidic channel. Therefore, the microfluidic device can be effectively used in three-dimensional culture of cells or tissue.

This application describes a microfluidic device which includes a microfluidic channel (which is often embedded in a culture medium chamber), and a structure which is formed by capillary force and facilitates fluid flow between an adjacent microfluidic channel and a culture medium. In addition, this application also describes a structure having several microfluidic devices on one common substrate. In addition, the microfluidic device may be manufactured of a hydrophobic engineering plastic by injection molding. Accordingly, the microfluidic device may be effectively used in culture of cells, tissue or cells and tissue, required for three-dimensional culture, and therefore, it may be used in general industries such as biotechnology laboratories, cosmetics development and new drug development.

What is claimed is:

1. A device, comprising:
a substrate having a top surface and a bottom surface opposite to the top surface;
one or more side walls located adjacent to the substrate; and
and one or more beams, a respective beam of the one or more beams having a bottom surface facing the top surface of the substrate and a top surface opposite to the bottom surface of the respective beam facing away from the top surface of the substrate, the respective beam being positioned adjacent to the substrate,
wherein the one or more beams extend from the one or more side walls and at least a portion of the respective beam is spaced apart from the top surface of the substrate to define one or more microfluidic channels to enable movement of a fluid by capillary force between the bottom surface of the respective beam and the top surface of the substrate along the one or more microfluidic channels.

2. The device of claim 1, wherein:
the one or more beams include a beam having an indented bottom surface, the indented bottom surface including a first linear portion, a second linear portion, and a third linear portion;
the second linear portion is located between the first linear portion and the third linear portion;
the first linear portion is separated from the substrate by a first distance;
the second linear portion is separated from the substrate by a second distance that is distinct from the first distance; and
the third linear portion is separated from the substrate by a third distance that is distinct from the second distance.

3. The device of claim 2, wherein the second distance is greater than the first distance and the third distance.

4. The device of claim 3, wherein the second linear portion of the beam includes one or more through-holes that extend from the second linear portion of the indented bottom surface to the top surface of the beam.

5. The device of claim 1, wherein:
the one or more beams include two or more beams that are separated from each other.

6. The device of claim 1, wherein:
the one or more side walls are in contact with the substrate, a respective side wall of the one or more side walls defining a path corresponding to a contact between the substrate and the respective side wall.

7. The device of claim 6, wherein:
the respective side wall and the substrate define an angle that is less than 90 degrees.

8. The device of claim 6, wherein:
a portion of the respective side wall of the one or more side walls is chamfered.

9. The device of claim 1, wherein:
the one or more side walls include a first side wall and a second side wall that is separated from the first side wall; and
the one or more beams include a first beam that extends from the first side wall and a second beam that extends from the second side wall.

10. The device of claim 1, wherein:
the one or more beams include two or more beams, including a first beam and a second beam that is separate from the first beam;
the first beam extends from a first wall location on a first side wall of the one or more side walls;
the second beam extends from a second wall location on the first side wall that is distinct from the first wall location; and
the first side wall defines a first through-hole between (i) a first corner location that is located on the first side wall below the first wall location adjacent to a contact between the first side wall and the substrate and (ii) a second corner location that is located on the first side wall below the second wall location adjacent to a contact between the first side wall and the substrate.

11. The device of claim 10, wherein:
the first beam extends to a third wall location that is distinct from the first wall location and the second wall location;
the second beam extends to a fourth wall location that is distinct from the first wall location, the second wall location, and the third wall location; and
the one or more side walls define a second through-hole between (i) a third corner location that is located on the one or more side walls below the third wall location adjacent to a contact between the one or more side walls and the substrate and (ii) a fourth corner location that is located on the one or more side walls below the fourth wall location adjacent to a contact between the one or more side walls and the substrate.

12. The device of claim 11, wherein:
a respective beam of the two or more beams has an indented bottom surface, the indented bottom surface including a first linear portion, a second linear portion, and a third linear portion;
the second linear portion is located between the first linear portion and the third linear portion;
the first linear portion is separated from the substrate by a first distance;
the second linear portion is separated from the substrate by a second distance that is greater than the first distance;
the third linear portion is separated from the substrate by a third distance that is less than the second distance;
the first linear portion extends from a first wall location on a first side wall of the one or more side walls;
the third linear portion extends from a second wall location on the first side wall that is distinct from the first wall location; and
the first side wall defines a first through-hole between (i) a first corner location that is located on the first side wall below the first wall location adjacent to a contact between the first side wall and the substrate and (ii) a second corner location that is located on the first side wall below the second wall location adjacent to a contact between the first side wall and the substrate.

13. The device of claim 12, wherein:

the first linear portion extends to a third wall location that is distinct from the first wall location and the second wall location;

the third linear portion extends to a fourth wall location that is distinct from the first wall location, the second wall location, and the third wall location; and the one or more side walls define a second through-hole between (i) a third corner location that is located on the one or more side walls below the third wall location adjacent to a contact between the one or more side walls and the substrate and (ii) a fourth corner location that is located on the one or more side walls below the fourth wall location adjacent to a contact between the one or more side walls and the substrate.

14. The device of claim 1, wherein:

the one or more side walls define one or more wells; and the respective beam is coupled with a vertical divider to separate a respective well of the one or more wells into a first chamber on a first side of the vertical divider and a second chamber that is distinct from the first chamber, the second chamber being on a second side of the vertical divider that is opposite to the first side of the vertical divider.

15. The device of claim 1, wherein:

the bottom surface of the respective beam extends curvilinearly.

16. The device of claim 1, wherein:

the respective beam includes a hollow portion, an open end of the hollow portion being positioned adjacent to the substrate.

17. The device of claim 16, including:

one or more side walls, a respective side wall of the one or more side walls being tilted so that a first portion of the respective side wall has a first distance to the respective beam and a second portion of the respective side wall that is located above the first portion of the respective side wall has a second distance to the respective beam that is greater than the first distance to the respective beam.

18. The device of claim 1, further comprising:

a plurality of pillars extending from the top surface of the substrate and positioned at respective locations below the bottom surface of the respective beam, wherein a first subset of the plurality of pillars positioned along a first curvilinear path on the top surface of the substrate and a second subset of the plurality of the plurality of pillars positioned along a second curvilinear path on the top surface of the substrate that is distinct from the first curvilinear path.

* * * * *